United States Patent
Pierre et al.

(10) Patent No.: US 11,136,251 B2
(45) Date of Patent: Oct. 5, 2021

(54) COMPOSITIONS, METHODS, AND DEVICES FOR CAPTURING PHOSPHATE FROM WATER

(71) Applicant: REGENTS OF THE UNIVERSITY OF MINNESOTA, Minneapolis, MN (US)

(72) Inventors: Valerie Christine Pierre, Vadnais Heights, MN (US); Sylvie Lilliane Pailloux, Minneapolis, MN (US); Sheng-Yin Huang, Minneapolis, MN (US); Mandapati V. Ramakrishnam Raju, Eagan, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 149 days.

(21) Appl. No.: 15/934,530

(22) Filed: Mar. 23, 2018

(65) Prior Publication Data

US 2018/0273406 A1 Sep. 27, 2018

Related U.S. Application Data

(60) Provisional application No. 62/475,356, filed on Mar. 23, 2017.

(51) Int. Cl.
*C02F 1/68* (2006.01)
*C07C 65/17* (2006.01)
(Continued)

(52) U.S. Cl.
CPC ............... *C02F 1/683* (2013.01); *C07C 65/17* (2013.01); *C07C 211/13* (2013.01);
(Continued)

(58) Field of Classification Search
CPC ............... C02F 1/683; C02F 2101/105; C02F 2209/06; C07C 211/13; C07C 65/17;
(Continued)

(56) References Cited

U.S. PATENT DOCUMENTS 9,517,424 B2 12/2016 Keaffaber
9,707,329 B2 7/2017 Merchant
(Continued)

FOREIGN PATENT DOCUMENTS

WO WO 2010/015827 A2 2/2010
WO WO 2017/106425 A1 6/2017

OTHER PUBLICATIONS

Hancu, "CEST and PARACEST MR contrast agents" 2010 Acta Radiol., 51(8):910-923.
(Continued)

*Primary Examiner* — Benjamin L Lebron
(74) *Attorney, Agent, or Firm* — Viksnins Harris Padys Malen LLP

(57) ABSTRACT

The present disclosure provides compositions, methods, and devices for sensing, detecting, and/or selectively capturing phosphate from water. An exemplary method includes: contacting a ligand or a rare earth metal complex of a ligand as described herein with an aqueous phosphate-containing medium at a pH of 5 to 12 under conditions sufficient to bind phosphate (e.g., reversibly bind phosphate). In certain embodiments, the method further includes releasing the bound phosphate by contacting the bound phosphate complex with an aqueous medium at a pH of 0 to 4 under conditions sufficient to release the bound phosphate.

17 Claims, 11 Drawing Sheets

(51) Int. Cl.
| | |
|---|---|
| C07C 211/13 | (2006.01) |
| C07C 211/65 | (2006.01) |
| C07C 229/12 | (2006.01) |
| C07C 259/06 | (2006.01) |
| C07D 213/81 | (2006.01) |
| C07D 213/89 | (2006.01) |
| C07D 309/40 | (2006.01) |
| C02F 101/10 | (2006.01) |

(52) U.S. Cl.
CPC .......... *C07C 211/65* (2013.01); *C07C 229/12* (2013.01); *C07C 259/06* (2013.01); *C07D 213/81* (2013.01); *C07D 213/89* (2013.01); *C07D 309/40* (2013.01); C02F 2101/105 (2013.01); C02F 2209/06 (2013.01)

(58) Field of Classification Search
CPC ... C07C 259/06; C07C 229/12; C07D 309/40; C07D 213/81; C07D 213/89; A61K 49/086; A61K 49/10; A61K 49/101; A61K 49/103; A61K 49/126
See application file for complete search history.

(56) References Cited

U.S. PATENT DOCUMENTS

| | | | | |
|---|---|---|---|---|
| 2003/0095922 | A1* | 5/2003 | Raymond | A61K 49/085 424/1.69 |
| 2003/0220518 | A1* | 11/2003 | Bolskar | B82Y 30/00 560/19 |
| 2011/0155669 | A1 | 6/2011 | Pan | |
| 2014/0183405 | A1 | 7/2014 | Hong | |

OTHER PUBLICATIONS

Hao, "MRI contrast agents: basic chemistry and safety" 2012 *J. Magn. Reson. Imaging*, 36(5):1060-71.
Hargrove, "Artificial Receptors for the Recognition of Phosphorylated Molecules" 2011 *Chem. Rev.*, 111:6603-6782.
Harris, "A Gadolinium Complex for Catch-and-Release of Phosphate from Water" Apr. 2017 *Environ Sci Technol.*, 51(8):4549-4558.
Harrison, "Trace elements in human brain: copper, zinc, iron, and magnesium" 1968 *Clinica Chim. Acta*, 21(1):55-60.
Hartter, "Evidence for Release of Copper in the Brain—Depolarization-Induced Release of Newly Taken-up Copper-67" 1988 *Synapse*, 2(4):412-415.
Hasselgren, "Three-coordinate [Cu(II)X3]-(X=Cl, Br):trapped in a molecular crystal" 2002 *Chemistry*, 8(6):1269-78.
Hatai, An inorganic phosphate(P-i) sensor triggers 'turn-on' fluorescence response by removal of a Cu2+ ion from a Cu2+-ligand sensor: determination of P-i in biological samples. Tetrahedron Lett. 2012, 53, 4357-4360.
Hehre, *Ab Initio Molecular Orbital Theory*. Wiley: New York, 1986. Cover page, title page, table of contents.
Hermann, "Gadolinium(III) complexes as MRI contrast agents: ligand design and properties of the complexes" 2008 *Dalton Trans.*,(23):3027-3047.
Herrera, "Structural and photophysical properties of coordination networks combining [Ru(Bpym)(CN)4]2- or [[Ru(CN)4]2(mu-bpym)]4-anions(bpym=2,2'-bipyrimidine) with lanthanide(III) cations: sensitized near-infrared luminescence from Yb(III):Nd(III):and Er(III) following Ru-to-lanthanide energy transfer" 2006 *Inorg. Chem.*, 45(10):3895-904.
Heyduk, "Luminescence resonance energy transfer analysis of RNA polymerase complexes" 2001 *Methods*, 25(1):44-53.
Heyduk, "Measuring protein conformational changes by FRET/LRET" 2002 *Curr. Opin. Biotechnol.*, 13(4):292-296.
Hingorani, "A review of responsive MRI contrast agents: 2005-2014" 2015 *Contrast Media Mol. Imaging*, 10(4):245-265.

Hirayama, "Development of a dual functional luminescent sensor for zinc ion based on a peptidic architecture" 2012 *Bioorg. Med. Chem. Lett.*, 22(24):7410-3.
Hirayama, "Near-infrared fluorescent sensor for in vivo copper imaging in a murine Wilson disease model" 2012 *Proc. Natl. Acad. Sci. U.S.A.*, 109(7):2228-33.
Holland, "Three-Coordinate Cu(II) Complexes: Structural Models of Trigonal-Planar Type 1 Copper Protein Active Sites" 1999 *J. Am. Chem. Soc.*, 121(31):7270-7271.
Horrocks, "Lanthanide Ion Luminescence Probes of the Structure of Biological Macromolecules" 1981 *Acc. Chem. Res.*, 14(12):384-392.
Horrocks, "Lanthanide ion probes of structure in biology. Laser-induced luminescence decay constants provide a direct measure of the number of metal-coordinated water molecules" 1979 *J. Am. Chem. Soc.*, 101(2):334-340.
Howell, "Stimulation-induced uptake and release of zinc in hippocampal slices" 1984 *Nature*, 308(5961):736-8.
Huang, "Phosphate removal from wastewater using red mud" 2008 *J.Hazard. Mater.*, 158(1):35-42.
Ikotun, "Coordination complexes incorporating pyrophosphate: Structural overview and exploration of their diverse magnetic, catalytic and biological properties" 2010 *Coord. Chem. Rev.*, 254, 890-915.
Jang, "Cu2+-Responsive Bimodal(Optical/MRI) Contrast Agent for Cellular Imaging" 2013 *Org. Lett.*, 15(18):4702-4705.
Jeon, "Recycling wasted biomaterial, crab shells, as an adsorbent for the removal of high concentration of phosphate" 2009 *Bioresource Technology*, 100(9):2646-2649.
Jetoo, "The Toledo Drinking Water Advisory: Suggested Application of the Water Safety Planning Approach" 2015 *Sustainability*, 7:9787-9808.
Jiang, "Rational design of a highly sensitive and selective "turn-on" fluorescent sensor for $PO_4^{3-}$ detection" 2015 *Dalton Trans.*, 44:20830-20833.
Jiang, "New fluorenyl-substituted dioxotetraamine ligands and their copper(II) complexes—Crystal structure and fluorescent sensing properties in aqueous solution" 2002 *Eur. J. Inorg. Chem.*, (3):664-670.
Jiang, "An NBD fluorophore-based sensitive and selective fluorescent probe for zinc ion" 2008 *Chem. Commun.*, (2):259-261.
Jitsukawa, "SOD activities of the copper complexes with tripodal polypyridylamine ligands having a hydrogen bonding site" 2001 *Inorg. Chim. Acta*, 324(1-2):108-116.
Jocher, "1,2-Hydroxypyridonates as Contrast Agents for Magnetic Resonance Imaging: TREN-1,2-HOPO" 2007 *Inorg. Chem.*, 46:9182-9191.
Jocher, "Aqueous Ln(III) luminescence agents derived from a tasty precursor" 2008 *Inorg. Chem.*, 47(18):7951-3.
Kadjane, "Improving visible light sensitization of luminescent europium complexes" 2008 *J. Fluoresc.*, 18(1):119-29.
Kalorama Information "Food safety diagnostics" 2016. 2 pgs.
Kambe, "The Physiological, Biochemical, and Molecular Roles of Zinc Transporters in Zinc Homeostasis and Metabolism" 2015 *Physiol. Rev.*, 95(3):749-84.
Kapoerchan, "Design of azidoproline containing gluten peptides to suppress CD4+ T-cell responses associated with Celiac disease" Feb. 2008 *Bioorganic & Medicinal Chemistry* 16(4):2053-2062.
Karlin, "Synthesis and x-ray structural characterization of Cu(I) and Cu(II) derivatives of a new symmetric tripodal ligand N(CH 2 CH 2-py) 3,(py=2-pyridyl)" 1982 *Inorg. Chim. Acta*, 64, L219-L220.
Karlin, "Tetragonal vs. trigonal coordination in copper(II) complexes with tripod ligands: structures and properties of [Cu(C21H24N4)Cl]PF6 and [Cu(C18H18N4)Cl]PF6" 1982 *Inorg. Chem.*, 21(11):4106-4108.
Kasala, "[Gd(Try-TTDA)(H2O)]2-: A new MRI contrast agent for copper ion sensing" 2011 *Dalton Trans.*, 40(18):5018-5025.
Keizer, "Non-Linear Fluorescence Quenching and the Origin of Positive Curvature in Stern-Volmer Plots" 1983 *J. Am. Chem. Soc.*, 105(6):1494-1498.
Kennedy, "Sensitised near-infrared luminescence from lanthanide(III) centres using Re(I) and Pt(II) diimine complexes as energy donors in d-f dinuclear complexes based on 2,3-bis(2-pyridyl)pyrazine" 2007 *Dalton Trans.*,(15):1492-9.

(56) References Cited

OTHER PUBLICATIONS

Kim, "A review of optimization and quantification techniques for chemical exchange saturation transfer MRI toward sensitive in vivo imaging" 2015 *Contrast Media Mol. Imaging*, 10(3):163-178.
Kim, "A new quinoline sensitizer-centered lanthanide chelate and its use for protein labling on Ni-NTA beads for TR LRET assays" 2009 *Chem. Commun.*, (2):183-185.
Kim, "Sensitized emission of luminescent lanthanide complexes based on 4-naphthalen-1-yl-benzoic acid derivatives by a charge-transfer process" 2006 *Chemphyschem*, 7(1):213-21.
Kimani, "Synthesis, characterization, and DFT studies of thione and selone Cu(I) complexes with variable coordination geometries" 2011 *Dalton Trans.*, 40(14):3711-23.
Kimura, "A Tris(ZnII-1,4,7,10-tetraazacyclododecane) Complex as a New Receptor for Phosphate Dianions in Aqueous Solution" 1997 *J. Am. Chem. Soc.*, 119(13):3068-3076.
Koay, "Tuning the metal binding site specificity of a fluorescent sensor protein: from copper to zinc and back" 2013 *Dalton Trans.*, 42(9):3230-2.
Konishi, "Sorption Kinetics of Cobalt in Chelating Porous Membrane" 1992 *Ind. Eng. Chem. Res.*, 31:2722-2727.
Koullourou, "Synthesis and spectroscopic properties of a prototype single molecule dual Imaging agent comprising a heterobimetallic rhenium-gadolinium complex" 2008 *J. Am. Chem. Soc.*, 130(7):2178-2179.
Kozlowski, "Copper, zinc and iron in neurodegenerative diseases(Alzheimer's, Parkinson's and prion diseases)" 2012 *Coord. Chem. Rev.*, 256(19-20):2129-2141.
Kramer, "Fluorescent chemosensors for Cu2+ ions: Fast, selective, and highly sensitive" 1998 *Angew Chem. Int. Ed.*, 37(6):772-773.
Krebs, "The citric acid cycle: A reply to the criticisms of F. L. Breusch and of J. Thomas" 1940 *Biochem. J.*, 34(3):460-3.
Kubik, "Anion recognition in water" 2010 *Chem. Soc. Rev.*, 39:3648-3663.
Kunz, "'Zur Lehre von der Wirkung der Salze' (about the science of the effect of salts): Franz Hofmeister's historical papers" 2004 *Curr. Opin. Colloid Interface Sci.*, 9:19-37.
Kwon, "Fluorescent Zinc Sensor with Minimized Proton-Induced Interferences: Photophysical Mechanism for Fluorescence Turn-On Response and Detection of Endogenous Free Zinc Ions" 2012 *Inorg. Chem.*, 51(16):8760-8774.
Law, "Progress and recent advances in phosphate sensors: A review" 2013 *Talanta*, 114:191-203.
Lazarides, "Heteronuclear bipyrimidine-bridged Ru-Ln and Os-Ln dyads: low-energy(MLCT)-M-3 states as energy-donors to Yb(III) and Nd(III)" 2008 *Dalton Trans.*, (5):691-698.
Lazarides, "Anthracene as a sensitiser for near-infrared luminescence in complexes of Nd(III):Er(III) and Yb(III): an unexpected sensitisation mechanism based on electron transfer" 2007 *Dalton Trans.*, (15):1484-1491.
Lazarides, "On the Mechanism of d-f Energy Transfer in Ru-II/Ln(III) and Os-II/Ln(III) Dyads: Dexter-Type Energy Transfer Over a Distance of 20 angstrom" 2008 *Chem. Eur. J.*, 14(30):9389-9399.
Le Corre, "Phosphorus Recovery from Wastewater by Struvite Crystallization: A Review" 2009 *Crit. Rev. Env. Sci. Technol.*, 39:433-477.
Leonard, "pH driven self-assembly of a ternary lanthanide luminescence complex: the sensing of anions using a beta-diketonate-Eu(III) displacement assay" 2007 *Chem. Commun.*, 129-131.
Li, "High Collection Rate of Pd in Hydrochloric-Acid Medium Using Chelating Microporous Membrane" 1994 *J. Membr. Sci.*, 95:63-69.
Li, "A gadolinium(III) complex with 8-amidequinoline based ligand as copper(II) ion responsive contrast agent" 2011 *Dalton Trans.*, 40(2):484-488.
Li, "Sensitization of lanthanide luminescence in heterotrinuclear PtLn(2)(Ln=Eu, Nd, Yb) complexes with terpyridyl-functionalized alkynyl by energy transfer from a Platinum(II) alkynyl chromophore" 2007 *Organometallics*, 26(18):4483-4490.
Li, "Syntheses, structures, and sensitized lanthanide luminescence by Pt -> Ln(Ln=Eu, Nd, Yb) energy transfer for heteronuclear PtLn(2) and Pt(2)Ln(4) complexes with a terpyridyl-functionalized alkynyl ligand" 2007 *Inorg. Chem.*, 46(25):10892-10900.
Liew, "Gas Fermentation—A Flexible Platform for Commercial Scale Production of Low-Carbon-Fuels and Chemicals from Waste and Renewable Feedstocks" 2016 *Front. Microbiol.*, 7:694.
Lim, "Copper complexes for fluorescence-based NO detection in aqueous solution" 2005 *J. Am. Chem. Soc.*, 127(35):12170-12171.
Liu, "Removal of high-concentration phosphate by calcite: Effect of sulfate and pH" 2012 *Desalination*, 289:66-71.
Liu, "Nuts and bolts of chemical exchange saturation transfer MRI" 2013 *NMR Biomed.*, 26(7):810-828.
Liu, "Two-photon excited fluorescent chemosensor for homogeneous determination of copper(II) in aqueous media and complicated biological matrix" 2011 *Analyst*, 136(10):2139-45.
Liu, "An effective Cu(II) quenching fluorescence sensor in aqueous solution and 1D chain coordination polymer framework" 2011 *Dalton Trans.*, 40(37):9370-3.
Liu, "Metal coordination in photoluminescent sensing" 2013 *Chem Soc Rev.*, 42(4):1568-1600.
Lovell, "Copper, iron and zinc in Alzheimer's disease senile plaques" 1998 *J. Neurol. Sci.*, 158(1):47-52.
Lucchese, "Mono-, bi-, and trinuclear CuII-Cl containing products based on the tris(2-pyridylmethyl)amine chelate derived from copper(I) complex dechlorination reactions of chloroform" 2004 *Inorg. Chem.*, 43(19):5987-98.
Luo, "Zn2+ Responsive Bimodal Magnetic Resonance Imaging and Fluorescent Imaging Probe Based on a Gadolinium(III) Complex" 2012 *Inorg. Chem.*, 51(17):9508-9516.
Major, "Mechanisms of Zn(II)-Activated Magnetic Resonance Imaging Agents" 2008 *Inorg. Chem.*, 47(22):10788-10795.
Major, "The synthesis and in vitro testing of a zinc-activated MRI contrast agent" 2007 *Proc. Natl. Acad. Sci. U.S.A.*, 104(35):13881-13886.
Mapare, "A Review of Sensor Technology for In-field Phosphate monitoring" 2013 *Int. Conf. Sens. Technol.*, 411-418.
Marchetti, "Interaction of metal ions with neurotransmitter receptors and potential role in neurodiseases" 2014 *Biometals*, 27(6):1097-1113.
Marenich, "Universal Solvation Model Based on Solute Electron Density and on a Continuum Model of the Solvent Defined by the Bulk Dielectric Constant and Atomic Surface Tensions" 2009 *J. Phys. Chem. B*, 113(18):6378-6396.
Martinez-Peragon, "Rational design of a new fluorescent 'On/Off' xanthene dye for phosphate detection in live cells" 2014 *Org. Biomol. Chem.*, 12:6432-6439.
Matosziuk, "Structural Optimization of Zn(II)-Activated Magnetic Resonance Imaging Probes" 2013 *Inorg. Chem.*, 52(21):12250-12261.
Maynard, "Metals and amyloid-beta in Alzheimer's disease" 2005 *Int. J. Exp. Pathol.*, 86(3):147-159.
Mayr, "Fluorimetric determination of copper(II) in aqueous solution using lucifer yellow CH as selective metal reagent" 2001 *Fresenius J. Anal. Chem.*, 371(1):44-48.
McGowan, "Basic principles of magnetic resonance imaging" 2008 *Neuroimaging Clin. N. Am.*, 18(4):623-636.
McNemar, "Europium(III) Ion Luminescence as a Structural Probe of Parvalbumin Isotypes" 1990 Biochim. Biophys. Acta, 1040(2):229-236.
Mehlstaubl, "Sensitized near-infrared emission from ytterbium(III) via direct energy transfer from iridium(III) in a heterometallic neutral complex" 2008 *Dalton Trans.*, (18):2385-2388.
Mehta, "Technologies to Recover Nutrients from Waste Streams: A Critical Review" 2015 *Crit. Rev. Environ. Sci. Technol*, 45, 385-427.
Merbach, The Chemistry of Contrast Agents in Medical Magnetic Resonance Imaging. Second Edition ed.; John Wiley & Sons Publication: United Kingdom, 2013. Cover page, publisher page, and table of contents.
Mishra, "Critical In Vitro Evaluation of Responsive MRI Contrast Agents for Calcium and Zinc" 2011 *Chem. Eur. J.*, 17(5):1529-1537.

(56) References Cited

OTHER PUBLICATIONS

Montes, "Copper and Copper Proteins in Parkinson's Disease" Jan. 2014 Oxid. Med. Cell Longev., 2014:147251. doi: 10.1155/2014/147251.
Mummidivarapu, Interaction of a dinuclear fluorescent Cd(II) complex of calix[4]arene conjugate with phosphates and its applicability in cell imaging. Dalton Trans. 2015, 44, 1130-1141.
Murugavel, "Metal complexes of organophosphate esters and open-framework metal phosphates: Synthesis, structure, transformations, and applications" 2008 Chem. Rev., 108:3549-3655.
Nie, "Energy transfer pathways in the carbazole functionalized beta-diketonate europium complexes" 2007 New J. Chem., 31(9):1639-1646.
Nieto, "Pt(II)-activated coupling of aminoethylferrocene with benzonitrile. A facile access route to a new redox-active bis(ferrocenyl-amidine) anion sensor" 2011 Chem. Commun., 47:10398-10400.
Nolan, "QZ1 and QZ2: Rapid, reversible quinoline-derivatized fluoresceins for sensing biological Zn(II)" 2005 J. Am. Chem. Soc., 127(48):16812-16823.
Oishi, "Simultaneous biobehavior of trace elements, Sc, Mn, Fe, Co, Zn, Se, Rb and Zr in the brain and other organs of C57BL/6N mice" 1999 J. Radioanal. Nucl. Chem., 239(2):411-416.
Osako, "Modulation of coordination chemistry in copper(I) complexes supported by Bis[2-(2-pyridyl)ethyl]amine-based tridentate ligands" 2001 Inorg. Chem., 40(26):6604-9.
Oton, "A ferrocene-based heteroditopic ligand for electrochemical sensing of cations and anions" 2005 Dalton Trans., 7:1159-1161.
Ou, "Highly efficient removal of phosphate by lanthanum-doped mesoporous SiO2" 2007 Colloid Surf. A., 308(1-3):47-53.
Patterson, "Structural and electronic effects on the polarographic half-wave potentials of copper(II) chelate complexes" 1975 Bioinorg. Chem., 4(3):257-75.
Pelley, "Taming Toxic Algae Blooms" 2016 ACS Cent. Sci., 2:270-273.
Peters, "Lanthanide induced shifts and relaxation rate enhancements" 1996 Prog. Nucl. Mag. Res. Sp., 28:283-350.
Peterson, "Basis for Sensitive and Selective Time-Delayed Luminescence Detection of Hydroxyl Radical by Lanthanide Complexes" 2013 Inorg. Chem., 52(16):9390-9398.
Pierre, "Substituent effects on Gd(III)-based MRI contrast agents: Optimizing the stability and selectivity of the complex and the number of coordinated water molecules" 2006 Inorg. Chem., 45:8355-8364.
Piguet, "Lanthanide podates with predetermined structural and photophysical properties: Strongly luminescent self-assembled heterodinuclear d-f complexes with a segmental ligand containing heterocyclic imines and carboxamide binding units" 1996 J. Am. Chem. Soc., 118(28):6681-6697.
Ping, "Phosphate removal from wastewater by model-La(III) zeolite adsorbents" 2008 J. Environ. Sci-China, 20(6):670-674.
Piszczek, "Multi-photon sensitized excitation of near infrared emitting lanthanides" 2002 J. Fluoresc., 12(1):15-17.
Pope, "Self-assembly of luminescent ternary complexes between seven-coordinate lanthanide(III) complexes and chromophore bearing carboxylates and phosphonates" 2006 Dalton Trans.,(23):2907-2912.
Pope, "Re(I) sensitised near-infrared lanthanide luminescence from a hetero-trinuclear Re(2)Ln array" 2004 Chem. Commun.,(13):1550-1551.
Pope, "Self-assembly of heterobimetallic d-f hybrid complexes: Sensitization of lanthanide luminescence by d-block metal-to-ligand charge-transfer excited states" 2004 J. Am. Chem. Soc., 126(31):9490-9491.
Pope, "Design, synthesis and photophysical studies of an emissive, europium based, sensor for zinc" 2006 Dalton Trans.,(25):3108-3113.
Potter, "Studies on the mechanism of hydrogen transport in animal tissues: VI. Inhibitor studies with succinic dehydrogenase" 1943 J. Gen. Physiol., 26(4):391-404.
Pramanik, "An efficient phosphate sensor: tripodal quinoline excimer transduction" 2009 Tetrahedron, 65:2196-2200.
Puerta, Tris(pyrone) chelates of Gd(III) as high solubility MRI-CA. J. Am. Chem. Soc. 2006, 128, 2222-2223.
Que, "A smart magnetic resonance contrast agent for selective copper sensing" 2006 J. Am. Chem. Soc., 128(50):15942-15943.
Que, "Responsive magnetic resonance imaging contrast agents as chemical sensors for metals in biology and medicine" 2010 Chem. Soc. Rev., 39(1):51-60.
Que, "Metals in neurobiology: Probing their chemistry and biology with molecular imaging" 2008 Chem. Rev., 108(5):1517-1549.
Que, "A copper-activated magnetic resonance imaging contrast agent with improved turn-on relaxivity response and anion compatibility" 2010 Dalton Trans. , 39(2):469-476.
Que, "Copper-Responsive Magnetic Resonance Imaging Contrast Agents" 2009 J. Am. Chem. Soc., 131(24):8527-8536.
Que, "A cell-permeable gadolinium contrast agent for magnetic resonance imaging of copper in a Menkes disease model" 2012 Chem. Sci., 3(6):1829-1834.
Querol, "Amplification strategies in MR imaging: Activation and accumulation of sensing contrast agents(SCAs)" 2006 J. Magn. Reson. Imaging, 24(5):971-982.
Rajendran, "An unusual axial co-ordination of phenolate oxygen to copper(II): crystal structure of chloro{2-[bis(2-pyridylmethyl)aminomethyl]-4-nitrophenolato}copper(II)" 1992 J. Chem. Soc., Dalton Trans.,(24):3563-3564.
Rapp, "Defining the Catechol-Cation Synergy for Enhanced Wet Adhesion to Mineral Surfaces" Jul. 2016 J. Am. Chem. Soc., 138(29):9013-6.
Rayner, "Effect of medium copper concentration on the growth, uptake and intracellular balance of copper and zinc in Menkes' and normal control cells" 1994 Biometals, 7(3):253-260.
Regueiro-Figueroa, "Gd3+-Based Magnetic Resonance Imaging Contrast Agent Responsive to Zn2+" 2015 Inorg. Chem., 54(21):10342-10350.
Rembach, "Decreased serum zinc is an effect of ageing and not Alzheimer's disease" 2014 Metallomics, 6(7):1216-1219.
Rhee, "Lanthanide Ion Luminescence Probes—Characterization of Metal-Ion Binding-Sites and Intermetal Energy-Transfer Distance Measurements in Calcium-Binding Proteins" 1981 1. Parvalbumin. Biochemistry, 20(12):3328-3334.
Rivas, "Towards understanding the design of dual-modal MR/fluorescent probes to sense zinc ions" 2015 Dalton Trans., 44(11):4976-4985.
Rodriguez-Castro, "Wilson's disease: A review of what we have learned" 2015 World J. Hepatol., 7(29):2859-2870.
Ronson, "Luminescent Pt-II(bipyridyl)(diacetylide) chromophores with pendant binding sites as energy donors for sensitised near-infrared emission from lanthanides: Structures and photophysics of Pt-II/Ln(III) assemblies" 2006 Chem. Eur. J., 12(36):9299-9313.
Rose, "Mechanism of copper(II)-induced misfolding of Parkinson's disease protein" 2011 Sci. Rep., 1-5.
Rudkevich, "Anion Recognition by Neutral Receptors in *Molecular Design and Bioorganic Catalyst*" Wilcok, Ed. Kluwer Academic Publishers: Dordrecht, 1996; Cover page, publisher page, pp. 137-159.
Rurack, "A selective and sensitive fluoroionophore for Hg(II):Ag(I):and Cu(II) with virtually decoupled fluorophore and receptor units" 2000 J. Am. Chem. Soc., 122(5):968-969.
Saghiri, "Functional role of inorganic trace elements in angiogenesis—Part II: Cr, Si, Zn, Cu, and S" 2015 Crit. Rev. Oncol. Hematol., 96(1):143-155.
Sanni, "Copper(II) and zinc(II) co-ordination compounds of tridentate bis(benzimidazole)pyridine ligands. Crystal and molecular structures of bis[2,6-bis(1[prime or minute]-methylbenzimidazol-2[prime or minute]-yl)pyridine]copper(II) diperchlorate monohydrate and(acetonitrile)[2,6-bis(benzimidazol-2[prime or minute]-yl)pyridine](perchlorato)copper(II) perchlorate" 1988 J. Chem. Soc., Dalton Trans., (6):1429-1435.
SBI Energy "Global Market for Membrane Wastewater Treatment" Oct. 2012 Market Res. Acad., 3 pgs.
Schindler, "Reducing Phosphorus to Curb Lake Eutrophication is a Success" 2016 Environ. Sci. Technol., 50, 8923-8929.

(56) References Cited

OTHER PUBLICATIONS

Schmidtchen, "Isothermal Titration Calorimetry in Supramolecular Chemistry" in *Supramol. Chem.*, John Wiley & Sons, Ltd: 2012. Cover page, publisher page and "Isothermal Titration Calorimetry in Supramolecular Chemistry" section.
Scott, "Medicinal Inorganic Chemistry Approaches to Passivation and Removal of Aberrant Metal Ions in Disease" 2009 *Chem. Rev.*, 109(10):4885-4910.
Selvin, "The renaissance of fluorescence resonance energy transfer" 2000 *Nat. Struct. Biol.*, 7(9):730-734.
Selvin, "Luminescence energy transfer using a terbium chelate: improvements on fluorescence energy transfer" 1994 *Proc. Natl. Acad. Sci. U. S. A.*, 91(21):10024-8.
Selvin, "Luminescence Resonance Energy-Transfer" 1994 *J. Am. Chem. Soc.*, 116(13):6029-6030.
Senechal-David, "Sensitized near-infrared lanthanide luminescence from Nd(III)- and Yb(III)-based cyclen-ruthenium coordination conjugates" 2006 *Inorg. Chem.*, 45(25):10040-10042.
Shavaleev, "Syntheses and crystal structures of dinuclear complexes containing d-block and f-block luminophores. Sensitization of NIR luminescence from Yb(III):Nd(III):and Er(III) centers by energy transfer from Re(I)and Pt(II)-bipyrimidine metal centers" 2005 *Inorg. Chem.*, 44(1):61-72.
Shavaleev, "Sensitised near-infrared emission from lanthanides using a covalently-attached Pt(II) fragment as an antenna group" 2003 *Chem. Commun.*, (10):1134-5.
Smit, "Phosphorus in Agriculture: Global Resources, Trends and Developments" Steering Committee Technology Assessment of the Ministry of Agriculture, Nature, and Food Quality. Plant Research International B.V. The Netherlands: Wagenigen University, 2009.
Smith, "Measuring Equilibrium Bicarbonate Concentrations Directly in Cellular Mitochondria and in Human Serum Using Europium/Terbium Emission Intensity Ratios" 2012 *Chem. Eur. J.*, 18(37):11604-11613.
Smolensky, "A responsive particulate MRI contrast agent for copper(I): a cautionary tale" 2012 *Dalton Trans.*, 41(26):8039-8046.
Snyder, "Lanthanide Ion Luminescence Probes—Characterization of Metal-Ion Binding-Sites and Intermetal Energy-Transfer Distance Measurements in Calcium-Binding Proteins .2. Thermolysin" 1981 *Biochemistry*, 20(12):3334-3339.
Soesbe, "Advantages of paramagnetic chemical exchange saturation transfer(CEST) complexes having slow to intermediate water exchange properties as responsive MRI agents" 2013 *NMR Biomed.*, 26(7):829-838.
Song, "A europium(III) complex as an efficient singlet oxygen luminescence probe" 2006 *J. Am. Chem. Soc.*, 128(41):13442-50.
Spaulding, "Intermolecular Energy-Transfer between Lanthanide Complexes .8. Tb(III) Donor and Eu(III) Acceptor Complexes of Citric-Acid" 1983 *J. Lumin.*, 28(4):385-394.
Spaulding, "Intermolecular Energy-Transfer between Lanthanide Complexes .9. Terbium(III) Donor and Europium(III) Acceptor Complexes of Amino Polycarboxylic Acids" 1983 *Inorg. Chem.*, 22(23):3486-3488.
Spaulding, "Solution Chemistry of Lanthanide Complexes. 7. Terbium(III) and Europium(III) Complexes of(S,S)-Ethylenediamine-N,N'-Disuccinic Acid" 1984 *Inorg. Chem.*, 23(14):2165-2170.
Stancanello, "Development and validation of a smoothing-splines-based correction method for improving the analysis of CEST-MR images" 2008 *Contrast Media Mol. Imaging*, 3(4):136-149.
Stasiuk, "Dual-modal magnetic resonance/fluorescent zinc probes for pancreatic beta-cell mass imaging" 2015 *Chemistry*, 21(13):5023-5033.
Su, "Chemistry of tripodal ligands. Part III.: Copper complexes of tris(benzimidazol-2-ylmethyl)amine and of its N-n-propyl derivative1" 1999 *Polyhedron*, 18(11):1577-1585.
Suganya, "A highly fluorescent zinc complex of a dipodal N-acyl hydrazone as a selective sensor for $H_2PO_4^-$ ions and application in living cells" 2015 *Inorg. Chem. Front.*, 2:649-656.

Supkowski, "On the determination of the number of water molecules, q, coordinated to europium(III) ions in solution from luminescence decay lifetimes" 2002 *Inorg. Chim. Acta* 2002, 340, 44-48.
Svane, "Effect of Metals in Biomimetic Dimetal Complexes on Affinity and Gas-Phase Protection of Phosphate Esters" 2015 *Anal. Chem.*, 87, 7060-7068.
Swift, "NMR-Relaxation Mechanisms of O17 in Aqueous Solutions of Paramagnetic Cations and the Lifetime of Water Molecules in the First Coordination Sphere" 1962 *J. Chem. Phys.*, 37:307-320.
Takeda, "Zinc-65 imaging of rat brain tumors" 2001 *Cancer Res.*, 61(13):5065-5069.
Taki, "Development of Highly Sensitive Fluorescent Probes for Detection of Intracellular Copper(I) in Living Systems" 2010 *J. Am. Chem. Soc.*, 132(17):5938.
Tanaka, "Synthesis and Metal-Ion Binding Properties of Monoazathiacrown Ethers" 2001 *J. Org. Chem.*, 66(21):7008-7012.
Telgmann, "Determination of gadolinium-based MRI contrast agents in biological and environmental samples: a review" 2013 *Anal. Chim. Acta*, 764:1-16.
Terreno, "Encoding the frequency dependence in MRI contrast media: the emerging class of CEST agents" 2010 *Contrast Media Mol. Imaging*, 5(2):78-98.
Terreno, "Methods for an improved detection of the MRI-CEST effect" 2009 *Contrast Media Mol. Imaging*, 4(5):237-247.
Thibon, "A highly selective luminescent sensor for the time-gated detection of potassium" 2009 *J. Am. Chem. Soc.*, 131(2):434-5.
Thibon, "Principles of responsive lanthanide-based luminescent probes for cellular imaging" 2009 *Anal. Bioanal. Chem.*, 394(1):107-120.
Thordarson, "Determining association constants from titration experiments in supramolecular chemistry" 2011 *Chem. Soc. Rev.*, 40(3):1305-1323.
Tobey, "$C_{3v}$ symmetric receptors show high selectivity and high affinity for phosphate" 2003 *J. Am. Chem. Soc.*, 125:4026-4027.
Tobey, "Energetics of phosphate binding to ammonium and guanidinium containing metallo-receptors in water" 2003 *J. Am. Chem. Soc.*, 125:14807-14815.
Tonzetich, "Detecting and Understanding the Roles of Nitric Oxide in Biology" 2010 *Inorg. Chem.*, 49(14):6338-6348.
Toth, "Stability-Constants of the Lanthanide(Iii)-1,4,7,10-Tetraazacyclododecane-N,N',N'',N'''-Tetraacetate Complexes" 1994 *Inorg. Chim. Acta*, 221(1-2):165-167.
Tremblay, "Cocktails of Tb3+ and Eu3+ complexes: A general platform for the design of ratiometric optical probes" 2007 *J. Am. Chem. Soc.*, 129(24):7570-7577.
Trokowski, "Selective Sensing of Zinc Ions with a PARACEST Contrast Agent" 2005 *Angew Chem. Int. Ed.*, 44(42):6920-6923.
Tsuge, "Intramolecular reductive nitrosylation: Reaction of nitric oxide and a copper(ll) complex of a cyclam derivative with pendant luminescent chromophores" 2004 *J. Am. Chem. Soc.*, 126(21):6564-6565.
Tsuneda, "Metal Collection Using Chelating Hollow Fiber Membrane" 1991 *J. Membr. Sci.*, 58, 221-234.
Ueno, "Three Years Experience of Operating and Selling Recovered Struvite from Full-Scale Plant" 2001 *Environ. Technol.*, 22:1373-1381.
Van Loon, "Structures of dysprosium(III) triflates in water, methanol, and 2-propanol as studied by O-17 and F-19 NMR spectroscopy" 1999 *Inorg. Chem.*, 38(13):3080-3084.
Van Zijl, "Chemical exchange saturation transfer(CEST): What is in a name and what isn't?" 2011 *Mag. Reson. Med.*, 65(4):927-948.
Viguier, "A sensitized europium complex generated by micromolar concentrations of copper(I): toward the detection of copper(I) in biology" 2006 *J. Am. Chem. Soc.*, 128(35):11370-1.
Vinogradov, "From basic principles to applications, challenges and opportunities" 2013 *J. Magn. Reson.*, 229, 155-172.
Vogel, "Improving lanthanide-based resonance energy transfer detection by increasing donor-acceptor distances" 2006 *J. Biomol. Screen.*, 11 (4):439-443.
Vuojola, "Luminescent lanthanide reporters: new concepts for use in bioanalytical applications" 2014 *Methods Appl. Fluoresc.*, 2(1).

(56) References Cited

OTHER PUBLICATIONS

Wang, "A pH-resistant Zn(II) sensor derived from 4-aminonaphthalimide: design, synthesis and intracellular applications" 2005 *J. Mater. Chem.*, 15(27-28):2836-2839.
Wang, "Recent developments in lanthanide-based luminescent probes" 2014 *Coord. Chem. Rev.*, 273, 201-212.
Wang, "Application and Analysis of Methods for Selecting an Optimal Solution from the Pareto-Optimal Front obtained by Multiobjective Optimization" 2017 *Ind. Eng. Chem. Res.*, 56 (2):560-574.
Ward, "Neutron activation analysis techniques for identifying elemental status in Alzheimer's disease" 1987 *J. Radioanal. Nucl. Chem.*, 113(2):515-526.
Watson, "Methane production and emission from peat: the influence of anions(sulphate, nitrate) from acid rain" 1998 *Atmos. Environ.*, 32(19):3239-3245.
Wei, "Copper(I) Complexes with Pyridyl- and Imidazoyl-Containing Tripodal Tetradentate Ligands and Their Reactions with Dioxygen" 1994 *Inorg. Chem.*, 33(6):1177-1183.
Weitz, "A selective luminescent probe for the direct time-gated detection of adenosine triphosphate" 2012 *J. Am. Chem. Soc.*, 134(39):16099-16102.
Weitz, "The basis for the molecular recognition and the selective time-gated luminescence detection of ATP and GTP by a lanthanide complex" 2013 *Chem. Sci.*, 4(10):4052-4060.
Weitz, "Supplemental information: The basis for the molecular recognition and the selective time-gated luminescence detection of ATP and GTP by a lanthanide complex" 2013 *Chem. Sci.*, 4(10):4052-4060.
Weitz, "A Magnetoplasmonic Imaging Agent for Copper(I) with Dual Response by MRI and Dark Field Microscopy" 2013 ACS Nano, 7(7):5842-5849.
Werts, "Bathochromicity of Michler's ketone upon coordination with lanthanide(III) beta-diketonates enables efficient sensitisation of Eu3+ for luminescence under visible light excitation" 1999 *Chem. Commun.*, (9):799-800.
Woods, "Paramagnetic lanthanide complexes as PARACEST agents for medical imaging" 2006 *Chem. Soc. Rev.*, 35(6):500-511.
Wu, Removal of phosphate from water by a highly selective La(III)-chelex resin. Chemosphere 2007, 69(2):289-294.
Wu, "An overview of CEST MRI for non-MR physicists" 2016 EJNMMI Phys., 3(1).
Wu, "Boron dipyrromethene fluorophore based fluorescence sensor for the selective imaging of Zn(II) in living cells" 2005 Org. Biomol. Chem., 3(8):1387-1392.
Xiang, "New fluorescent rhodamine hydrazone chemosensor for Cu(II) with high selectivity and sensitivity" 2006 *Org. Lett.*, 8(13):2863-2866.
Xiao, "A smart copper(II)-responsive binuclear gadolinium(III) complex-based magnetic resonance imaging contrast agent" 2014 RSC Adv., 4(65):34421-34427.
Xiao, "Lanthanide Complex-Based Luminescent Probes for Highly Sensitive Time-Gated Luminescence Detection of Hypochlorous Acid" 2012 *Anal. Chem.*, 84(24):10785-10792.
Xie, "Synthesis, physico-chemical properties, and antimicrobial evaluation of a new series of iron(III) hexadentate chelators" 2013 *Med. Chem. Res.*, 22(5):2351-2359.
Xiong, "Phosphate removal from solution using steel slag through magnetic separation" 2008 *J.Hazard. Mater.*, 152(1):211-215.
Xu, "Modulation of Pt -> Ln Energy Transfer in PtLn(2)(Ln=Nd, Er, Yb) Complexes with 2,2'-Bipyridyl/2,2':6' 2"-Terpyridyl Ethynyl Ligands" 2009 *Cryst. Growth Des.*, 9(1):569-576.
Xu, "Conformation Changes and Luminescent Properties of Au-Ln(Ln= Nd, Eu, Er, Yb) Arrays with 5-Ethynyl-2,2'-Bipyridine" 2008 *Inorg. Chem.*, 47(22):10744-10752.
Xu, "Heterododecanuclear Pt(6)Ln(6)(Ln=Nd, Yb) arrays of 4-ethynyl-2,2'-bipyridine with sensitized near-IR lanthanide luminescence by Pt -> Ln energy transfer" 2007 *Chem. Commun.*, (26):2744-2746.
Xu, "Zn2+-Responsive Bimodal Magnetic Resonance Imaging and Fluorescence Imaging Agents and Their Interaction with Human Serum Albumin" 2014 *Eur. J. Inorg. Chem.*, (20):3208-3215.
Xu, "Colorimetric and ratiometric fluorescent chemosensor with a large red-shift in emission: Cu(II)-only sensing by deprotonation of secondary amines as receptor conjugated to naphthalimide fluorophore" 2005 *Org. Lett.*, 7(14):3029-3032.
Xu, "Ratiometric and selective fluorescent sensor for Cu-II based on internal charge transfer(ICT)" 2005 *Org. Lett.*, 7(5):889-892.
Xu, "Fluorescent chemosensors for Zn2+" Apr. 2010 *Chem. Soc. Rev.*, 39(6):1996-2006.
Xue, "Characteristics and mechanisms of phosphate adsorption onto basic oxygen furnace slag" 2009 *J. Hazard. Mat.*, 162(2-3):973-980.
Yang, "Imaging of the intracellular topography of copper with a fluorescent sensor and by synchrotron x-ray fluorescence microscopy" 2005 *Proc. Natl. Acad. Sci. U.S.A.*, 102(32):11179-84.
Yeon, "Zirconium mesostructures immobilized in calcium alginate for phosphate removal" 2008 *Korean J. Chem. Eng.*, 25(5):1040-1046.
Yu, "Amplifying the Sensitivity of Zinc(II) Responsive MRI Contrast Agents by Altering Water Exchange Rates" 2015 *J. Am. Chem. Soc.*, 137(44):14173-14179.
Yu, "Highly sensitive and fast responsive fluorescence turn-on chemodosimeter for Cu(2+) and its application in live cell imaging" 2008 *Chem. Eur. J.*, 14(23):6892-6900.
Zaiss, "Chemical exchange saturation transfer(CEST) and MR Z-spectroscopy in vivo: a review of theoretical approaches and methods" 2013 *Phys. Med. Biol.*, 58(22):R221-R269.
Zeng, "Adsorptive removal of phosphate from aqueous solutions using iron oxide tailings" 2004 *Water Res.*, 38(5):1318-1326.
Zeng, "A selective turn- on fluorescent sensor for imaging copper in living cells" 2006 *J. Am. Chem. Soc.*, 128(1):10-1.
Zhang, "Interactions between macromolecules and ions: the Hofmeister series" 2006 *Curr. Opin. Chem. Biol.*, 10, 658-663.
Zhang, "Removal of phosphate from water by a Fe—Mn binary oxide adsorbent" 2009 *J. Colloid Interface Sci.*, 335(2):168-174.
Zhang, "PARACEST agents: Modulating MRI contrast via water proton exchange" 2003 *Acc. Chem. Res.*, 36(10):783-790.
Zhang, "Dual-Functional Gadolinium-Based Copper(II) Probe for Selective Magnetic Resonance Imaging and Fluorescence Sensing" 2012 *Inorg. Chem.*, 51(4):2325-2331.
Zhang, "Water-soluble porphyrins as a dual-function molecular imaging platform for MRI and fluorescence zinc sensing" 2007 *Proc. Natl. Acad. Sci.*, 104(26):10780-10785.
Zhang, "Ratiometric and water-soluble fluorescent zinc sensor of carboxamidoquinoline with an alkoxyethylamino chain as receptor" 2008 *Org. Lett.*, 10(3):473-476.
Zhao, "A new local density functional for main-group thermochemistry, transition metal bonding, thermochemical kinetics, and noncovalent interactions" 2006 *J. Chem. Phys.*, 125(19).
Zhao, "Density functionals with broad applicability in chemistry" 2008 *Acc. Chem. Res.*, 41(2):157-167.
Zou, "A disposable on-chip phosphate sensor with planar cobalt microelectrodes on polymer substrate" 2007 *Biosens. Bioelectron.*, 22(9-10):1902-1907.
Aboshyan-Sorgho, "Optimizing millisecond time scale near-infrared emission in polynuclear chrome(III)-lanthanide(III) complexes" 2012 *J. Am. Chem. Soc.*, 134(30):12675-84.
Addison, "Is ligand topology an influence on the redox potentials of copper complexes?" 1989 *Inorg. Chim. Acta*, 162(2):217-220.
Aime, "Gd(III) complexes as contrast agents for magnetic resonance imaging: A proton relaxation enhancement study of the interaction with human serum albumin" 1996 *J. Biol. Inorg. Chem.*, 1:312-319.
Aime, Insights into the use of paramagnetic Gd(III) complexes in MR-molecular imaging investigations. J. Magn. Reson. Imaging 2002, 16(4):394-406.
Albizu, "Time-resolved FRET between GPCR ligands reveals oligomers in native tissues" Jul. 2010 *Nature Chemical Biology*, 6:587-594.
Alfredo, "Chlorate challenges for water systems" 2015 *J. Am. Water Works. Assn.*, 107:E187-E196.
Allegrozzi, "Lanthanide-induced pseudocontact shifts for solution structure refinements of macromolecules in shells up to 40 angstrom from the metal ion" 2000 *J. Am. Chem. Soc.*, 122(17):4154-4161.

(56) References Cited

OTHER PUBLICATIONS

Amoroso, "Using lanthanide ions in molecular bioimaging" 2015 Chem. Soc. Rev., 44(14):4723-4742.
Andolina, Luminescence Resonance Energy Transfer in Heterodinuclear Ln(III) Complexes for Sensing Biologically Relevant Anions. Eur. J. Inorg. Chem. 2011, 1, 154-164.
Andrae, "Energy-Adjusted Abinitio Pseudopotentials for the 2nd and 3rd Row Transition-Elements" 1990 Theor. Chim. Acta, 77(2):123-141.
Andres, "Expanding the Versatility of Dipicolinate-Based Luminescent Lanthanide Complexes: A Fast Method for Antenna Testing" 2015 Inorg. Chem., 54(17):8174-8176.
Aoki, "A Double-Functionalized Cyclen with Carbamoyl and Dansyl Groups(Cyclen=1,4,7,10-Tetraazacyclododecane): A Selective Fluorescent Probe for Y3+ and La3+" 2001 J. Am. Chem. Soc., 123(6):1123-1132.
Assaf, "Release of endogenous $Zn^{2+}$ from brain tissue during activity" 1984 Nature, 308(5961):734-6.
Baca, "Three-component coordination networks based on [Ru(phen)(CN)4](2-) anions, near-infrared luminescent lanthanide(III) cations, and ancillary oligopyridine ligands: structures and photophysical properties" 2007 Dalton Trans.,(23):2419-30.
Balamurugan, "Trigonal Planar Copper(I) Complex: Synthesis, Structure, and Spectra of a Redox Pair of Novel Copper(II/I) Complexes of Tridentate Bis(benzimidazol-2'-yl) Ligand Framework as Models for Electron-Transfer Copper Proteins" 2001 Inorg. Chem., 40(10):2246-2255.
Bansal, "Serum Inorganic Phosphorus" in Clinical Methods: The History, Physical, and Laboratory Examinations., 3rd edition. Walker, Ed. Boston, MA: Butterworths: 1990. Cover page, title page, table of contents, and section "Serum Inorganic Phosphorus."
Barglow, "Substrate Mimicry in an Activity-Based Probe That Targets the Nitrilase Family of Enzymes" 2006 Angew. Chem. Int. Ed., 45(44):7408-7411.
Barnham, "Metals in Alzheimer's and Parkinson's Diseases" 2008 Curr. Opin. Chem. Biol., 12(2):222-228.
Basa, "Differential Sensing of Zn(II) and Cu(II) via Two Independent Mechanisms" 2012 J. Org. Chem., 77(19):8428-8434.
Becker, "Imaging of copper, zinc, and other elements in thin section of human brain samples(hippocampus) by laser ablation inductively coupled plasma mass spectrometry" 2005 Anal. Chem., 77(10):3208-16.
Beeby, "Non-radiative deactivation of the excited states of europium, terbium and ytterbium complexes by proximate energy-matched OH, NH and CH oscillators: an improved luminescence method for establishing solution hydration states" 1999 J. Chem. Soc. Perkin Trans. 2,(3):493-503.
Bellingham, "Copper depletion down-regulates expression of the Alzheimer's disease amyloid-beta precursor protein gene" 2004 J. Biol. Chem., 279(19):20378-20386.
Bergendahl, "On-column tris(2-carboxyethyl)phosphine reduction and IC5-maleimide labeling during purification of a RpoC fragment on a nickel-nitrilotriacetic acid Column" 2002 Anal. Biochem., 307(2):368-374.
Bergendahl, "Luminescence resonance energy transfer-based high-throughput screening assay for inhibitors of essential protein-protein interactions in bacterial RNA polymerase" 2003 Appl. Environ. Microbiol., 69(3):1492-1498.
Bhattacharyya, "Novel poly-glutamic acid functionalized microfiltration membranes for sorption of heavy metals at high capacity" 1998 J. Membr. Sci., 141, 121-135.
Biswas, "Removal and recovery of phosphorus from water by means of adsorption onto orange waste gel loaded with zirconium" 2008 Bioresource Technol., 99(2008):8685-8690.
Bonnet, "Mechanistic Studies of Gd3+-Based MRI Contrast Agents for Zn2+ Detection: Towards Rational Design" 2014 Chem. Eur. J., 20(35):10959-10969.
Bonnet, "MRI probes for sensing biologically relevant metal ions. Future Med" 2010 Chem., 2(3):367-384.
Bonnet, "Smart MR imaging agents relevant to potential neurologic applications" 2010 AJNR Am. J. Neuroradiol., 31(3):401-9.
Botta, Second coordination sphere water molecules and relaxivity of gadolinium(III) complexes: Implications for MRI contrast agents. Eur. J. Inorg. Chem. 2000, 3, 399-407.
Bretonniere, "Design, synthesis and evaluation of ratiometric probes for hydrogencarbonate based on europium emission" 2004 Org. Biomol. Chem., 2(11):1624-1632.
Brewer, "Alzheimer's disease causation by copper toxicity and treatment with zinc" 2014 Front. Aging Neurosci., 6.
Brittain, "Inter-Molecular Energy-Transfer between Lanthanide Complexes in Aqueous-Solution .4 Stereoselectivity in the Transfer from Terbium(III) to Europium(III) Complexes of Aspartic-Acid" 1979 Inorg. Chem., 18(7):1740-1745.
Brittain, "Solution Phase Chemistry of Lanthanide Complexes .12. 1-1 and 1-2 Lanthanide Complexes with S-Carboxymethoxysuccinic Acid" 1991 J. Coord. Chem., 23(1-4):21-32.
Broome, "Nephrogenic systemic fibrosis associated with gadolinium based contrast agents: a summary of the medical literature reporting" 2008 Eur. J. Radiol., 66(2):230-4.
Bruce, "The selectivity of reversible oxy-anion binding in aqueous solution at a chiral europium and terbium center: Signaling of carbonate chelation by changes in the form and circular polarization of luminescence emission" 2000 J. Am. Chem. Soc., 122, 9674-9684.
Bunzli, "On the design of highly luminescent lanthanide complexes" 2015 Coord. Chem. Rev., 293, 19-47.
Bunzli, "Lanthanide coordination chemistry: from old concepts to coordination polymers" 2014 J. Coord. Chem., 67(23-24):3706-3733.
Bunzli, "Taking advantage of luminescent lanthanide ions" 2005 Chem. Soc. Rev., 34(12):1048-1077.
Burai, "Stability constants and H-1 relaxation effects of ternary complexes formed between Gd-DTPA, Gd-DTPA-BMA, Gd-DOTA, and Gd-EDTA and citrate, phosphate, and carbonate ions" 1997 Magn. Reson. Med., 38, 146-150.
Burdette, "ZP4, an improved neuronal Zn2+ sensor of the Zinpyr family" 2003 J. Am. Chem. Soc., 125(7):1778-87.
Bush, "Metals and neuroscience" 2000 Curr. Opin. Chem. Biol., 4(2):184-191.
Bush, "Therapeutics for Alzheimer's disease based on the metal hypothesis" 2008 Neurotherapeutics, 5(3):421-432.
Byegard, "The stability of some metal EDTA, DTPA and DOTA complexes: Application as tracers in groundwater studies" 1999 J. Radioanal. Nucl. Chem., 241(2):281-290.
Caravan, "Gadolinium(III) chelates as MRI contrast agents: Structure, dynamics, and applications" 1999 Chem. Rev., 99, 2293-2352.
Cardone, "The role of disturbed pH dynamics and the Na+/H+ exchanger in metastasis" 2005 Nat. Rev. Cancer, 5(10):786-795.
Chaudhum, "Ligand-based redox isomers of [Zn-II(C28H40NO2)2]: Molecular and electronic structures of a diamagnetic green and a paramagnetic red form" 1999 Inorg. Chem., 38(12):2781-2790.
Chen, "Sensitised near-infrared emission from lanthanides using an iridium complex as a ligand in heteronuclear Ir(2)Ln arrays" 2008 Dalton Trans.,(41):5577-5583.
Chen, "A selective fluorescence-on reaction of spiro form fluorescein hydrazide with Cu(II)" 2006 Anal. Chim. Acta 2006, 575(2):217-222.
Choi, Removal of Phosphate from Aqueous Solution by Functionalized Mesoporous Materials. Water Air Soil Pollut. 2011, 222(1-4):243-254.
Choi, "Zinc and brain injury" 1998 Annu. Rev. Neurosci., 21(1):347-375.
Chouyyok, "Phosphate Removal by Anion Binding on Functionalized Nanoporous Sorbents" 2010 Environ.Sci. Technol., 44(8):3073-3078.
Cody, "Fluorescence sensing based on cation-induced conformational switching: copper-selective modulation of the photoinduced intramolecular charge transfer of a donor-acceptor biphenyl fluorophore" 2004 Tetrahedron , 60(49):11099-11107.
Cohen, "Syntheses and relaxation properties of mixed gadolinium hydroxypyridinonate MRI contrast agents" 2000 Inorg. Chem., 39:5747-5756.

(56) References Cited

OTHER PUBLICATIONS

Comby, "New trick for an old ligand! The sensing of Zn(II) using a lanthanide based ternary Yb(III)-cyclen-8-hydroxyquinoline system as a dual emissive probe for displacement assay" 2012 Inorg. Chem., 51(19):10158-68.
Coppo, White-light emission from an assembly comprising luminescent iridium and europium complexes. Angew. Chem. Int. Ed. 2005, 44(12):1806-1810.
Cordell, "The story of phosphorus: Global food security and food for thought" 2009 Global Environ. Chang., 19, 292-305.
Corsi, "Determination of paramagnetic lanthanide(III) concentrations from bulk magnetic susceptibility shifts in NMR spectra" 2001 Mag. Reson. Chem., 39(11):723-726.
Crouch, "The Alzheimer's therapeutic PBT2 promotes amyloid-beta degradation and GSK3 phosphorylation via a metal chaperone activity" 2011 J. Neurochem., 119(1):220-230.
Dagdigian, "Structural comparison of a redox pair of copper(I/II) complexes having benzimidazole thioether ligands" 1982 Inorg. Chem. , 21(4):1332-1342.
Datta, "Chemical Hardness, Heterolytic Dissociative Version of Pauling Bond-Energy Equation and a Novel-Approach Towards Understanding Pearson Hard-Soft Acid-Base Principle" 1991 J. Chem. Soc., Dalton Trans.,(6):1541-1549.
De Leon-Rodriguez, "A second generation MRI contrast agent for imaging zinc ions in vivo" 2012 Med.Chem. Commun., 3(4):480-483.
De Leon-Rodriguez, "Imaging free zinc levels in vivo—what can be learned?" 2012 Inorg. Chim. Acta, 393, 12-23.
De-Bashan, Recent advances in removing phosphorus from wastewater and its future use as fertilizer(1997-2003). Water Res. 2004, 38, 4222-4246.
Deibel, "Copper, iron, and zinc imbalances in severely degenerated brain regions in Alzheimer's disease: Possible relation to oxidative stress" 1996 J. Neurol. Sci., 143(1-2):137-142.
Delli Castelli, "In vivo maps of extracellular pH in murine melanoma by CEST-MRI" 2014 Mag. Reson. Med., 71(1):326-332.
Desilva, "A fluorescent photoinduced electron transfer sensor for cations with an off-on-off proton switch" 1997 Tetrahedron Lett. 1997, 38(13):2237-2240.
Dexter, "A Theory of Sensitized Luminescence in Solids" 1953 J. Chem. Phys., 21(5):836-850.
Dickins, "Reversible anion binding in aqueous solution at a cationic heptacoordinate lanthanide centre: selective bicarbonate sensing by time-delayed luminescence" 1998 Chem. Commun.,(16):1643-1644.
Dickins, "Closely diffusing O—H, amide N—H and methylene C—H oscillators quench the excited state of europium comlexes in solution" 1996 Chem. Commun., (6):697-698.
Dixon, "A concentration-independent method to measure exchange rates in PARACEST agents" 2010 Magn. Reson.Med., 63(3):625-632.
Djanashvili, "How to determine the number of inner-sphere water molecules in lanthanide(III) complexes by O-17 NMR spectroscopy. A technical note" 2007 Contrast Media Mol. Imaging, 2(2):67-71.
Dodani, A Targetable Fluorescent Sensor Reveals That Copper-Deficient SCO1 and SCO2 Patient Cells Prioritize Mitochondrial Copper Homeostasis. J. Am. Chem. Soc. 2011, 133(22):8606-8616.
Doerrer, "Zinc and cadmium tropocoronand complexes: Effect of metal ion radius on macrocyclic ligand twist and fold" 1997 Inorg. Chem., 36(12):2554-2563.
Domaille, "Synthetic fluorescent sensors for studying the cell biology of metals" 2008 Nat. Chem. Biol., 4(3):168-175.
Donatello, Recycling and recovery routes for incinerated sewage sludge ash(ISSA): A review. Waste Manage. 2013, 33(11):2328-2340.
Dos Santos, "Lanthanide luminescent anion sensing: evidence of multiple anion recognition through hydrogen bonding and metal ion coordination" 2007 Chem. Commun., 3389-3391.
Dos Santos, "The recognition of anions using delayed lanthanide luminescence: The use of Tb(III) based urea functionalised cyclen complexes" 2009 Dalton Trans.,(24):4712-4721.
Du, "A Highly Selective Turn-On Colorimetric, Red Fluorescent Sensor for Detecting Mobile Zinc in Living Cells" 2010 Inorg. Chem., 49(23):10753-10755.
Dujols, "A long-wavelength fluorescent chemodosimeter selective for Cu(II) ion in water" 1997 J. Am. Chem. Soc., 119(31):7386-7387.
Elbanowski, "The lanthanides as luminescent probes in investigations of biochemical systems" 1996 J. Photochem. Photobiol. A, 99(2-3):85-92.
Eliseeva, "Lanthanide luminescence for functional materials and bio-sciences" 2010 Chem. Soc. Rev., 39(1):189-227.
Engblom, "The phosphate sensor" 1998 Biosens. Bioelectron., 13(9):981-994.
Epa, Ed. "Quality Criteria for Water, 1986" 1986 Office of Water Regulations and Standards: Washington, DC.
Esqueda, "A New Gadolinium-Based MRI Zinc Sensor" 2009 J. Am. Chem. Soc., 131(32):11387-11391.
Evans, "Perspectives in reductive lanthanide chemistry" 2000 Coord. Chem. Rev. 2000, 206, 263-283.
Evbuomwan, "Amphiphilic EuDOTA-Tetraamide Complexes Form Micelles with Enhanced CEST Sensitivity" 2012 Eur. J. Inorg. Chem.,(12):2126-2134.
Fabbrizzi, "An Anthracene-Based Fluorescent Sensor for Transition-Metal Ions" 1994 Angew. Chem. Int. Ed., 33(19):1975-1977.
Fabbrizzi, "Fluorescent sensors for transition metals based on electron-transfer and energy-transfer mechanisms" 1996 Chem. Eur. J., 2(1):75-82.
Faulkner, "Lanthanide-sensitized lanthanide luminescence: Terbium-sensitized ytterbium luminescence in a trinuclear complex" 2003 J. Am. Chem. Soc., 125(35):10526-10527.
Fernandez-Cornejo/USDA, "Pesticide Use in U.S. Agriculture: 21 Selected Crops, 1960-2008" May 2014 U.S. Department of Agriculture, Economic Research Service Washington, DC, USA.
Frederickson, "A Quinoline Fluorescence Method for Visualizing and Assaying the Histochemically Reactive Zinc(Bouton Zinc) in the Brain" 1987 J. Neurosci. Methods, 20(2):91-103.
Frederickson, "The neurobiology of zinc in health and disease" 2005 Nat. Rev. Neurosci., 6(6):449-462.
Freed, "Dynamic Effects of Pair Correlation-Functions on Spin Relaxation by Translational Diffusion in Liquids .II. Finite Jumps and Independent T1 Processes" 1978 J.Chem. Phys., 68(9):4034-4037.
Freedonia Focus Reports "Membrane Separation Technologies: US" 2015. 1 pg.
Fryxell, "Design and synthesis of selective mesoporous anion traps" 1999 Chem. Mater., 11(8):2148-2154.
Fujisawa, "Mononuclear and binuclear copper(I) complexes ligated by bis(3,5-diisopropyl-1-pyrazolyl)methane: insight into the fundamental coordination chemistry of three-coordinate copper(I) complexes with a neutral coligand" 2007 Inorg. Chem., 46(25):10607-23.
Funk, "Critical analysis of the limitations of Bleaney's theory of magnetic anisotropy in paramagnetic lanthanide coordination complexes" 2015 Chem. Sci., 6(3):1655-1662.
Gaggelli, "Copper homeostasis and neurodegenerative disXs(Alzheimer's, prion, and Parkinson's diseases and amyotrophic lateral sclerosis)" 2006 Chem. Rev. 2006, 106(6):1995-2044.
Gerber, "Zinc and Copper Differentially Modulate Amyloid Precursor Protein Processing by gamma-Secretase and Amyloid-beta Peptide Production" 2017 J. Biol. Chem.
Getz, "Luminescence resonance energy transfer measurements in myosin" 1998 Biophys. J., 74(5):2451-2458.
Ghiladi, "Synthesis and Characterization of New Trinuclear Copper Complexes" 2012 Inorg. Chim. Acta, 389, 131-137.
Ghosh, "Ni(II):Cu(II):and Zn(II) cryptate-enhanced fluorescence of a trianthrylcryptand: A potential molecular photonic OR operator" 1996 J. Am. Chem. Soc., 118(6):1553-1554.

(56) References Cited

OTHER PUBLICATIONS

Giansante, "Self-assembly of a light-harvesting antenna formed by a dendrimer, a Ru-II complex, and a Nd-III ion" 2008 Angew. Chem. Int. Ed., 47(29):5422-5425.

Gillies, "MRI of the tumor microenvironment" 2002 J. Magn. Reson. Imaging, 16(4):430-450.

Goldberg, "Determination of Cu, Mn, Fe, and Ca in six regions of normal human brain, by atomic absorption spectroscopy" 1981 Clin. Chem., 27(4):562-4.

Green, "Europium(III) DOTA-Derivatives Having Ketone Donor Pendant Arms Display Dramatically Slower Water Exchange" 2011 Inorg. Chem., 50(5):1648-1655.

Grell, "Molecular ionics of anion receptor molecules—A microcalorimetric study" 2004 *J. Therm. Anal. Calorim.*, 77:483-495.

Grotenbreg, "Synthesis and biological evaluation of gramicidin S dimers" Abstract 2005 *Organic & Biomolecular Chemistry*. Online: https://pubs.rsc.org/en/content/articlelanding/2005/ob/b414618b#!divAbstract Accessed: Mar. 22, 2019. 5 pgs.

Gunnlaugsson, "Eu(III)-cyclen-phen conjugate as a luminescent copper sensor: the formation of mixed polymetallic macrocyclic complexes in water" 2004 Chem. Commun. 2004,(7):782-783.

Gysling, "Organolanthanides and Organoactinides" in *Adv. Org. Chem.* vol. 9. Stone; Academic Press: 1971; Cover page, title page, table of contents, pp. 361-395.

Haas, "Application of Metal Coordination Chemistry to Explore and Manipulate Cell Biology" 2009 Chem. Rev., 109(10):4921-4960.

Halliwell, "Role of free radicals in the neurodegenerative diseases—Therapeutic implications for antioxidant treatment" 2001 Drugs Aging, 18(9):685-716.

Han, "Naked-eye detection of phosphate ions in water at physiological pH: A remarkably selective and easy-to-assemble colorimetric phosphate-sensing probe" 2002 *Angew. Chem. Int. Ed.*, 41:3809-3811.

Hanaoka, "Development of a zinc ion-selective luminescent lanthanide chemosensor for biological applications" 2004 *J. Am. Chem. Soc.*, 126(39):12470-6.

Hanaoka, "Selective detection of zinc ions with novel luminescent lanthanide probes" 2003 Angew. Chem. Int. Ed., 42(26):2996-2999.

Hanaoka, "Selective sensing of zinc ions with a novel magnetic resonance imaging contrast agent" 2001 J. Chem. Soc. Perkin Trans. 2,(9): 1840-1843.

Hanaoka, "Design and synthesis of a novel magnetic resonance imaging contrast agent for selective sensing of zinc ion" 2002 Chem. Biol., 9(9):1027-1032.

Hancock, "Ligand Design for Selective Complexation of Metal-Ions in Aqueous-Solution" 1989 *Chem. Rev.*, 89:1875-1914.

Harris, "Recognition of Cations and Anions by Lanthanide Complexes" Thesis, University of Minnesota, Jul. 2017. 197 pgs.

Pierre in USDA NSF "Innovations at the Nexus of Food, Energy, and Water Systems (INFEWS) 2017 Principal Invesitgator Workshop" Mar. 22-24, 2017, Arlington, VA. 9 pgs.

\* cited by examiner

COMPOSITIONS, METHODS, AND DEVICES FOR CAPTURING PHOSPHATE FROM WATER

CROSS-REFERENCE TO RELATED APPLICATIONS

This application claims the benefit of U.S. Provisional Application Ser. No. 62/475,356, filed Mar. 23, 2017, which is incorporated by reference herein.

GOVERNMENT FUNDING

This invention was made with government support under CHE-1610832 awarded by the National Science Foundation. The government has certain rights in the invention.

SUMMARY

The present disclosure provides compositions, methods, and devices for sensing, detecting, and/or selectively capturing phosphate from water.

In one aspect, the present disclosure provides a method for sensing, detecting, and/or selectively capturing phosphate from water.

In one embodiment, the method includes: contacting a ligand or a rare earth metal complex of the ligand with an aqueous phosphate-containing medium at a pH of 5 to 12 under conditions sufficient to bind phosphate, wherein the ligand is selected from the group consisting of

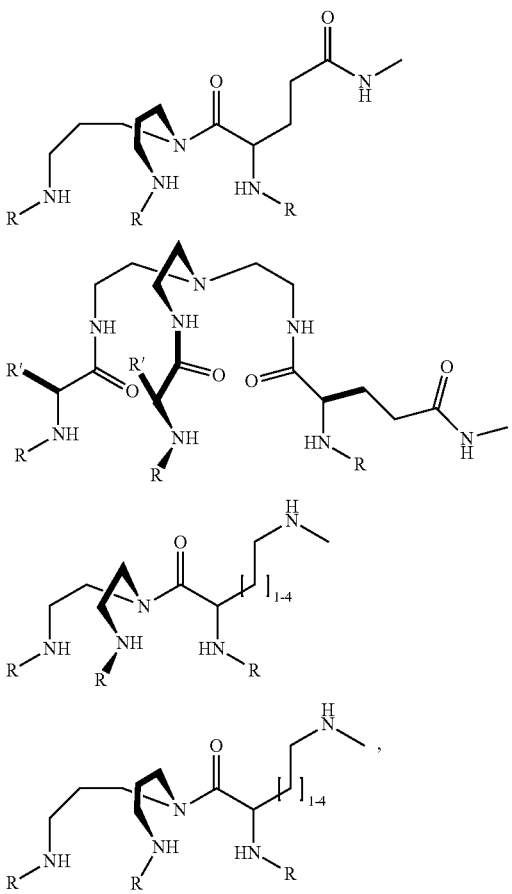

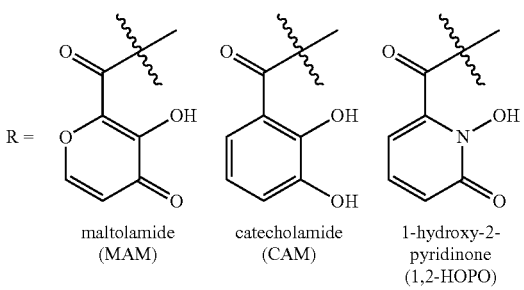

and combinations thereof; wherein R is selected from the group consisting of

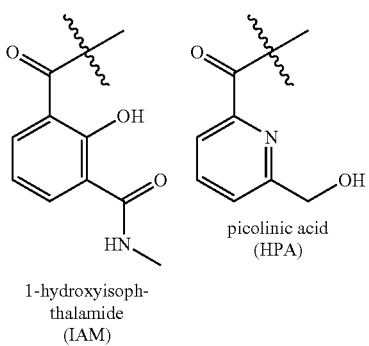

-continued

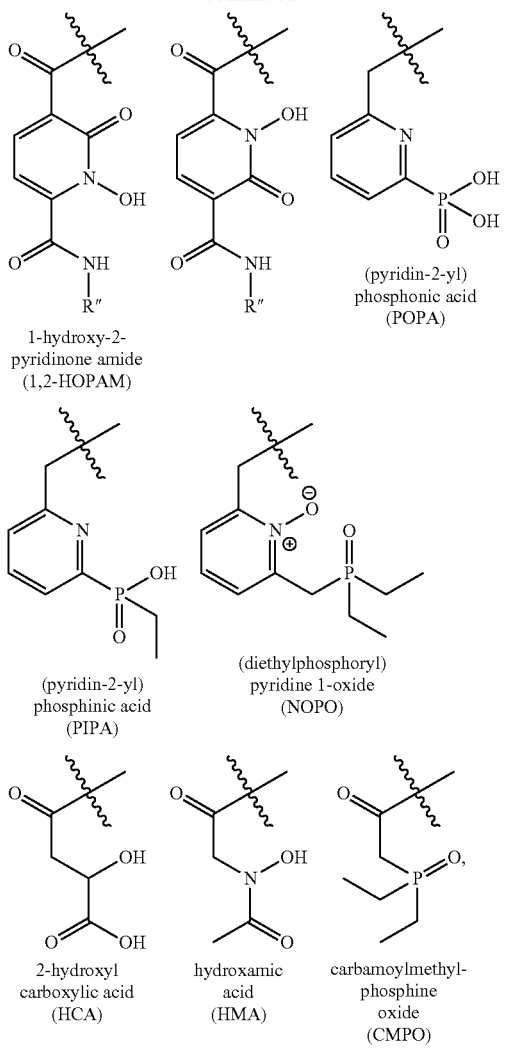

and combinations thereof; wherein R' is selected from the group consisting of

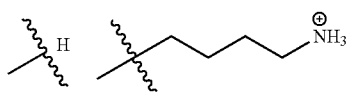

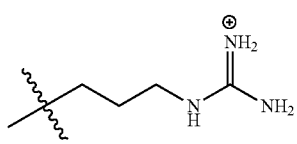

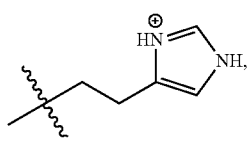

and combinations thereof; wherein R" is selected from the group consisting of

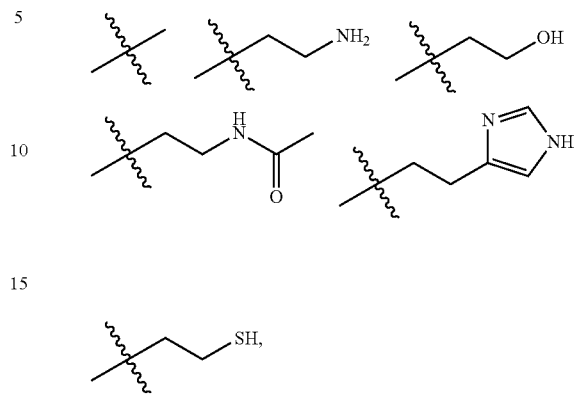

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof. In certain embodiments, the ligand or the rare earth metal complex of the ligand reversibly binds the phosphate. In certain embodiments, the method further includes releasing the bound phosphate by contacting the bound phosphate complex with an aqueous medium at a pH of 0 to 4 under conditions sufficient to release the bound phosphate.

In another aspect, the present disclosure provides a ligand or a rare earth metal complex of the ligand that can be useful for sensing, detecting, and/or selectively capturing phosphate from water.

In one embodiment, the present disclosure provides a ligand or a rare earth metal complex of the ligand, wherein the ligand is of the formula:

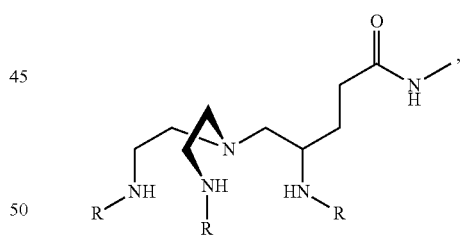

wherein R is selected from the group consisting of

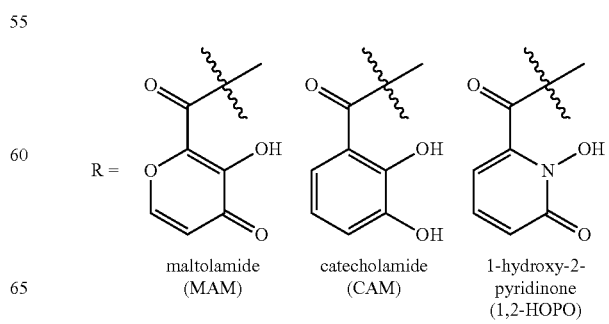

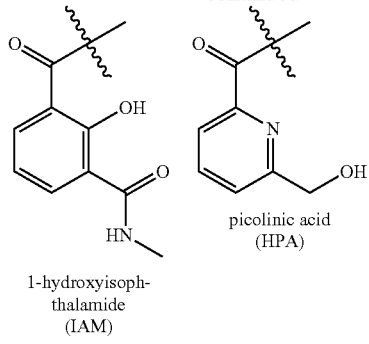

1-hydroxyisoph-
thalamide
(IAM)

picolinic acid
(HPA)

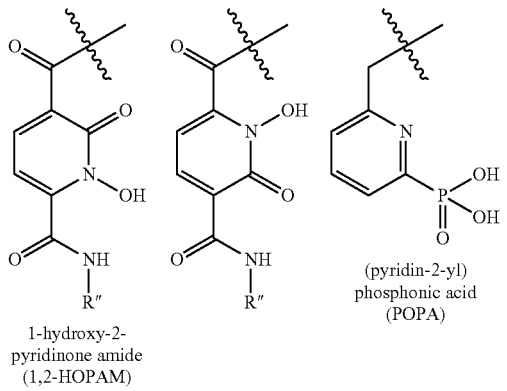

1-hydroxy-2-
pyridinone amide
(1,2-HOPAM)

(pyridin-2-yl)
phosphonic acid
(POPA)

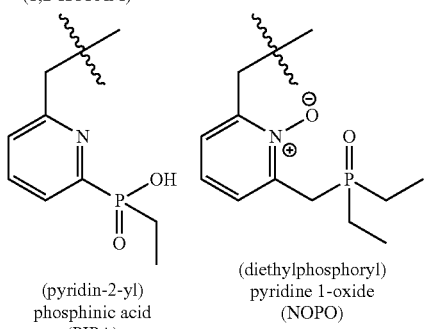

(pyridin-2-yl)
phosphinic acid
(PIPA)

(diethylphosphoryl)
pyridine 1-oxide
(NOPO)

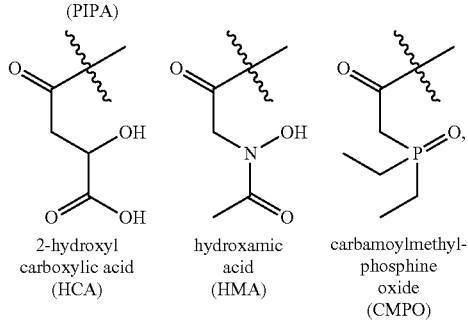

2-hydroxyl
carboxylic acid
(HCA)

hydroxamic
acid
(HMA)

carbamoylmethyl-
phosphine
oxide
(CMPO)

and combinations thereof; wherein R" is selected from the group consisting of

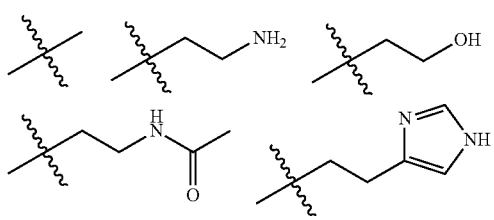

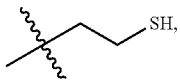

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

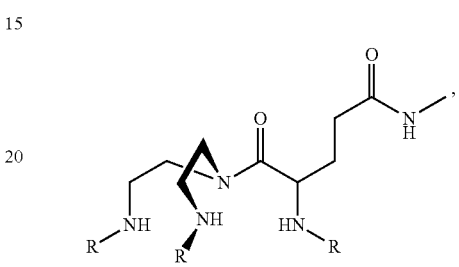

wherein R is selected from the group consisting of

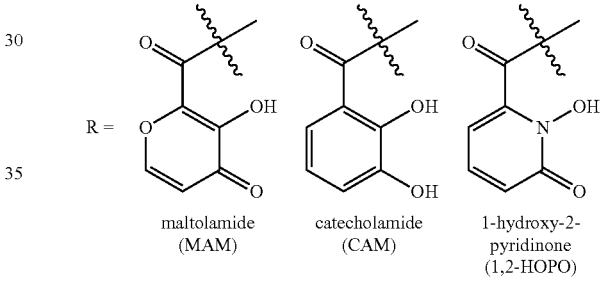

maltolamide
(MAM)

catecholamide
(CAM)

1-hydroxy-2-
pyridinone
(1,2-HOPO)

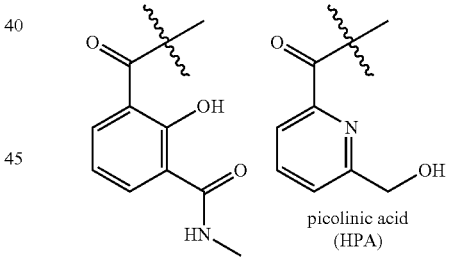

1-hydroxyisoph-
thalamide
(IAM)

picolinic acid
(HPA)

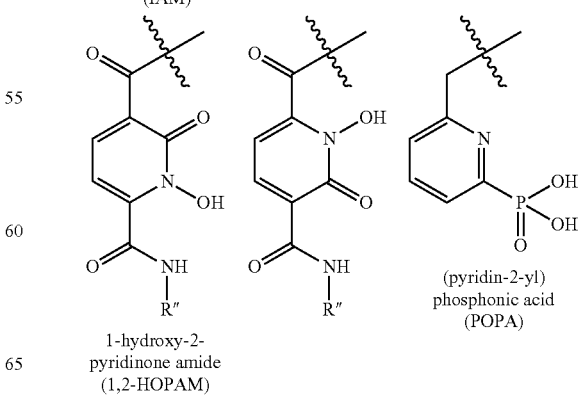

1-hydroxy-2-
pyridinone amide
(1,2-HOPAM)

(pyridin-2-yl)
phosphonic acid
(POPA)

-continued

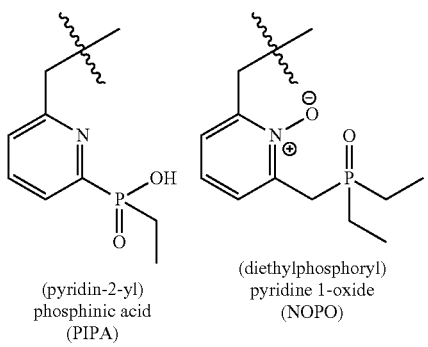

(pyridin-2-yl) phosphinic acid (PIPA)

(diethylphosphoryl) pyridine 1-oxide (NOPO)

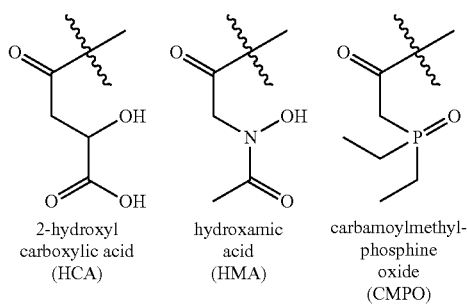

2-hydroxyl carboxylic acid (HCA)

hydroxamic acid (HMA)

carbamoylmethyl- phosphine oxide (CMPO)

and combinations thereof; wherein R" is selected from the group consisting of

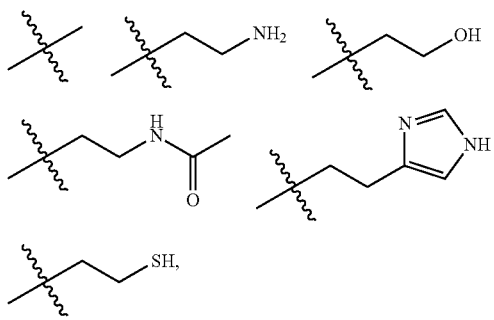

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

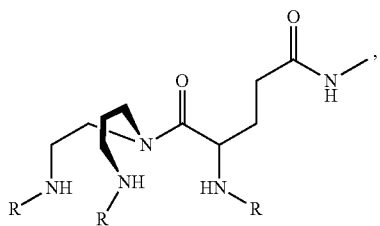

wherein R is selected from the group consisting of

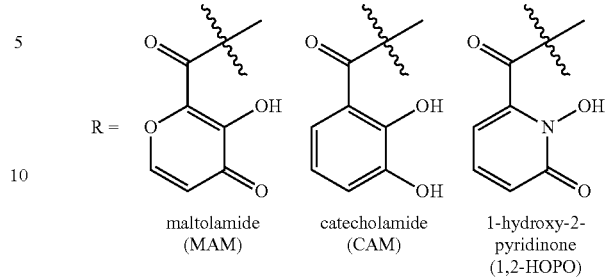

R = maltolamide (MAM)

catecholamide (CAM)

1-hydroxy-2- pyridinone (1,2-HOPO)

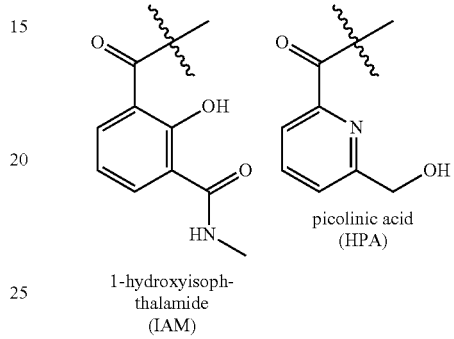

1-hydroxyisoph- thalamide (IAM)

picolinic acid (HPA)

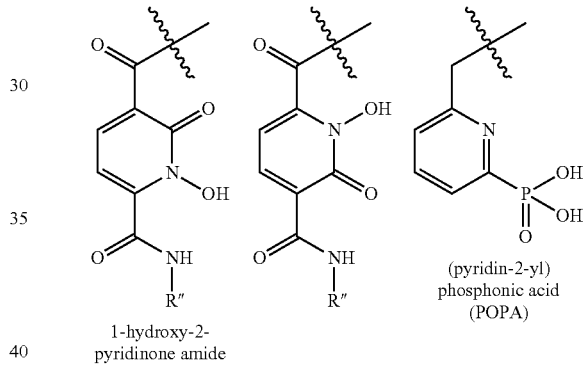

1-hydroxy-2- pyridinone amide (1,2-HOPAM)

(pyridin-2-yl) phosphonic acid (POPA)

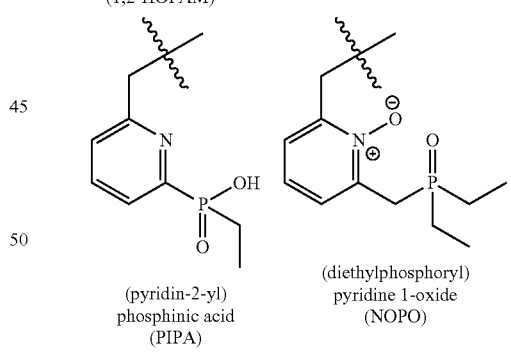

(pyridin-2-yl) phosphinic acid (PIPA)

(diethylphosphoryl) pyridine 1-oxide (NOPO)

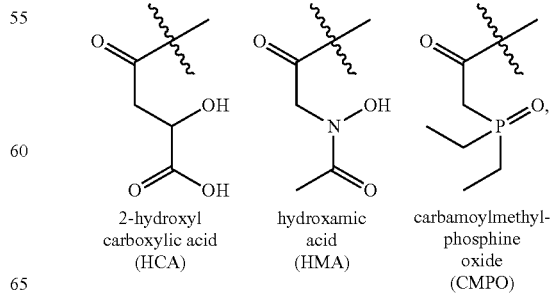

2-hydroxyl carboxylic acid (HCA)

hydroxamic acid (HMA)

carbamoylmethyl- phosphine oxide (CMPO)

and combinations thereof; wherein R" is selected from the group consisting of

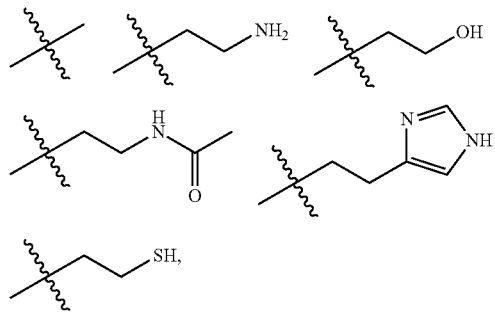

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

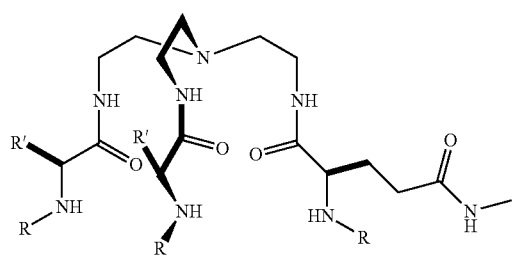

wherein R is selected from the group consisting of

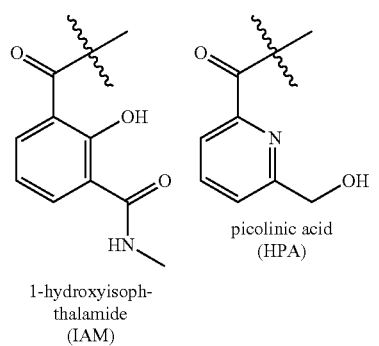

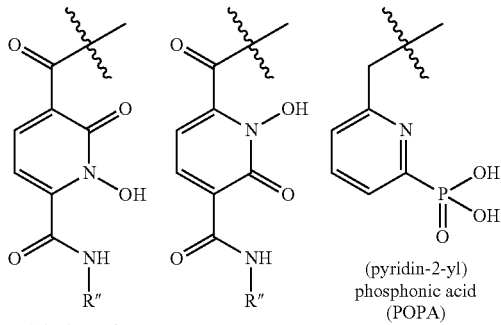

(pyridin-2-yl) phosphonic acid (POPA)

1-hydroxy-2-pyridinone amide (1,2-HOPAM)

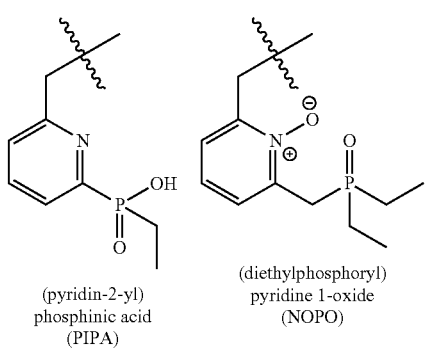

(pyridin-2-yl) phosphinic acid (PIPA)

(diethylphosphoryl) pyridine 1-oxide (NOPO)

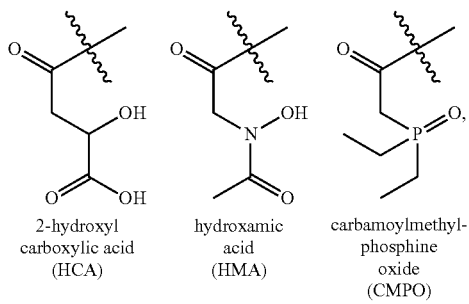

2-hydroxyl carboxylic acid (HCA)

hydroxamic acid (HMA)

carbamoylmethyl-phosphine oxide (CMPO)

and combinations thereof; wherein R' is selected from the group consisting of

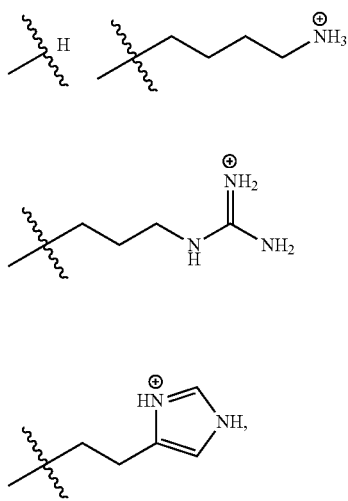

and combinations thereof;

and combinations thereof; wherein R″ is selected from the group consisting of

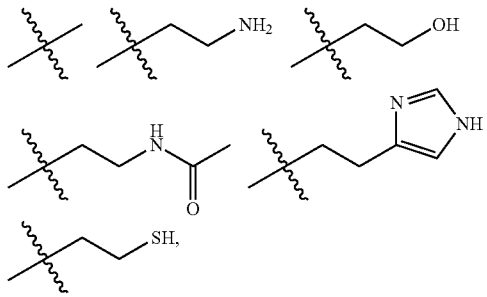

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

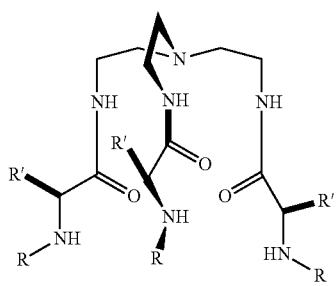

wherein R is selected from the group consisting of

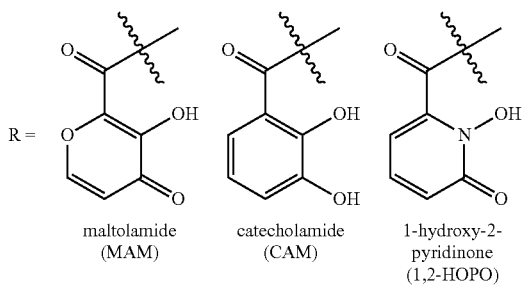

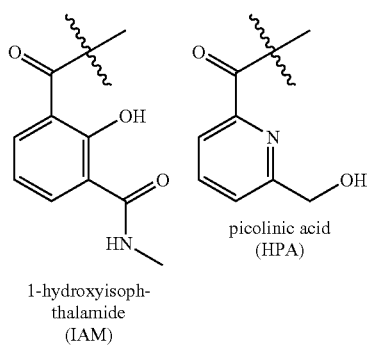

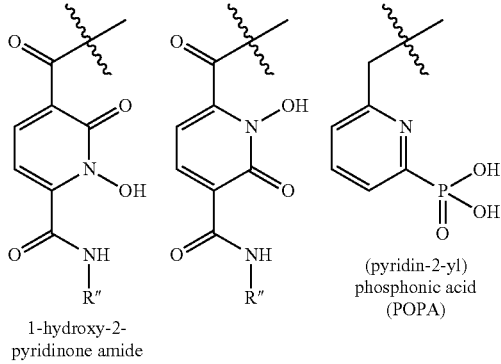

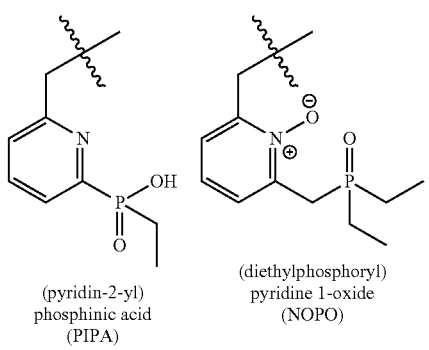

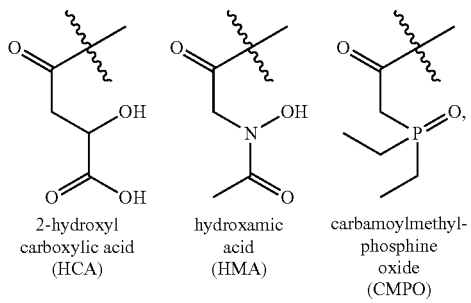

and combinations thereof; wherein R′ is selected from the group consisting of

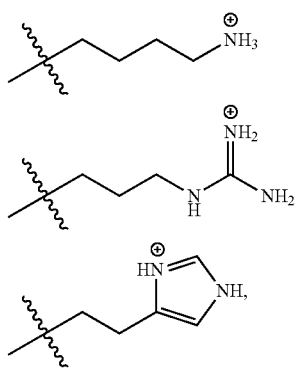

and combinations thereof; wherein R" is selected from the group consisting of

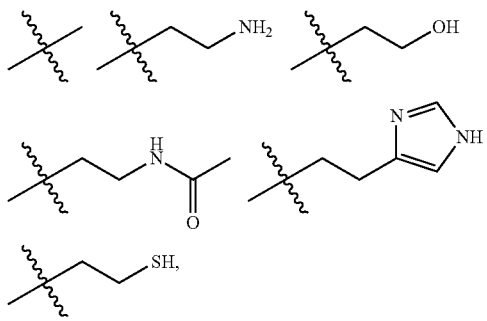

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

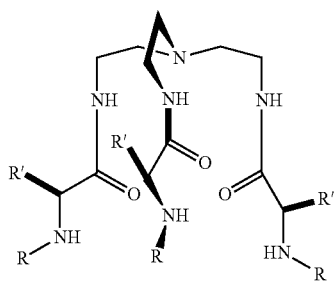

wherein R is selected from the group consisting of

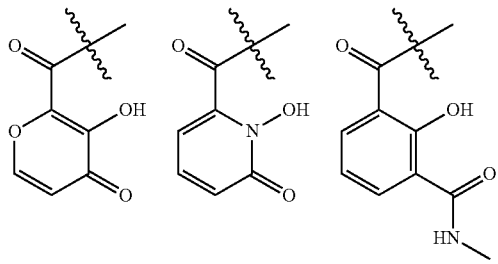

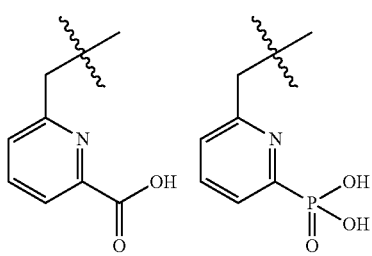

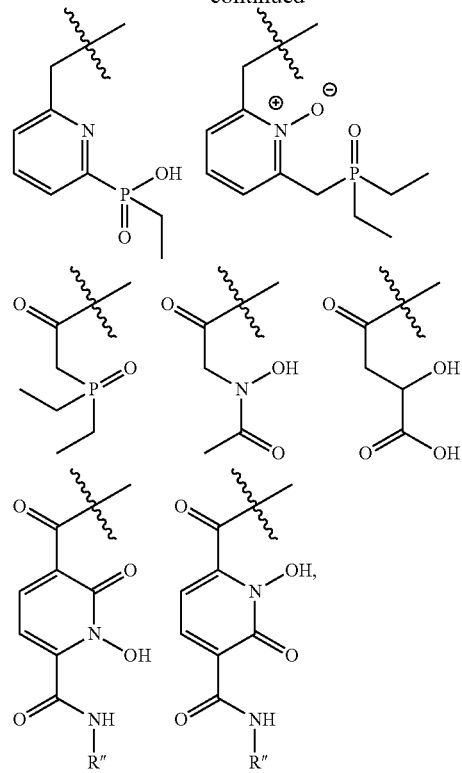

and combinations thereof; wherein R' is selected from the group consisting of

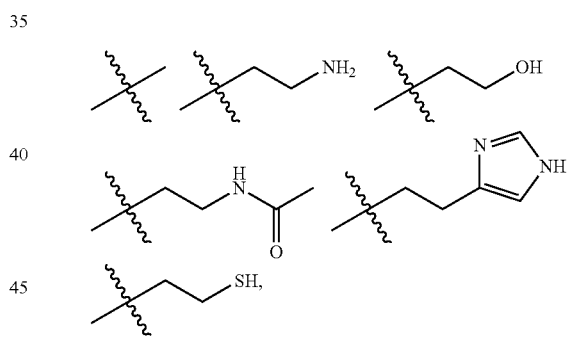

and combinations thereof; wherein R" is selected from the group consisting of

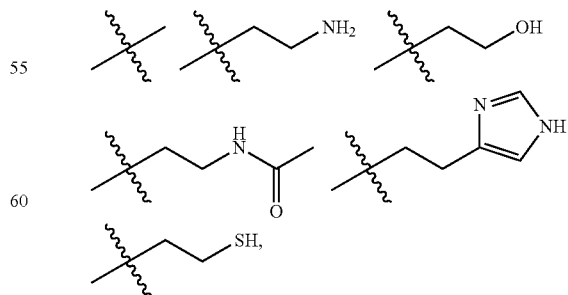

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a rare earth metal complex of a ligand of the formula:

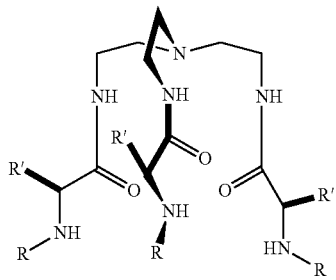

wherein R is

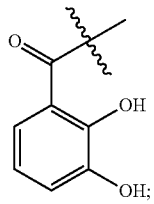

wherein R' is

and wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In another embodiment, the present disclosure provides a ligand or a rare earth metal complex of the ligand, wherein the ligand is of the formula:

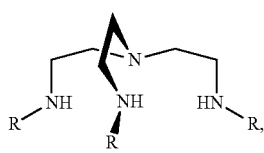

wherein R is selected from the group consisting of

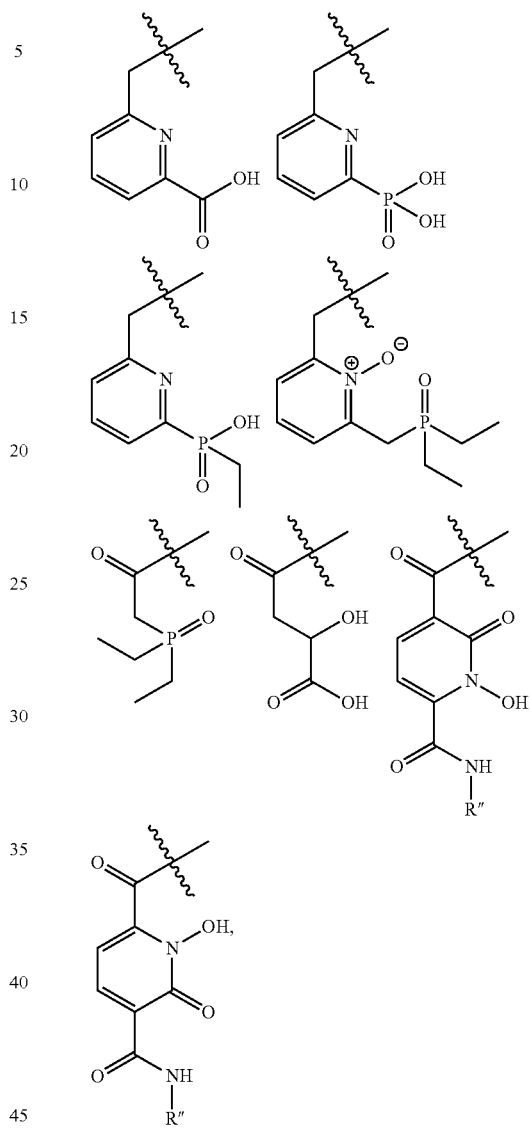

and combinations thereof; wherein R" is selected from the group consisting of

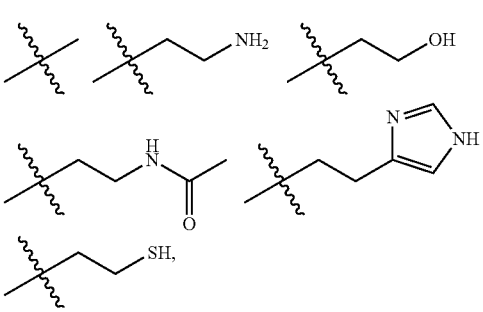

and combinations thereof; and wherein optionally the rare earth metal of the rare earth metal complex of one or more of the ligands is selected from the group consisting of $Y^{3+}$, La$^{3+}$, Ce$^{3+}$, Pr$^{3+}$, Nd$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, Lu$^{3+}$, and combinations thereof.

In another embodiment, the present disclosure provides a rare earth metal complex of a ligand of the formula:

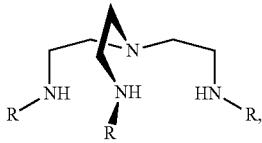

wherein R is selected from the group consisting of

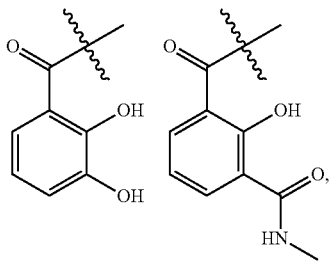

and combinations thereof; and wherein the rare earth metal of the rare earth metal complex of one or more of the ligands is selected from the group consisting of Y$^{3+}$, La$^{3+}$, Ce$^{3+}$, Pr$^{3+}$, Nd$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, Lu$^{3+}$, and combinations thereof.

In another embodiment, the present disclosure provides a rare earth metal complex of a ligand of the formula:

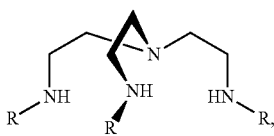

wherein R is selected from the group consisting of

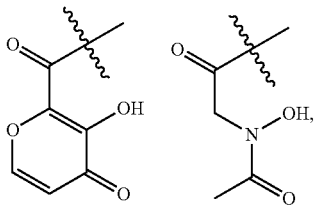

and combinations thereof and wherein the rare earth metal of the rare earth metal complex of one or more of the ligands is selected from the group consisting of Y$^{3+}$, La$^{3+}$, Ce$^{3+}$, Pr$^{3+}$, Nd$^{3+}$, Sm$^{3+}$, Eu$^{3+}$, Tb$^{3+}$, Dy$^{3+}$, Ho$^{3+}$, Er$^{3+}$, Tm$^{3+}$, Yb$^{3+}$, Lu$^{3+}$, and combinations thereof.

In another embodiment, the present disclosure provides a rare earth metal complex of a ligand of the formula:

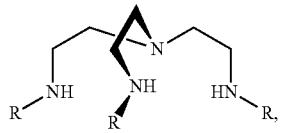

wherein R is

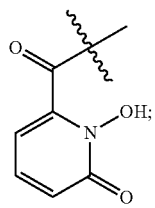 [SMILES: *C(=O)c1cccc(=O)n1O]

and wherein the rare earth metal of the rare earth metal complex of one or more of the ligands is selected from the group consisting of Y$^{3+}$, La$^{3+}$, Ce$^{3+}$, Pr$^{3+}$, Nd$^{3+}$, Sm$^{3+}$, Tb$^{3+}$, Dy$^{3+}$, Ho$^{3+}$, Er$^{3+}$, Tm$^{3+}$, Yb$^{3+}$, Lu$^{3+}$, and combinations thereof.

In another aspect, the present disclosure provides another method for sensing, detecting, and/or selectively capturing phosphate from water.

In one embodiment, the method includes: contacting a ligand or a rare earth metal complex of a ligand as described herein with an aqueous phosphate-containing medium at a pH of 5 to 12 under conditions sufficient to bind phosphate. In certain embodiments, the ligand or the rare earth metal complex of the ligand reversibly binds the phosphate. In certain embodiments, the method further includes releasing the bound phosphate by contacting the bound phosphate complex with an aqueous medium at a pH of 0 to 4 under conditions sufficient to release the bound phosphate.

In another aspect, the present disclosure provides a device for sensing, detecting, and/or selectively capturing phosphate from water having a ligand or a rare earth metal complex of the ligand attached thereto.

In one embodiment, the device for sensing, detecting, and/or selectively capturing phosphate from water in which a ligand or a rare earth metal complex of the ligand is attached thereto, the ligand is selected from the group consisting of

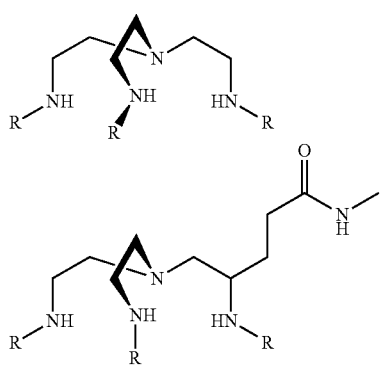

-continued
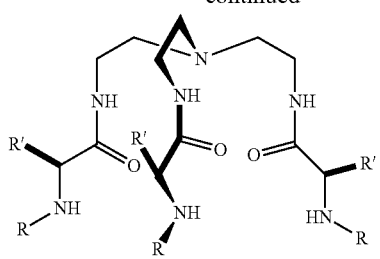
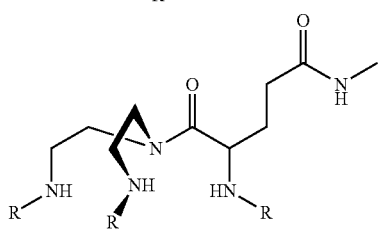
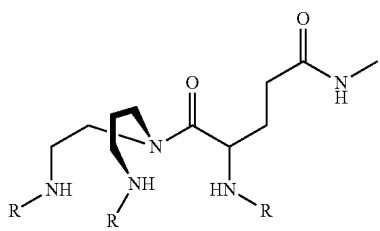
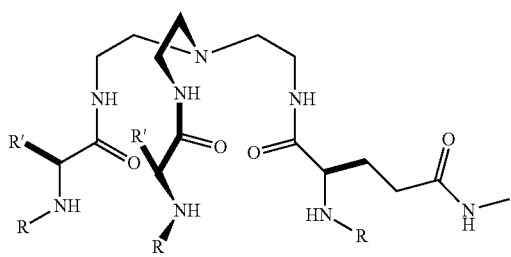
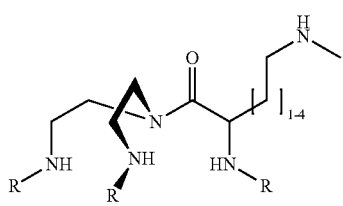
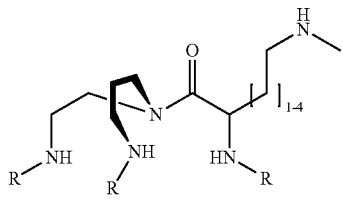
and combinations thereof; R is selected from the group consisting of
R =
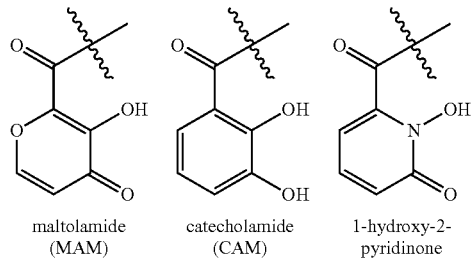
maltolamide (MAM)  catecholamide (CAM)  1-hydroxy-2-pyridinone (1,2-HOPO)
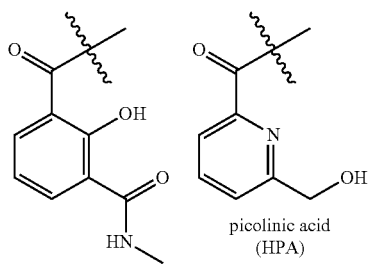
1-hydroxyisoph-thalamide (IAM)  picolinic acid (HPA)
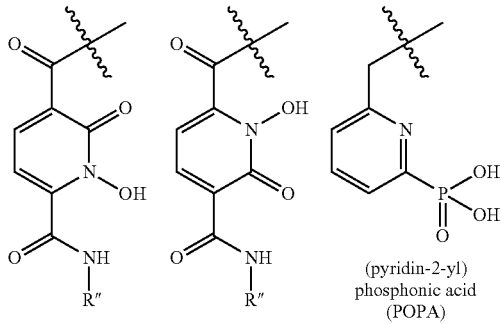
1-hydroxy-2-pyridinone amide (1,2-HOPAM)  (pyridin-2-yl) phosphonic acid (POPA)
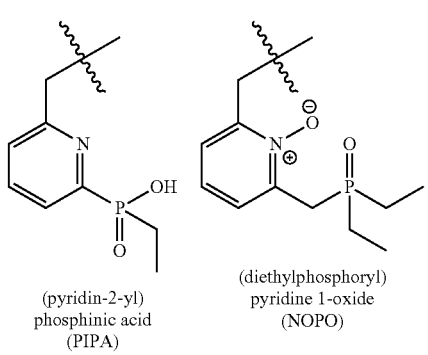
(pyridin-2-yl) phosphinic acid (PIPA)  (diethylphosphoryl) pyridine 1-oxide (NOPO)

-continued

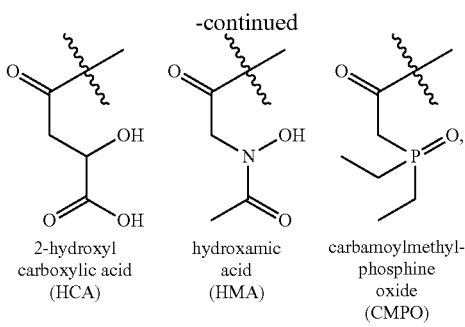

2-hydroxyl carboxylic acid (HCA)

hydroxamic acid (HMA)

carbamoylmethyl-phosphine oxide (CMPO)

and combinations thereof; R' is selected from the group consisting of

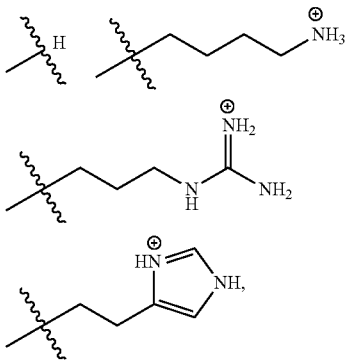

and combinations thereof; R" is selected from the group consisting of

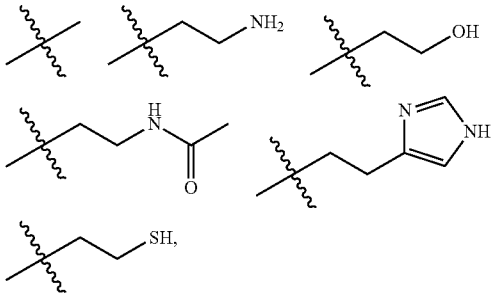

and combinations thereof; and the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

In certain embodiments, the device includes a membrane having the ligand or the rare earth metal complex of the ligand attached thereto. In certain embodiments, the device includes a sensor or detector having the ligand or the rare earth metal complex of the ligand attached thereto. In certain embodiments, the ligand can be chemically attached to a surface of the device (e.g., a surface of the membrane) through covalent and/or ionic bonding using a variety of methods that would be available to one of skill in the art. In certain embodiments, the ligand can include a pendent functional group (e.g., a N, O, P, and/or S-containing group) that can function as a linker to chemically attach the ligand to a surface of the device.

In another aspect, the present disclosure provides another method for sensing, detecting, and/or selectively capturing phosphate from water.

In one embodiment, the method includes: contacting a device as disclosed herein with an aqueous phosphate-containing medium at a pH of 5 to 12 under conditions sufficient to bind phosphate. In certain embodiments, the device reversibly binds the phosphate. In certain embodiments, the method further includes releasing the bound phosphate by contacting the bound phosphate complex with an aqueous medium at a pH of 0 to 12 under conditions sufficient to release the bound phosphate.

The above brief description of various embodiments of the present invention is not intended to describe each embodiment or every implementation of the present invention. Rather, a more complete understanding of the invention will become apparent and appreciated by reference to the following description and claims. Further, it is to be understood that other embodiments may be utilized and structural changes may be made without departing from the scope of the present invention.

DETAILED DESCRIPTION OF ILLUSTRATIVE EMBODIMENTS

Figure 1:
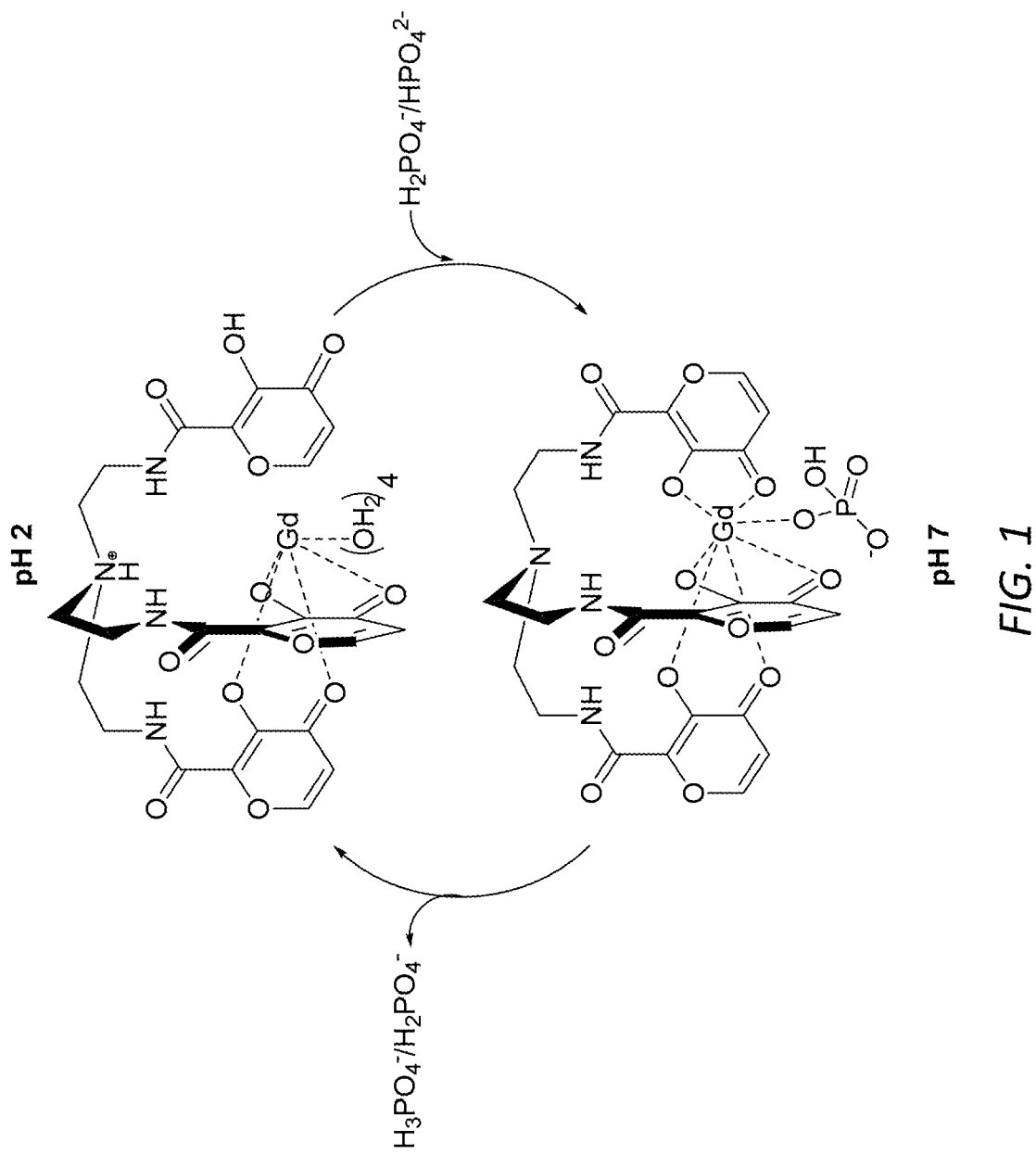
FIG. 1 is the pH dependent recycling scheme for catch-and-release of phosphate by Gd-TREN-MAM.

The description that follows is not intended to describe each disclosed embodiment or every implementation of the present disclosure. In several places throughout the application, guidance is provided through lists of examples, which examples can be used in various combinations. In each instance, the recited list serves only as a representative group and should not be interpreted as an exclusive list.

Disclosed herein are ligands and rare earth metal complexes of such ligands, where the ligand has the formula

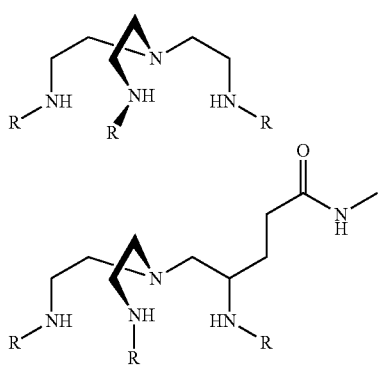

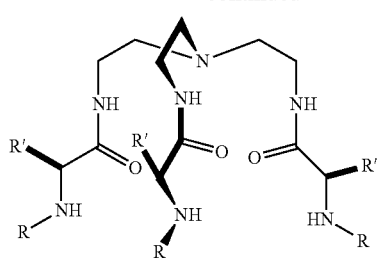

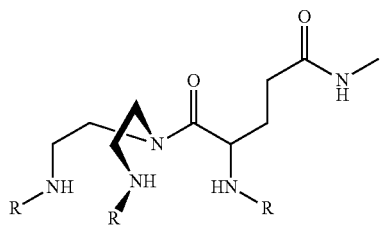

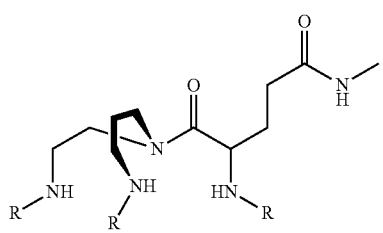

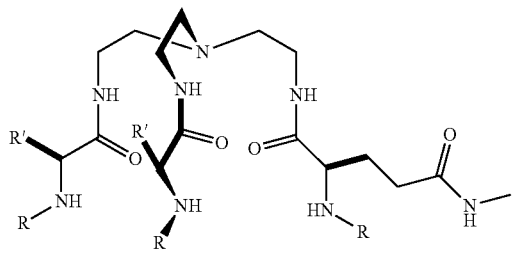

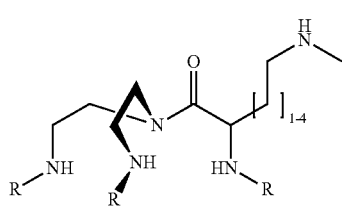

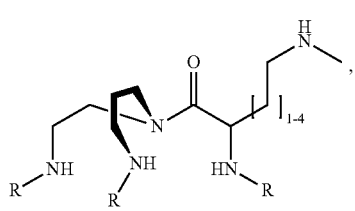

and combinations thereof; wherein R is selected from the group consisting of

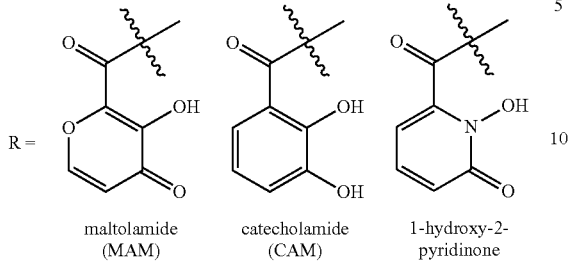

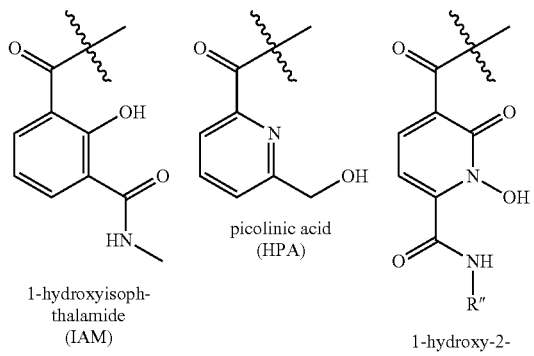

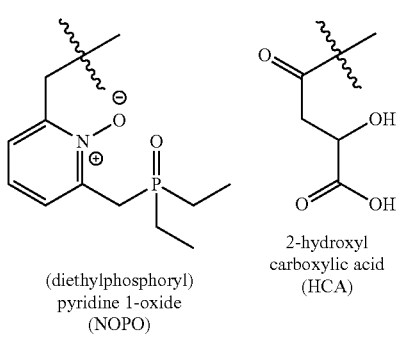

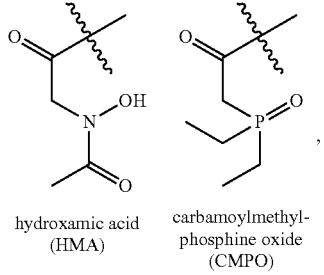

and combinations thereof; wherein R' is selected from the group consisting of

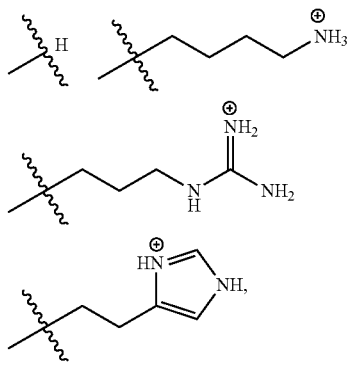

and combinations thereof; wherein R" is selected from the group consisting of

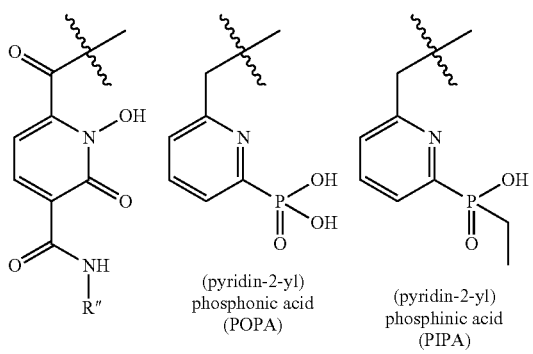

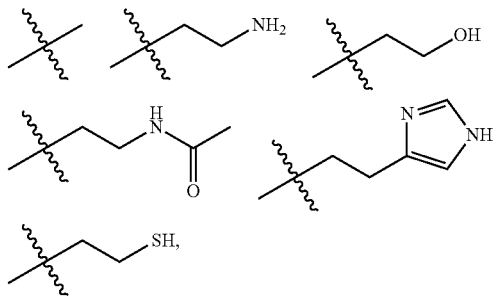

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof. In certain embodiments, the ligand or the rare earth metal complex of the ligand reversibly binds the phosphate.

Methods and devices including such ligands and rare earth metal complexes including such ligands are also disclosed herein. In certain embodiments, the methods can further include releasing bound phosphate by contacting the bound phosphate complex with an aqueous medium at a pH of 0 to 4 under conditions sufficient to release the bound phosphate.

The ability of complexes of hard and labile metal ions with one or more open coordination site to capture phosphates with high affinity and selectivity directly in water at neutral pH and release them under acidic conditions is evaluated with Gd-TREN-MAM. This model lanthanide complex has two open coordination sites that at neutral pH are filled with water molecules. In water at neutral pH, Gd-TREN-MAM binds phosphate with high affinity ($K_a=1.3\times10^4$) via the formation of a ternary complex in which one phosphate replaces both inner-sphere water molecules. The formation of this complex is highly pH dependent; the phosphate is completely released from Gd-TREN-MAM below pH 2. Since the $Gd^{III}$ ion remains complexed by its ligand even under strong acidic conditions, Gd-TREN-MAM can be used at least ten times in a pH-based recycling scheme that enables catch-and-release of one phosphate per cycle. Gd-TREN-MAM is highly selective for phosphate over other anions of environmental concerns, including $HCO_3^-$, $HCO_2^-$, $CH_3CO_2^-$, $SO_4^{2-}$, $NO_3^-$, $NO_2^-$, $BrO_3^-$, $AsO_4^-$, $F^-$, $Cl^-$, $Br^-$ and to a lesser extent, $ClO_3^-$. The development of such receptors that bind phosphate reversibly in a pH dependent manner opens the possibility to design catch-and-release systems for the purification of surface waters.

Environmental Significance.

As a key ingredient in fertilizers, significant concentration of phosphates can accumulate in agricultural runoffs.[1] The resulting surplus of nutrients causes eutrophication of surface and coastal waters, boosts algal growth, and creates dead zones that have significant economic and health impacts.[2] Many algal blooms are caused by toxic blue-green algae such as microcystis that produces microcystin, a toxin that is potentially lethal to both humans and animals.[3] Such algal blooms are now seen annually in Lake Erie. In 2015, it caused the city of Toledo to shut down its drinking water supply to its 400,000 residents for four days.[4] There is thus a need to remove excess phosphorus from surface water so as to reduce outbreaks of algal blooms and their impact on the ecosystem and the economy.[5]

Industrially, the sequestration of phosphate from wastewater is primarily performed by addition of ammonium chloride and magnesium chloride to wastewater in order to precipitate phosphate in the form of struvite—magnesium ammonium phosphate hexahydrate—a slow-release fertilizer of high commercial value.[6] Precipitation of struvite from polluted water has already been established in water treatment facilities of several cities worldwide.[6-8] However, the current technology requires substantial and permanent infrastructure investment along with high operational and maintenance costs that are not amenable to the purification of most inland and coastal waters, which are therefore not treated by such facilities.[9]

Aside from precipitations, anions can be removed from aqueous solutions by extractions with organic solvents. This approach, however, is not efficient for phosphate, an anion with high hydration enthalpy positioned high in the Hofmeister series.[10,11] Moreover, this approach has limited practicality for the purification of polluted waterways in agricultural areas as it is expensive, uses large amounts of organic solvents, produces substantial organic waste, and may require further separation procedures.

On an industrial scale, purification of water can also be performed with porous membranes that can separate out a desired species. Such membranes have been proposed, for instance, for heavy metal sequestration.[12-15] A number of materials have recently been reported for the sequestration of phosphate from aqueous systems, such as the self-assembled monolayer on membrane support of Chouyyok.[16] A variety of material adsorbents, in fact, have been generated which are simple to use and have high efficiencies.[17-19] Some of those systems also involve the use of lanthanide ions, such as the systems of Ou, Wu and Ping.[20-22] The limitations of these systems are two-fold. They suffer from poor selectivity for phosphate over other anions present in surface water, and most of them function optimally at acidic pH. The material developed by Chouyyok, for instance, suffers from moderate to large interference from chloride, nitrate, bicarbonate, sulfate and citrate ions. The presence of any of these anions interferes with the ability of the material to sequester phosphate since they essentially "clog" the material.

Although the selectivity of many materials have not been reported,[23] the pH dependence of their affinity for phosphate has. In most cases, the material binds phosphate with higher affinity at acidic pH.[24-29] This is often either due to coordination of hydroxide to the receptor and/or to electrostatic repulsion between the negatively charged surface and the phosphate anion. Unfortunately, this pH dependency limits their efficacy for directly removing phosphate from surface water which is not so acidic.

Some supramolecular receptors for binding phosphates at neutral pH have also been proposed, most notably in the design of fluorescent probes. In each case, these approaches rely on inorganic phosphate coordinating a weakly bound metal ion, usually $Zn^{2+}$ or $Cu^{2+}$, resulting in precipitation of the metal-phosphate complex.[30-32] These complexes cannot be recycled, since in each case the metal ion is precipitated with the phosphate ion.[33] Their utility is further limited since the transition metal-containing phosphate waste cannot be used for agricultural applications.[34]

As can be seen from the above examples, part of the problem hindering the development of efficient and recyclable material for phosphate sequestration arises from the general paucity of receptors that bind inorganic phosphates with sufficient affinity directly in complex aqueous media, with high selectivity over competing anions, and in a reversible manner such that both the device and the phosphates can be recycled. Herein, the rationale behind the design of supramolecular receptors that can catch inorganic phosphate with high affinity and directly from aqueous mixtures at neutral pH and release it under acidic conditions are described. Such receptors may be useful for example, for efficient recycling of phosphate from polluted waterways in rural area. The feasibility of this recycling approach is explored with a model complex, Gd-TREN-MAM (FIG. 1). Although this complex has previously been reported for application as an MRI contrast agent, its use for phosphate sequestration has not been previously evaluated. Indeed, the entire class of $Gd^{III}$-based contrast agents offers potential for environmental application of water purification that have yet been untapped.

Design of Supramolecular Receptor.

The parameters that determine whether phosphate receptors can be used in a pH-based recycling scheme are governed by the US Environmental Protection Agency (EPA) guidelines regarding surface water.[35] Relatively uncontaminated lakes have surface waters whose phosphorus levels range from 10 μg/L to 30 μg/L. For the prevention of algae blooms, the EPA recommends that the total phosphates and phosphorus should not exceed 50 μg/L in any stream at the point where it enters a lake or reservoir, nor 25 μg/L within the lake or reservoir.[35] The desired goal for prevention of plant nuisances in streams or other flowing waters that do not discharge directly to lakes or impoundments is a total phosphorus concentration below 100 μg/L.[35] With this in mind, it is desirable for a receptor for catch-and-release of phosphate to high affinity for $H_2PO_4^-$/$HPO_4^{2-}$ in the range of 25-50 μg/L at neutral pH but low affinity for $H_2PO_4^-$ below pH 3. Note that at neutral pH, monohydrogen phosphate, $HPO_4^{2-}$, is in equilibrium with dihydrogen phosphate, $H_2PO_4^-$. Although the metal studied herein preferentially bind $HPO_4^{2-}$ at neutral pH, the equilibriums (2)-(4) must be taken into consideration in the determination of $K_{MLPi}$.

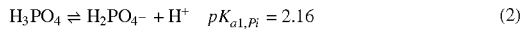

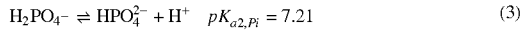

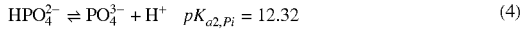

Moreover, it is desirable for the receptor itself (ML) to be stable both at neutral and acidic pH. It is also desirable for the receptor to be selective for inorganic phosphate over other anions present in lakes and rivers, including bicarbonate ($HCO_3^-$), formate ($HCO_2^-$), acetate ($CH_3CO_2^-$), sulfate ($SO_4^{2-}$), nitrate ($NO_3^-$), nitrite ($NO_2^-$), chlorate ($ClO_3^-$), bromate ($BrO_3^-$), arsenate ($AsO_4^{3-}$), fluoride ($F^-$), bromide ($Br^-$), and chloride ($Cl^-$).

Although no receptors have yet been reported that fulfill all of the desired properties, much can be learned from the design of supramolecular hosts and molecular probes previously reported for detecting inorganic phosphates in biological or clinical samples.[36-39] Importantly, given that phosphate levels are much higher in serum (1.12-1.45 mM), useful receptors for biological and clinical applications typically have much lower affinity for $H_2PO_4^-/HPO_4^{2-}$ than environmental ones.[40] Nonetheless, these receptors capitalize on three different types of interaction to successfully, although not always selectively, recognize phosphate: (1) Coordination to metal ions: Since phosphate is a hard ligand, this approach necessitates the use of hard metal ions such as late first row transition metals ($Cu^{2+}$ and $Zn^{2+}$ being the most commonly used).[41-44] (2) Hydrogen-bonding: In particular, selectivity for $HPO_4^{2-}$ and $H_2PO_4^-$, which have tetrahedral geometries, over nitrate and carbonate, which have trigonal planar geometries, can be achieved with tetrahedral hydrogen-bonding motifs.[45,46] (3) Charge[47,48]: Although weaker in water than in apolar solvents, electrostatic interactions are commonly used to increase affinity for ion. A positively charged receptor has higher affinity for anion, whereas a negatively charged receptor prefers cations. For metal-based sensors, such as those involving lanthanide, $Zn^{II}$ or $Fe^{III}$, since the oxidation state of the metal is constant, the charge of the metal-based receptor is essentially governed by the charge of the ligand L coordinating the metal ion. Although electrostatic interaction does not improve selectivity for one oxyanion over another, it can increase the binding affinity even in an aqueous environment.[49] Some of the best receptors for inorganic phosphates, including the copper receptor of Anslyn exploit all three of these interactions.[50-52] Most receptors, such as azacryptands,[53] ferrocene,[54,55] or quinolone receptors,[56] rely on electrostatic interaction and hydrogen bonding alone.

Gadolinium complexes are currently used extensively and primarily as contrast agents for Magnetic Resonance Imaging (MRI).[57] Although their medical applications are different than the environmental one of focus in this paper, such complexes present many benefits for phosphate recycling. They are stable in water at neutral pH and, depending on the ligand, also under acidic conditions. They have one to two open coordination sites filled by water molecules that can be readily displaced by certain hard anions, most notably $HPO_4^{2-}$. Several gadolinium-based MRI contrast agents are already known to bind phosphate in water at neutral conditions.[58-60] Significantly, and unlike in the zinc and copper-based fluorescent probes, the metal does not leach out of these MRI contrast agents upon binding the oxyanion. Instead, as seen in FIG. 1 phosphate binding results in the formation of a ternary $GdL(HPO_4)^-$ complex which remains water soluble. Moreover, gadolinium is a labile metal and as such phosphate binding and release occurs rapidly within minutes, a necessity to making our recycling scheme efficient. Lastly, these complexes may be readily synthesized on a ton scale, as needed for any future translational applications.

Figure 2:
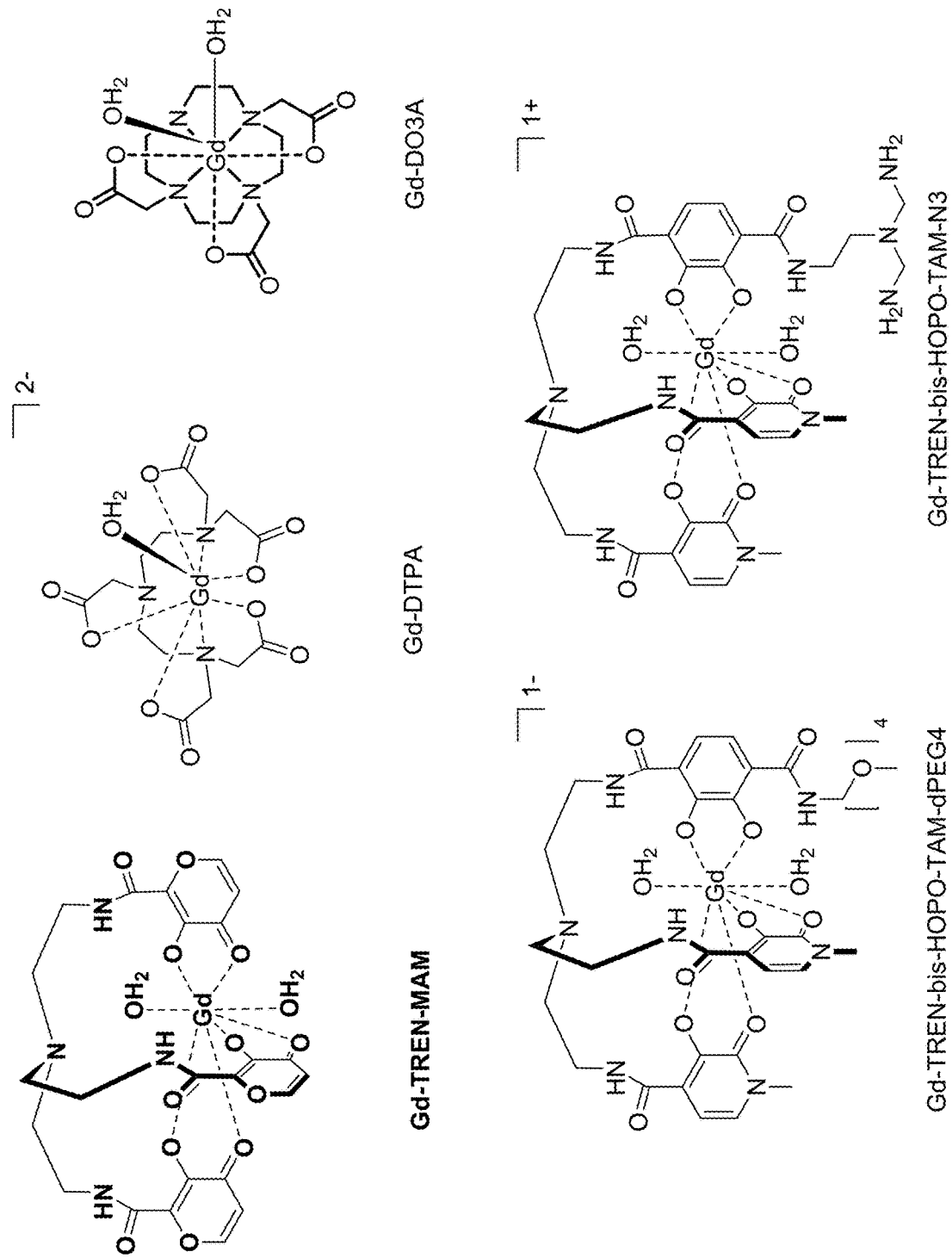
FIG. 2 shows the chemical structure of Gd-TREN-MAM and other $Gd^{III}$ complexes known to bind phosphate, Gd-DTPA, Gd-DO3A, Gd-TREN-bisHOPO-TAM-dPEG4, and Gd-TREN-bisHOPO-TAM-N3. The nature of the ligand L has a significant effect on the affinity of the complex GdL for phosphate.

Although complexes of gadolinium and other lanthanide ions with open coordination sites are well known to bind phosphates, they do not all do so with the same affinity and selectivity.[61,62] Even minor differences in ligand can lead to substantial changes in anion recognition. For instance, both Gd-DO3A and Gd-DTPA (see FIG. 2 for chemical structure), two gadolinium complexes with polyaminocarboxylate ligands, bind $HPO_4^{2-}$ in water. The affinity of the macrocyclic complex, Gd-DO3A, for phosphate, however, is nearly three orders of magnitude higher than that of its linear analogue, Gd-DTPA, (Log $K_{a, LMPi}$=4.8 for Gd-DO3A and 2.0 for Gd-DTPA).[57,59] Unfortunately, this class of lanthanide complexes has in general poor selectivity over bicarbonate—Gd-DO3A binds $HPO_4^{2-}$ with similar affinity as $HCO_3^-$, Gd-DTPA has barely a two-fold selectivity for $HPO_4^{2-}$ over $HCO_3^-$. This lack of selectivity hinders their use for phosphate recycling.

Another class of gadolinium complexes which includes those with the tripodal, tris-bidentate architecture, such as Gd-TREN-bisHOPO-TAM (FIG. 2), also bind phosphate but with excellent selectivity over bicarbonate. Both the negatively charged Gd-TREN-bisHOPO-TAM-dPEG4 and the positively charged Gd-TREN-bisHOPO-TAM-N3 bind $HPO_4^{2-}$, albeit weakly (Log $K_{a, LMPi}$=1.4 and 2.4, respectively) at pH 7.4.[58] Interestingly and importantly, neither bind bicarbonate. Additional compounds were prepared and studied to determine if the affinity of the gadolinium ion for phosphate could be maintained while maintaining the selectivity for phosphate over bicarbonate by maintaining the overall ligand architecture constant but altering the nature of the bidentate ligand. Gd-TREN-MAM (FIG. 2) was reported by the Cohen group to be a stable and water soluble gadolinium complex with a similar architecture as the Gd-TREN-bisHOPO-TAM complexes, including two innersphere water molecules that could enable $HPO_4^{2-}$ binding. The more acidic nature of the TREN-MAM ligand ($\Sigma pK_a$=log $\beta_{014}$=21.9) compared to the TREN-bisHOPO-TAM ligand ($\Sigma pK_a$=log $\beta_{015}$=38.1) might confer higher affinity to the $Gd^{3+}$ center for $HPO_4^{2-}$.[58,63] Notably, Gd-TREN-MAM was previously reported to be more stable under acidic conditions than its HOPO analogue; the $Gd^{3+}$ ion does not leach out of the complex at or above pH 2, as desired for our recycling scheme.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The present disclosure is illustrated by the following examples. It is to be understood that the particular examples, materials, amounts, and procedures are to be interpreted broadly in accordance with the scope and spirit of the disclosure as set forth herein.

EXAMPLES

The ability of several lanthanide complexes to catch phosphate selectively directly from aqueous solutions and release it in a pH-dependent manner were evaluated. A first example is with Gd-TREN-MAM. As shown in FIG. 1, it was postulated that at neutral pH, the $Gd^{III}$ complex could bind $HPO_4^{2-}$ rapidly, with high affinity, and with high selectivity over other anions, notably $HCO_3^-$. At acidic pH, however, Gd-TREN-MAM could release the $H_2PO_4^-$ anion without leaching $Gd^{III}$. Importantly, since the Gd-TREN-MAM complex does not decompose throughout the cycle, it can be reused to sequester more phosphate.

The complex Gd-TREN-MAM was synthesized as previously reported.[63,64] Successful synthesis of the ligand was established by $^1H$ NMR and mass spectrometry, that of the $Gd^{3+}$ complex by UV-visible spectroscopy, mass spectrometry, and relaxometry. $^1H$ NMR spectra were obtained at room temperature on Bruker Advance III at 400 MHz at the LeClaire-Dow Characterization Facility of the Department of Chemistry at the University of Minnesota. Mass spectrometry was performed on a Thermo Electron corporation Finnigan TSQ Quantum Discovery Max. UV-visible spectra were recorded on a Varian Cary 100 Bio Spectrophotometer; data was collected between 200 and 800 nm using a quartz cell with a path length of 10 mm. The longitudinal water proton relaxation rate at 60 MHz was measured on a Bruker Minispec at 1.5 T using the inversion-recovery method. Temperature was kept constant during all experiments via the use of a Julabo F-25-ED refrigerating/heating circulator temperature controller that has an accuracy of 0.1° C. All pH measurements were performed using a Thermo Scientific Ag/AgCl refillable probe and an Orion star series pH meter.

The complex Gd-TREN-MAM was characterized by APCI-MS(+) (m/z 716.00 [M+H]$^+$) and UV-visible spectroscopy. As previously reported, the π-π* transition of Gd-TREN-MAM in aqueous solution at pH 7.4 ($\lambda_{max}$=322 nm) observed by UV-visible spectroscopy is blue-shifted by 8 nm compared to that of the free ligand TREN-MAM ($\lambda_{max}$=330 nm).[63,64] The concentration of the Gd-TREN-MAM aqueous stock solutions were determined by UV-visible spectroscopy using the intensity at $\lambda_{max}$=322 nm, assuming an $\varepsilon_{332}$=1474 cm$^{-1}$M$^{-1}$, calculated as ¾ of the extinction coefficient of Eu(5-LIO-MAM)$_2$ under the same conditions ($\varepsilon_{Eu(5\text{-}LIO\text{-}MAM)2}$=1965 cm$^{-1}$M$^{-1}$, Eu(5-LIO-MAM)$_2$ contains four MAM moieties whereas Gd-TREN-MAM contains three; the nature of the lanthanide ion does not affect the UV-visible spectrum)[65]. Longitudinal water proton relaxation times ($T_1$) were measured using the inversion-recovery pulse sequence at constant temperature using the following parameters: 2 scans, 3.5 s recycle delay, 58-62 dB gain, 5 ms first pulse separation, 28000 ms final pulse separation, 20 data points for fit, 0.05 ms delay sample window, 0.02 ms sample window, 6 s saturation curve display time.

All longitudinal relaxation time measurements were performed on aqueous solutions of Gd-TREN-MAM at a final concentration of 50.0 μM in 50 mM HEPES at pH 7.4 on 200 μL aliquots. Titration of Gd-TREN-MAM with phosphate was performed by generating two aqueous solutions: one of the free complex (final concentrations 50.0 μM Gd-TREN-MAM in 50 mM HEPES (aq) at pH 7.4) and one of the complex in the presence of 2000 eq. of $HPO_4^{2-}/H_2PO_4^-$ (final concentrations 50.0 μM Gd-TREN-MAM, 100 mM $K_2HPO_4/KH_2PO_4$ in 50 mM HEPES at pH 7.4). Longitudinal relaxation times of the solution of Gd-TREN-MAM was measured as the solution of Gd-TREN-MAM/phosphate was titrated into it. The solution was allowed to equilibrate for at least 10 min after each addition to ensure that thermodynamic equilibrium is reached. The longitudinal relaxivity of the initial solution of titrate and titrant were used to complete the titration. This approach ensures that the concentration of the $Gd^{III}$ complex is kept constant throughout the experiment, as desired for accurate determination of $K_a$. The titration was performed in triplicate.

The selectivity experiment was performed as follow. The longitudinal relaxation times ($T_1$) of 200 μL aliquots of Gd-TREN-MAM (final concentrations 50.0 μM Gd-TREN-MAM in 50 mM HEPES (aq) at pH 7.4) in the presence of 300 eq. of competing anion, either $NaHCO_3$, $NaHCO_2$, $K(C_2H_3O_2)$, $K_2SO_4$, $Na(NO_3)$, $Na(NO_2)$, $KClO_3$, $NaBrO_3.2H_2O$, $Na_2H(AsO_4).7H_2O$, $KF.2H_2O$, KCl, or $NaBr.2H_2O$ (final concentration 15 mM) was measured as described above. The effect of each competing anion on phosphate binding was similarly evaluated by measuring the longitudinal relaxivity of 200 μL aliquots of Gd-TREN-MAM (final concentrations 50.0 μM Gd-TREN-MAM in 50 mM HEPES (aq) at pH 7.4) in the presence of 300 eq. of competing anion, either $NaHCO_3$, $NaHCO_2$, $K(C_2H_3O_2)$, $K_2SO_4$, $Na(NO_3)$, $Na(NO_2)$, $KClO_3$, $NaBrO_3.2H_2O$, $Na_2H(AsO_4).7H_2O$, $KF.2H_2O$, KCl, or $NaBr.2H_2O$ (final concentration 15 mM) and 300 eq. $K_2HPO_4/KH_2PO_4$ (final concentration 15 mM). This experiment was performed in triplicate, in each case with new solution of Gd-TREN-MAM with competing anions.

The pH titration was performed by measuring the $T_1$ of 200 μL aliquots of a 2.5 mL solution of Gd-TREN-MAM (final concentrations 50.0 μM in 50 mM HEPES (aq)) after addition of either concentrated NaOH (aq) or concentrated HCl (aq). The pH was measured after each addition of base or acid. The solution was allowed to equilibrate for 10 min before the pH and $T_1$ were measured to ensure that thermodynamic equilibrium is reached. The experiment was repeated with a solution of Gd-TREN-MAM (final concentrations 50.0 μM in 50 mM HEPES (aq)) containing 300 eq. of potassium phosphate (final concentration 15 mM).

The recycling cycle was performed ten times as follows. First, an aqueous stock solution of potassium biphosphate (40 mM, 1.1 mL, 300 eq.) was added to an aqueous solution of Gd-TREN-MAM (1.4 mM, 0.11 mL, 1 eq.) for a final concentration of 0.13 mM complex and 40 mM phosphate species. The initial pH was measured at pH=8.4. The pH was adjusted to 7 using 12 M HCl (aq). The longitudinal relaxation time, $T_1$, was measured as described above on an aliquot (200 μL) that was subsequently returned to the stock solution. The pH of the stock solution was carefully adjusted to 2 using 12 M HCl (aq). The longitudinal relaxation time, $T_1$, was again measured on an aliquot (200 μL) that was subsequently returned to the stock solution. The pH of the stock solution was carefully adjusted to 7 using 1 M KOH (aq). These last two steps were repeated nine more times for a total of ten pH 7/2 cycles.

Results and Discussion

The fact that the paramagnetic Gd-TREN-MAM behaves as a water relaxation agent facilitates the determination of its binding affinity for anions and the nature of the ternary complex. This is an advantage of lanthanide complexes over transition metal complexes such as $Zn^{II}$ or $Fe^{III}$ for which it is substantially more difficult to determine how an anion binds to the metal complex in solution. In particular, for a $Gd^{III}$ complex, the longitudinal relaxivity, $r_1$, of the ternary complex enables us to determine whether the anions coordinate directly to the $Gd^{3+}$ ion by replacing either one or both water molecules, or if they bind to the complex via the formation of a second sphere of coordination whereby the inner-sphere water molecules are not displaced. The longitudinal relaxivity of a $Gd^{3+}$ complex, $r_1$, is determined by subtracting the diamagnetic contribution of pure water, $T_{1,dia}$, from the observed relaxation time, $T_{1,obs}$, of the solution containing the Gd complex of concentration [Gd] as follows in equation 5:[60]

$$r_1 = \frac{1}{[Gd]}\left(\frac{1}{T_{1,para}}\right) = \frac{1}{[Gd]}\left(\frac{1}{T_{1,obs}} - \frac{1}{T_{1,dia}}\right) \quad (5)$$

The longitudinal relaxivity has two contributions (Equation 6). The inner-sphere relaxivity, $r_1^{I.S.}$, which comes from water molecules directly coordinated to the $Gd^{3+}$ ion, and the outer-sphere relaxivity, $r_1^{O.S.}$. The latter includes contributions from water molecules which are not coordinated to the Gd(III) center but interact strongly with the functional groups of the ligands such that they do not diffuse readily out of its periphery. It also includes those water molecules that interact with the $Gd^{3+}$ center according to a dipolar intermolecular mechanism whose fluctuations are governed by the random translational motion of the molecules. Although it is a smaller contribution, since the outer-sphere component cannot be fully eliminated, the relaxivity of a $Gd^{3+}$ complex $r_1$ (Equation 6) does not decrease to 0 $mM^{-1}_{Gd}s^{-1}$.[66]

$$r_1 = r_1^{I.S.} + r_1^{O.S.} \quad (6)$$

In turn, the longitudinal inner-sphere relaxation rate, $r_1^{I.S.}$, of a $Gd^{3+}$ complex is a function of c, the molar concentration, q, the number of coordinated or inner-sphere water molecules, their residence time (inverse of the water exchange rate), and $1/T_{1m}$, the longitudinal proton relaxation rate.[67]

$$r_1^{I.S.} = \frac{cq}{55.5}\left(\frac{1}{T_{1m} + \tau_m}\right) \quad (7)$$

As is apparent from Equation 7, if phosphate binds the GdL complex in such a way that it directly coordinates the $Gd^{2+}$ by replacing one or more inner-sphere water molecule, q will decrease proportionally to the number of water molecules displaced and as such so will both the inner-sphere and the longitudinal relaxivity.

Binding of an anion to the GdL complex without displacement of inner-sphere water molecules has an opposite effect on longitudinal relaxivity. For small molecules, the primary component governing the longitudinal proton relaxation rate, $1/T_{1m}$, is the dipolar contribution, $1/T_{1,p}$. This contribution results from through-space interactions due to the random fluctuations of the electronic field. If zero-field splitting is neglected, and if it is assumed that the complex undergoes isotropic reorientation, it can be described by the Solomon-Bloembergen-Morgan theory. Of the several parameters that influence $1/T_{1,p}$, the rotational correlation time, $\tau_R$, is affected by outer-sphere anion binding. Indeed, the formation of ternary complexes between GdL and anions whereby the anions do not displace inner sphere water, i.e. $GdL(H_2O)_n(anion)$, results in a small but noticeable increase in molecular weight and thus in $\tau_R$, which in turn also increases $r_1$. One should note that relaxivity is also influenced by both temperature and the magnetic field strength at which it is measured ($B_0$), and as such both of these parameters should remain constant. All our experiments were thus performed at constant magnetic field strength (60 MHz), constant temperature (25.0° C.), and (except for the pH dependence studies) at constant pH=7.4 using HEPES buffer.[57]

Figure 3:
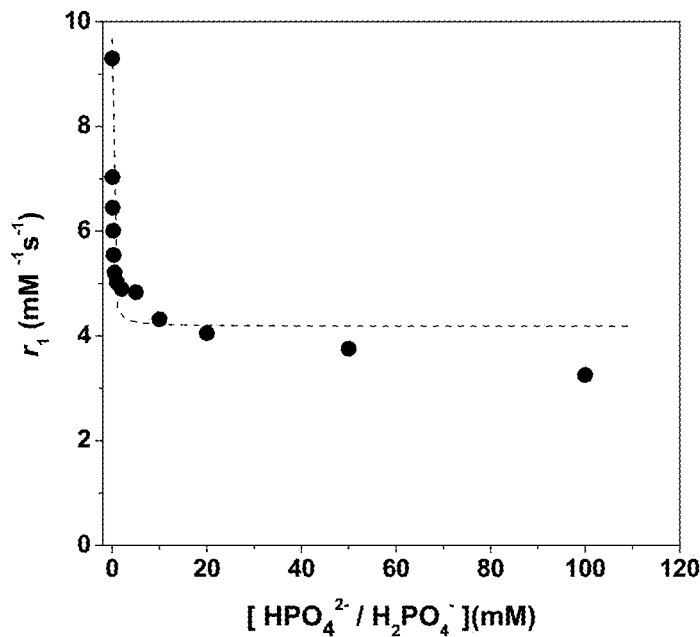
FIG. 3 shows the longitudinal relaxivity of Gd-TREN-MAM as a function of the concentration of $H_2PO_4^-/HPO_4^{2-}$. Experimental conditions: [Gd-TREN-MAM]=50 μM in 50 mM HEPES (aq), pH 7.4, T=25° C. Error bars represent standard deviations. The dotted line represents the fit to the PRE equation (8) with the variables optimized resulting in: $R_f$=9.3, $R_b$=3.8, n=1, $C_t$=1E-3, $K_a$=12500 with a $Chi^2$ value of 0.20841.

The relaxivity of Gd-TREN-MAM in water at neutral pH at 60 MHz and 25.0° C. is 9.3 $mM^{-1}_{Gd}s^{-1}$, in agreement with two inner-sphere water molecules directly coordinated to the $Gd^{3+}$ ion. As can be seen in FIG. 3, addition of inorganic phosphate at pH 7.4 results in a substantial and rapid decrease in longitudinal relaxivity from 9.3 $mM^{-1}_{Gd}s^{-1}$ to 4.5 $mM^{-1}_{Gd}s^{-1}$. As discussed above, this observation is consistent with the formation of a ternary $GdL(HPO_4)^-$ complex whereby the inorganic phosphate bound replaces both water molecules (Δq=2). Indeed, the longitudinal relaxivity of the GdL-phosphate adduct is comparable to that of q=0 complexes of similar molecular weight for which the relaxivity results only from the outer-sphere mechanism. The binding affinity ($K_a$) of phosphate for the complex and the number of phosphate bound per $Gd^{III}$ complex can both be determined by the proton relaxation enhancement (PRE) method according to Equation 8.[68]

$$y = \frac{(K_a C_t + nxK_a + 1) - \sqrt{(K_a C_t + nxK_a + 1)^2 - 4K_a^2 C_t nx}}{2K_a} \times \quad (8)$$
$$1000(R_b - R_f) + (R_f C_t \times 1000) + 0.38$$

Where y is the observed longitudinal relaxation rate of an aqueous solution of the paramagnetic complex Gd-TREN-MAM at a concentration of $C_t$, x is the total concentration of phosphate $[P_i]_t$, $R_f$ is the relaxivity of the free unbound complex, $R_b$ is the relaxivity of the phosphate bound complex, and n is the number of phosphate binding sites. The factor 0.38 in the equation takes into account the $R_1$ (or $1/T_{1,dia}$) of the diamagnetic solution (pure water).

Figure 8:
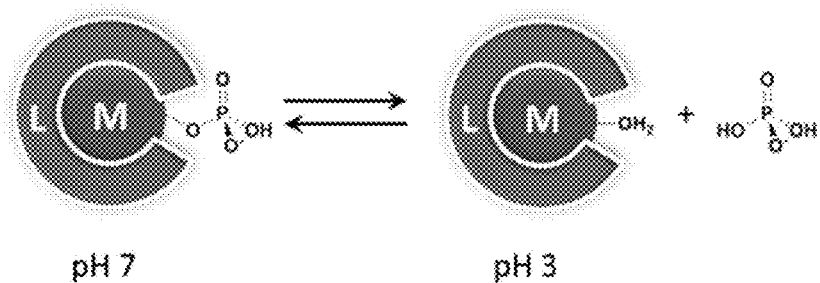
FIG. 8 depicts the pH-dependent catch-and-release of the phosphate anion.

Fitting of the titration data according to this method (FIG. 3, dotted line) confirms that only one phosphate coordinates each $Gd^{III}$ ion. This observation is consistent with other tripodal $Gd^{III}$ complexes of similar geometry that also bind only one phosphate anion per $Gd^{III}$ ion[58]. Impressively, the affinity of Gd-TREN-MAM for phosphate, $K_{a,LMPi}=1.3\times 10^4$, is substantially higher than that of similar gadolinium complexes which also incorporates tris-bidentate aromatic ligands. For example, the analogues Gd-TREN-bisHOPO-TAM-N3 and Gd-TREN-bisHOPO-TAM-dPEG4 bind $HPO_4^{2-}/H_2PO_4^-$ with 50-500 fold lower affinity ($K_{a,LMPi}$=250 and 25, respectively).[58]. These results highlight the significant effect that the ligand L can have on the affinity of a lanthanide complex for an anion. For a constant complex geometry, a more acidic ligand L confers to the complex GdL with a higher affinity for $HPO_4^{2-}/H_2PO_4^-$. The affinity of Gd-TREN-MAM for phosphate in water is comparable to those observed with other systems in mixed aqueous solutions, including the copper systems of Anslyn (Log $K_{a,LPi}$ up to 4),[50,51] the $Cu^{2+}$ system of Hatai (Log $K_{a,LPi}$ of 5 in 80% $CH_3OH$),[30] and the $Ga^{3+}$ system of Svane (Log $K_{a,LPi}$ of 5-6).[69] Not surprisingly, studies performed in non-aqueous solvents, such as Suganya $Zn^{2+}$ complex (Log $K_{a,LPi}$ of 5 in DMSO)[31] and Otón's ferrocene system (Log $K_{a,LPi}$ of 7 in $CDCl_3$)[54] report much higher affinity for phosphate, highlighting the importance of hydration of the phosphate anion in its recognition in aqueous systems. One notable exception is the Grell's azacryptand which has a high affinity for phosphate in water (Log $K_{a,LPi}$ of 7 at pH 7.0).[53] Importantly, though, none of these systems have been reported to be able to bind phosphate in a reversible and pH-dependent manner as needed for catch-and-release of the anion and recycling of both phosphate and the receptor. The catch and release of the anion is depicted in FIG. 8

The theoretical phosphate removal efficiency of disclosed systems, which are defined as the percentage of phosphate bound by the $Gd^{III}$ complex over the overall phosphate present in solution ($[Pi]_{Gd}/[Pi]_{total}\times100\%$), can be calculated from the binding constant, $K_a$, as a function of both the concentration of phosphate and that of the gadolinium complex following the method described by Thordarson using Equation 9.[70]

$$\frac{[P_i]_{Gd}}{[P_i]_{total}} \times 100\% = \frac{C_t + [P_i]_t + \frac{1}{K_a} - \sqrt{\left(C_t + [P_i]_t + \frac{1}{K_a}\right)^2 - 4C_t[P_i]_t}}{2[P_i]_t} \times 100\% \quad (9)$$

Figure 4:
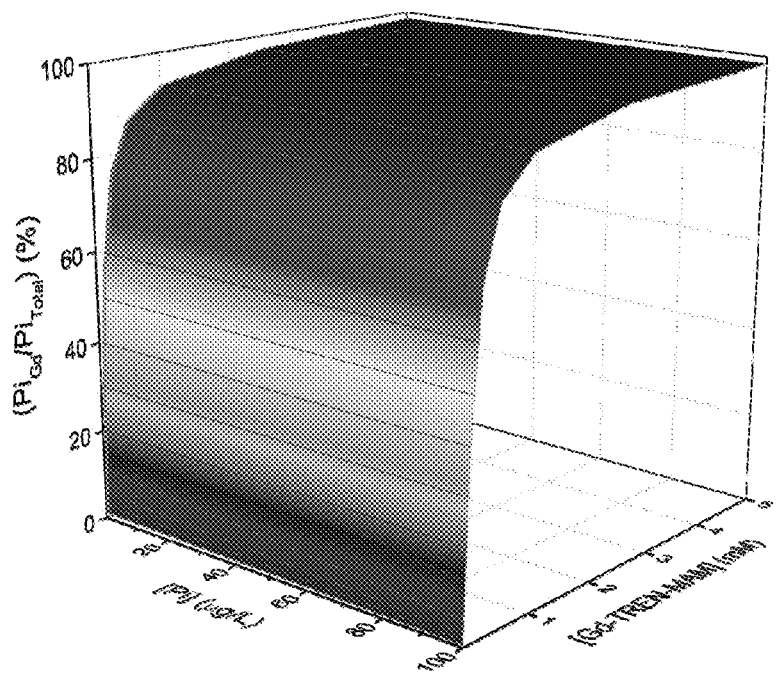
FIG. 4 shows the calculated phosphate removal efficiency of Gd-TREN-MAM as a function of the concentration of Gd-TREN-MAM and concentration of $H_2PO_4^-/HPO_4^{2-}$. Removal efficiency was determined as % of phosphate bound to the $Gd^{III}$ complex over total concentration of all phosphate species.

As can be seen in FIG. 4, disclosed complexes can efficiently sequester phosphate in the ppb range (1 μg/L-100 μg/L). At a concentration of 5 mM, Gd-TREN-MAM can efficiently remove 99% of the phosphate present in solution when the concentration of phosphate ranges between 1-100 μg/L. The complex can thus be used to sequester phosphate present at 25 μg/L, a concentration which causes eutrophication, and 100 μg/L, a concentration that affect water purification. This efficiency bodes well for the further development of membrane-supported complexes more amenable to water purification systems.

Figure 5:
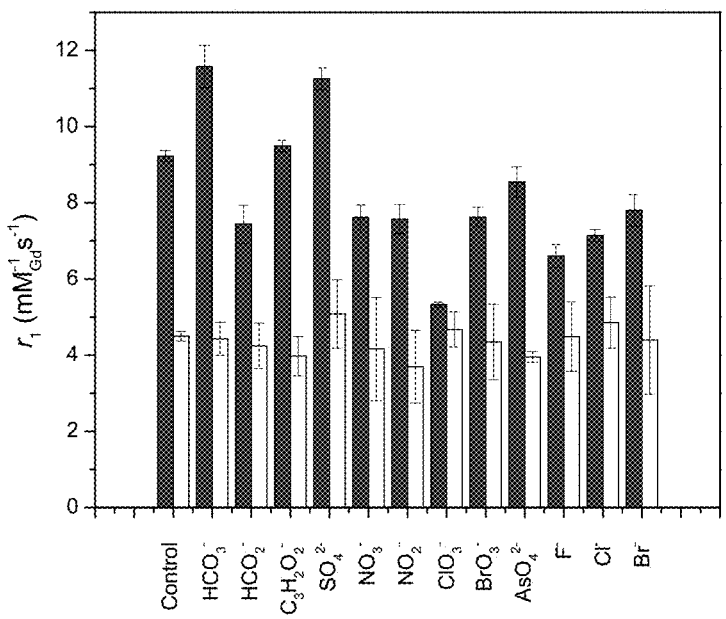
FIG. 5 shows the selectivity of Gd-TREN-MAM (control) to anions. Black bars represent the longitudinal relaxivity after addition of an excess at 300 eq. of the appropriate anion (15 mM $NaHCO_3$, $NaHCO_2$, $K(C_2H_3O_2)$, $K_2SO_4$, $Na(NO_3)$, $Na(NO_2)$, $KClO_3$, $NaBrO_3.2H_2O$, $Na_2H(AsO_4).7H_2O$, $KF.2H_2O$, KCl, $NaBr.2H_2O$). White bars represent $r_1$ after subsequent addition of 15 mM $K_2H(PO_4).H_2O$. Experimental conditions: [Gd-TREN-MAM]=50 μM in 50 mM HEPES (aq), pH 7.4, T=25° C. Anion salts: $K_2H(PO_4).H_2O$. Error bars represent standard deviations (n=3).

The selectivity of Gd-TREN-MAM for phosphate over other anions commonly found in waterways and fertilizers, as determined by relaxivity, is shown in FIG. 5. Of all the anions considered, only $ClO_3^-$ was found to also bind the $Gd^{3+}$ complex in such a way that it displaces one water molecule with high affinity, albeit with lower affinity than phosphate ($\Delta r_1$=-4.0 $mM^{-1}$ $s^{-1}$ for 300 eq. of $ClO_3^-$ compared to -4.8 $mM^{-1}$ $s^{-1}$ for 300 eq. $H_2PO_4^-/HPO_4^{2-}$). Given the low concentration of chlorate from common pesticides present in surface water that is contaminated by agricultural runoffs, it is unlikely to substantially affect the ability of the receptor to catch-and-release phosphate from polluted water.[71] Note that since drinking water can contain high levels of chlorate as byproducts of water disinfection treatments (200 μg/L range),[72] Gd-TREN-MAM will likely catch both pollutants from treated drinking water. Although in this situation, it might not enable recycling of pure phosphate.

A few anions, such as $F^-$, decrease slightly the relaxivity of Gd-TREN-MAM. The small change indicate that the anions can also bind to the complex by replacing an inner-sphere water molecule, but that the binding affinity of the Ge complex for these anions is so weak that association constants could not be accurately determined. Two anions, $HCO_3^-$ and $SO_4^{2-}$, cause a slight increase in $r_1$. As described above, this indicates that these anions bind loosely to the outer-sphere of GdL but that, more importantly, they do not coordinate directly the $Gd^{3+}$ center. Importantly, in each case, addition of a competing anion does not affect further binding by phosphate; the decrease in relaxivity observed upon addition of phosphate is similar regardless of the presence of other anions (FIG. 5, white bars).

Unusually, and significantly, although Gd-TREN-MAM has a substantially higher affinity for phosphate than other tripodal complexes of its class, it also maintains a high selectivity over $HCO_3^-$. Bicarbonate does not coordinate the $Gd^{3+}$ ion of Gd-TREN-MAM by replacing one or more inner-sphere water molecule. These results indicate that proper choice of the ligand L in lanthanide complexes can lead to a high affinity for $H_2PO_4^-/HPO_4^{2-}$ at neutral pH while maintaining a high selectivity over bicarbonate and other anions. Interestingly, even though it does not bind $HCO_3^-$ at neutral pH, under basic conditions, Gd-TREN-MAM does appear to bind $CO_3^{2-}$. This results in a decrease of relaxivity of the $Gd^{III}$ complex in aerated aqueous solution above pH 9. Note that this class of metal complexes has unusually high selectivity for phosphate over bicarbonate, indicating that both metal and ligand geometry likely play a role in anion selectivity. In comparison, the lanthanide complexes based on polyaminocarboxylate ligands bind $HCO_3^-$ with poor to no selectivity over phosphate.

Figure 6:
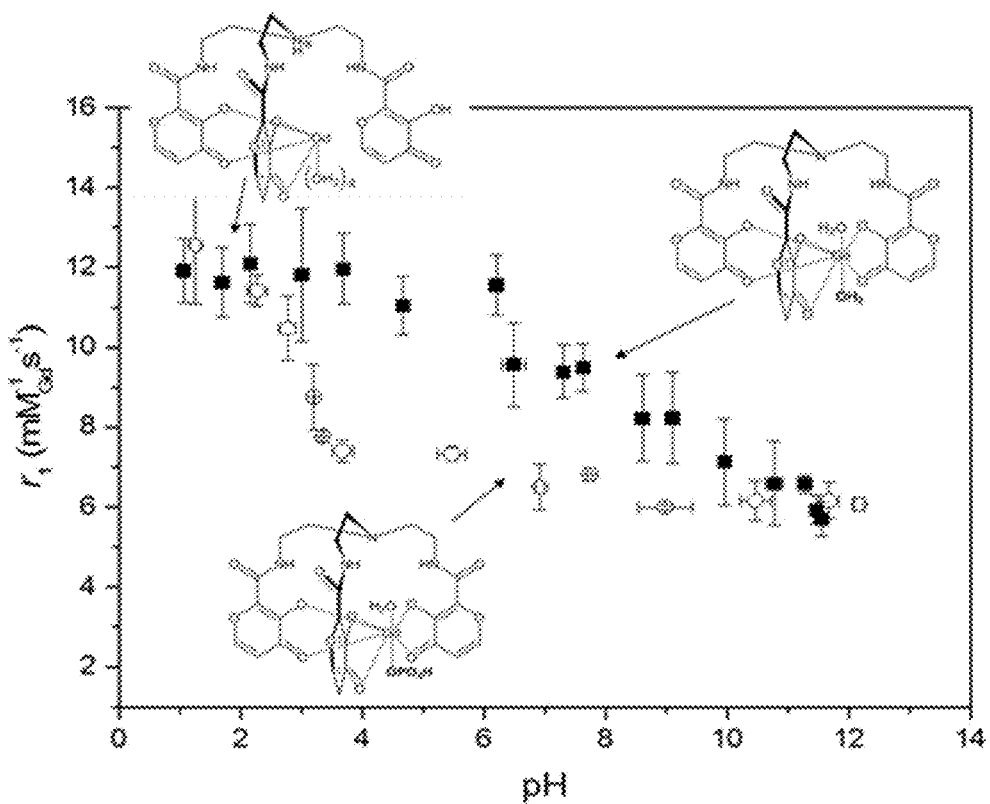
FIG. 6 shows the relaxivity of Gd-TREN-MAM in the absence (filled squares) and presence (open circles) of 300 eq. of phosphate as a function of pH. Experimental conditions: [Gd-TRENMAM]=50 μM in 50 mM HEPES (aq), pH 7.4, T=25° C. Error bars represent standard deviations (n=3).

High affinity and selectivity are only two properties of a gadolinium complex suitable for catch-and-release of phosphate. For the recycling scheme to work, the complex should also be able to release phosphate under acidic conditions without leaching the gadolinium ion. This property has been evaluated by monitoring the longitudinal relaxivity of the GdL complex and that of its phosphate adduct, $GdL(H_nPO_4)$ as a function of pH. As can be seen in FIG. 6, the relaxivity of Gd-TREN-MAM does increase from 3.5 to 10.7 $mM^{-1}_{Gd}s^{-1}$ as the pH decreases from 12 to 2.4. According to the protonation constants of the complex previously reported by Cohen et al., this behavior corresponds to protonation of both the central TREN nitrogen and one MAM arm with resulting decomplexation of a single of the three maltol arms.[63] Predominantly, this indicates that even at pH 2, the $Gd^{3+}$ ion remains chelated by the remaining two maltol arms and thus the metal does not leach out of its ligand. The stability of the phosphate adduct of Gd-TREN-MAM also shows a strong pH dependence. Above pH 3, $r_1$ remains low, corresponding to a q=0 $GdL(HPO_4)^-$ complex, indicating that the ternary phosphate complex is stable for a wide pH range. Between pH 2 and 3, however, the relaxivity increases substantially to 10.7, which is that of the protonated Gd-TREN-MAM complex. This observation is in agreement with release of the phosphate and protonation of one of the maltol arms, resulting in the formation of the same q=4 Gd-TREN-MAM complex. Altogether, these data suggest that inorganic phosphate can be released from the gadolinium complex under acidic conditions without removing the metal ion from its TREN-MAM ligand. This suggests that the complex can be used in the future design of materials or polymeric membranes that can catch and release phosphate in a pH-dependent manner for purification of polluted surface waters.

Figure 7:
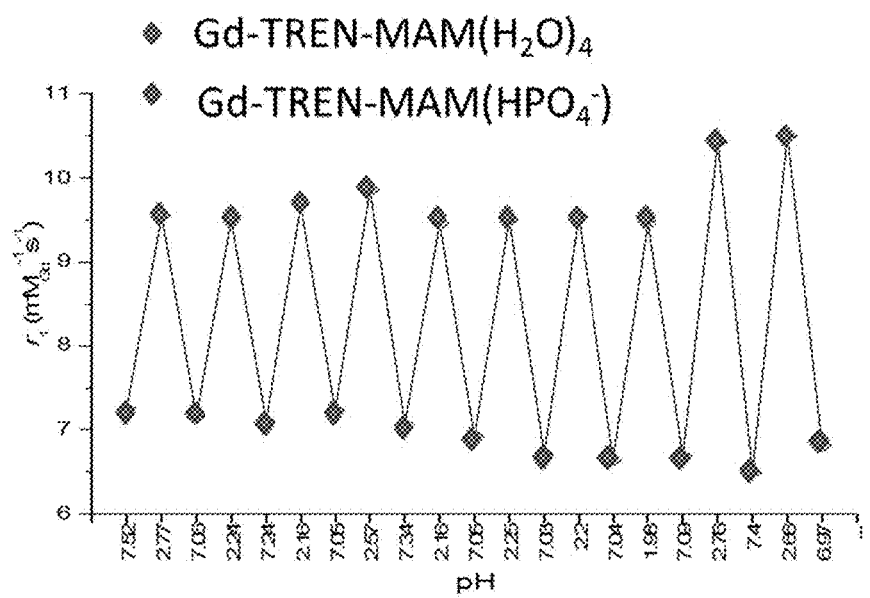
FIG. 7 shows the ability of Gd-TREN-MAM to undergo multiple catch-and-release cycle as shown in FIG. 1. Longitudinal relaxivity of Gd-TREN-MAM in the presence of $H_2PO_4^-/HPO_4^{2-}$ at neutral pH and after subsequent addition of HCl or KOH. The relaxivity of the complex is lower at neutral pH where it catches phosphate and higher at acidic pH where it releases phosphate. Experimental conditions: [Gd-TRENMAM]=132 µM in water, [phosphate]=39.6 mM, T=25° C.

The strong dependence of the affinity of Gd-TREN-MAM for phosphate on pH and the stability of the $Gd^{III}$ complex under both neutral and acidic conditions strongly suggest that the complex could be used in a pH-dependent recycling scheme as drawn in FIG. 1. In this scheme, the $Gd^{III}$ complex binds phosphate at neutral pH, but releases it at pH 2. Release of phosphate under acidic condition regenerates the $Gd^{III}$ complex that can then be used again in the next cycle. An important part of this recycling scheme thus depends on the ability of Gd-TREN-MAM to withstand multiple pH catch-and-release cycling. As shown in FIG. 7, Gd-TREN-MAM is stable for at least ten such cycles. In each cycle, the free (at pH 2) and phosphate-bound (at pH 7) relaxivities remain constant, indicating that Gd-TREN-MAM stays intact. This stability of the complex was also established by monitoring its UV-visible spectrum with each pH cycle.

Altogether, these data demonstrate that lanthanide-based supramolecular receptors can be designed for recyclable pH-dependent catch-and-release of phosphate from aqueous solutions. Gd-TREN-MAM is a complex that is stable in water both at neutral and acidic conditions. It readily binds phosphate in water with high affinity at neutral pH and importantly, with high selectivity over other competing anions, most notably carbonate and nitrate. The formation of the ternary $GdL(H_nPO_4)^{3-n}$ complex is highly pH-dependent, with complete release of phosphate observed at pH 2. The high binding affinity of the receptor for phosphate, its high stability both at neutral and under acidic pH, and its ability to withstand multiple catch-and-release pH cycles highlight the potential of this class of compound in the development of material for sequestration of phosphate.

Other examples of lanthanide complexes that can be used to catch phosphate with high affinity at neutral pH and release it under acidic pH include Gd-TREN-1,2-HOPO, Gd-TREN-Gly-MAM, Gd-TREN-Glu-MAM, Gd-TREN-LysMAM, Eu-3,3-Li-HOPO-LysHOPO, Gd-TREN-HMA, Gd-TREN-HPA, La-TREN-MAM, Lu-TREN-MAM, Gd-TREN-IAM. The syntheses of these complexes are described below, as are the overview of their affinity for phosphate and other anions in water. Gd-TREN-1,2-HOPO and Gd-TREN-IAM were both synthetized according to literature protocols.[74,75]

Figure 9:
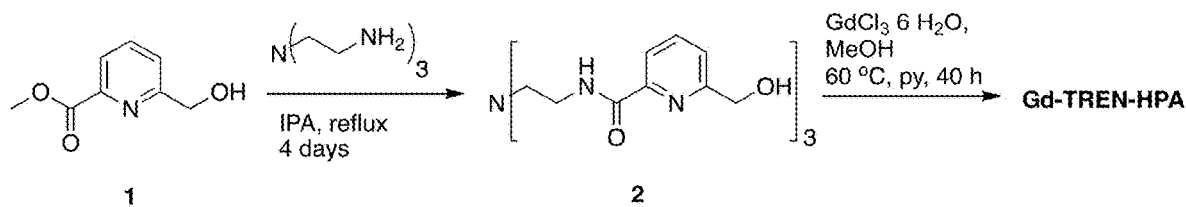
FIG. 9 shows a synthetic route for Gd-TREN-HPA.

TREN-HPA & Gd-TREN-HPA:

A synthetic route for Gd-TREN-HPA is shown in FIG. 9.
Synthesis of TREN-HPA (2): Tris(2-aminoethyl)amine (TREN, 0.302 g, 2.07 mmol) was added to Methyl 6-hydroxymethyl)-picolinate (HPA, 1, 1.008 g, 6.03 mmol) dissolved in isopropyl alcohol (75 mL). The reaction mixture was stirred and refluxed at 85° C. for four days under nitrogen. Analysis by TLC supports the formation of a product. The solvent was removed from the reaction mixture by rotary evaporation. $^1$H NMR (400 MHz, Chloroform-d) δ 8.69 (t, J=5.8 Hz, 1H), 7.77 (dd, J=7.7, 1.0 Hz, 1H), 7.59 (t, J=7.7 Hz, 1H), 7.32 (dd, J=7.7, 1.1 Hz, 1H), 4.81-4.77 (m, 1H), 4.67 (s, 2H), 3.58 (d, J=4.9 Hz, 2H), 2.88-2.82 (m, 2H).
Synthesis of Gd-TREN-HPA:

To a stirred solution TREN-HPA (2, 0.075 g, 0.13 mmol), in dry MeOH (5 mL) under Argon atmosphere was added $GdCl_3$ $6H_2O$ (0.055 g 0.14 mmol) and the reaction turned to light pink opaque from a clear yellow solution. Then excess pyridine was added to maintain to neutral pH of the reaction mixture. The reaction mixture was stirred at 60° C. for 40 h and then MeOH was completely concentrated under rotary evaporation and crude material was further triturated with $Et_2O$ to afford final metal complex.

TREN-Lys-MAM & Gd-TREN-Lys-MAM

Figure 10:
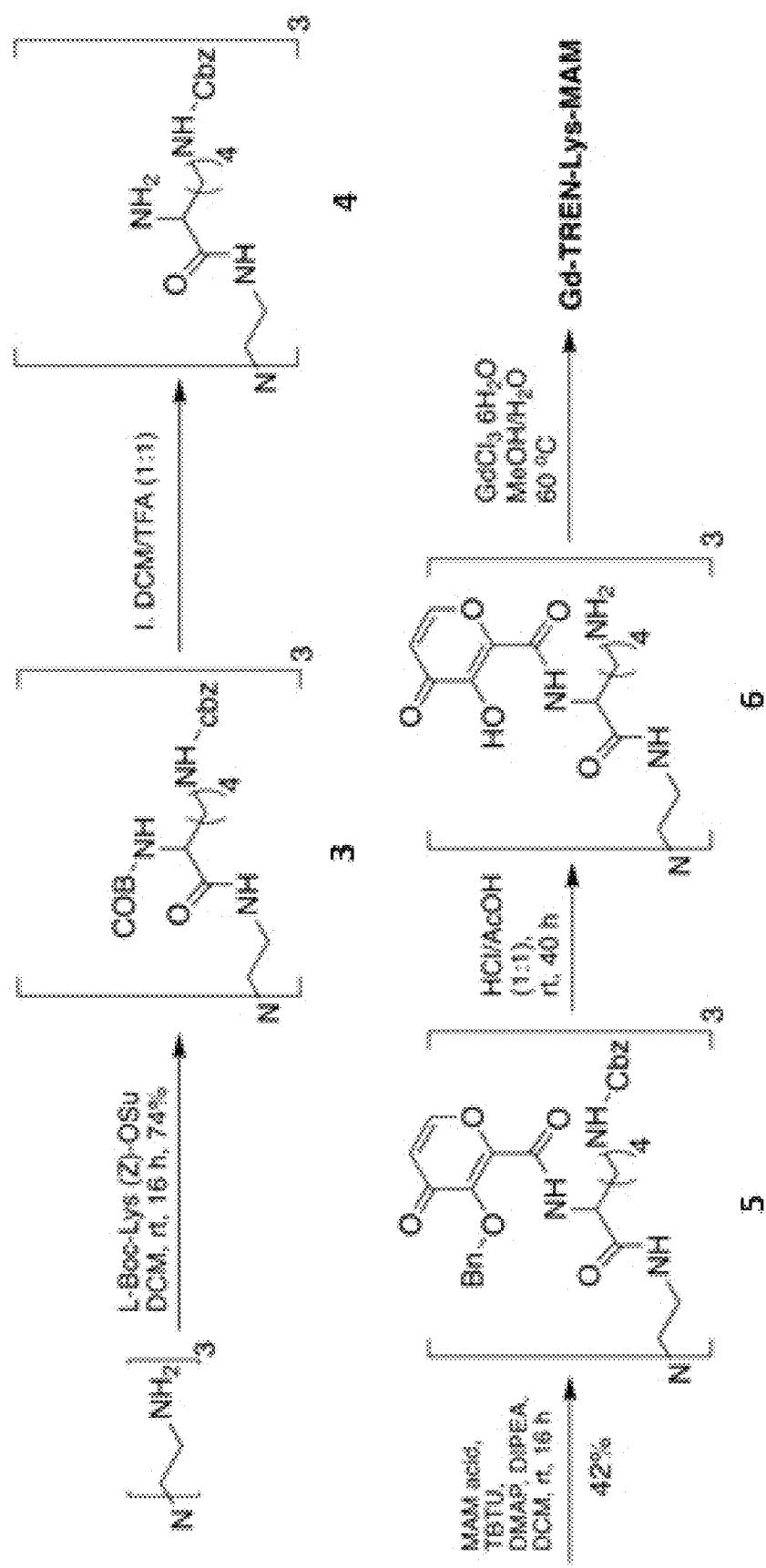
FIG. 10 shows a synthetic route for Gd-TREN-Lys-MAM.

A synthetic route for TREN-Lys-MAM & Gd-TREN-Lys-MAM is shown in FIG. 10.
Synthesis of TREN-Boc-Lys(Z) (3):

To a stirred solution of TREN (0.1 g, 0.68 mmol) in dry DCM (10 mL) was added Boc-Lys-(Z)-OSu (1.01 g, 2.09 mmol) in dry DCM (15 mL) and the resulted reaction mixture was allowed to stir at rt for 16 h. The resulted white precipitate filtered off and the filtrate concentrated to dryness. The crude mixture was dissolved in DCM (50 mL) and washed successively with Sat $NaHCO_3$ (2×25 mL) and brine (25 mL). The organic layer was dried through $MgSO_4$ and then organic layer was concentrated under rotary evaporation. The crude reaction mixture was subjected flash column chromatography on silica gel using 10% MeOH/DCM to get the product 2.
Synthesis of Compound (4):

To a stirred solution of 3 (0.57 g, 0.46 mmol) in dry DCM (20 mL) was added TFA (20 mL) and the resulted light brown reaction mixture was allowed to stir at rt for 4 h. The reaction progress was monitored by TLC. At which point DCM/TFA was completely removed under reduced pressure. The crude material directly used in the next without further purification.
Synthesis of Protected Ligand (5):

MAM acid (0.309 g, 1.25 mmol), TREN-Lys-$NH_2$ TFA (4, 0.79 g, 0.40 mmol), and DMAP (cat) were dissolved in dry DCM (40 mL). To this reaction mixture was added DIPEA (0.72 mL, g, 4.05 mmol) was added. The resulted reaction mixture was cooled to 0° C. and then TBTU (0.43 g, 1.33 mmol) was added. The resulted reaction mixture was allowed to stirred room temperature for 12 h. Then the DCM was completely removed. The crude material was subjected column chromatography on silica gel (DCM/MeOH, 90/10) to get desired amide tri-amide fractions of protected TREN-Lys-MAM.
Synthesis of TREN-Lys-MAM Ligand (6):

To 5 (0.1 g, 0.061 mmol) was added 6 mL of a 1:1 solution of concentrated HCl and glacial acetic acid. The suspension was stirred under $N_2$(g) for 40 h at room temperature. The reaction was co-evaporated with methanol (3×10 mL) and dried under vacuum to yield a light brown solid.
Synthesis of Gd-TREN-Lys-MAM:

To a stirred solution TREN-Lys-MAM (0.018 g, 0.019 mmol), in dry MeOH (6 mL) under Argon atmosphere was added $GdCl_3$ $6H_2O$ (0.007 g 0.020 mmol) in water (2 mL) followed by excess pyridine to maintain slightly basis pH of the reaction mixture. and the reaction turned to light orange opaque from a clear yellow solution. The reaction mixture was stirred at 60° C. for 40 h and then MeOH was completely concentrated under rotary evaporation. Complex was triturated with $Et_2O$ to yield light peach color solid.

TREN-Glu-MAM & Gd-TREN-Glu-MAM

Figure 11:
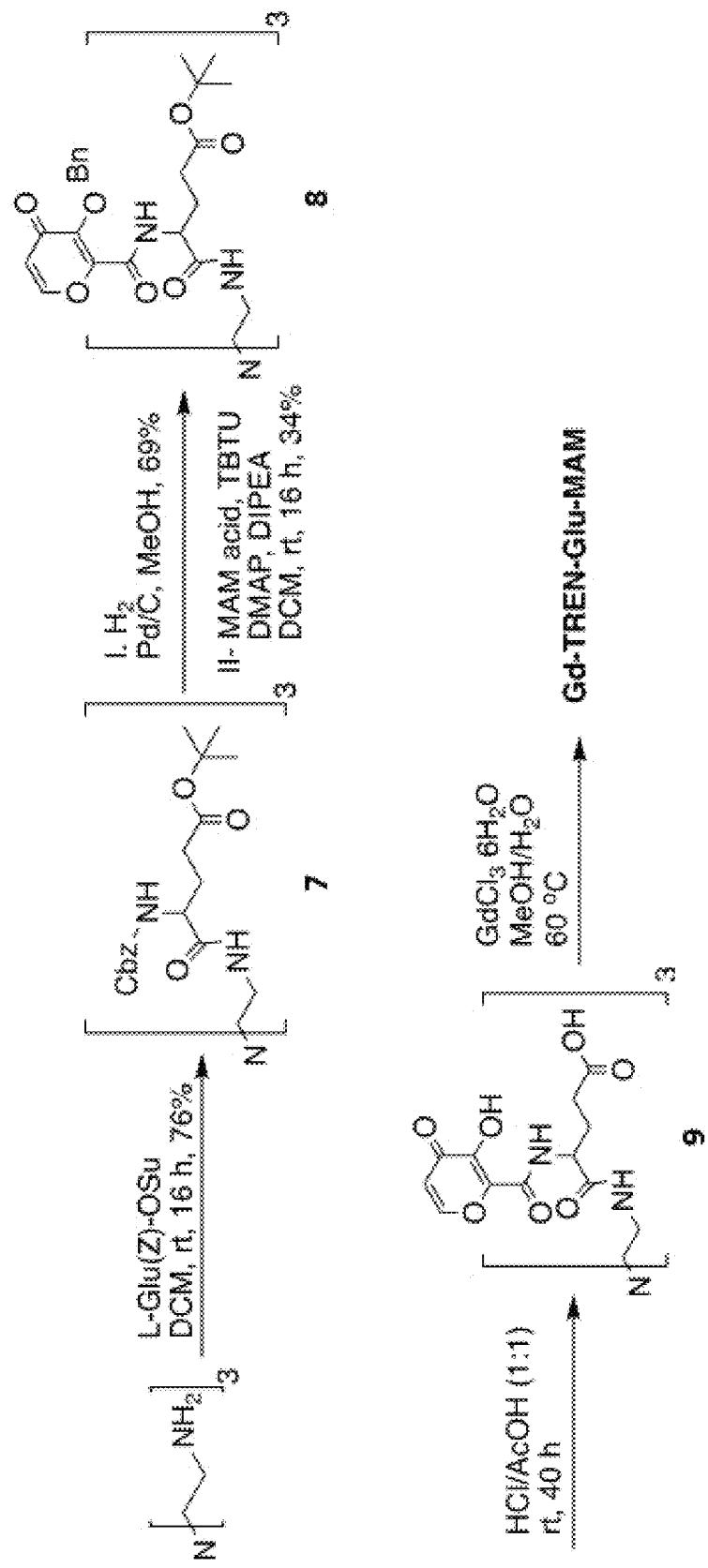
FIG. 11 shows a synthetic route for Gd-TREN-Glu-MAM.

A synthetic route for TREN-Glu-MAM & Gd-TREN-Glu-MAM is shown in FIG. 11.
Synthesis of TREN-(Z)-Glu-(OtBu) (7):

To a stirred solution of TREN (0.2 g, 1.36 mmol) in dry DCM (30 mL) was added Z-Glu-otBu)-OSu (1.84 g, 4.24 mmol) in dry DCM (15 mL) and the resulted reaction mixture was allowed to stir at rt for 16 h. The resulted white precipitate filtered off and the filtrate concentrated to dryness. The crude mixture was dissolved in DCM (50 mL) and washed successively with Sat NaHCO$_3$ (2×50 mL) and brine (50 mL). organic layer was dried through MgSO$_4$ and then organic layer was concentrated under rotary evaporation. The crude reaction mixture was subjected flash column chromatography on silica gel using 10% MeOH/DCM to get the product 7.

Synthesis of Protected Ligand (8):

To a stirred solution of 7 (0.8 g, 0.22 mmol) in dry MeOH (30 mL) was added 10 wt % Pd/C and applied to freeze-thaw-pump cycles and then Hz-gas at 3 atm was applied through parr hydrogenater and allowed to stir at rt for 12 h. Then the reaction was mixture was filtered through celite and then bed was celite bed was washed with MeOH (10 mL) and then MeOH was evaporated to get TREN-Glu-NHz.

MAM acid (0.108 g, 0.44 mmol), TREN-Glu-NH$_2$ (0.1 g, 0.14 mmol), and DMAP (cat) were dissolved in dry DCM (30 mL). To this reaction mixture was added DIPEA (0.15 mL, g, 0.85, mmol) was added. The resulted reaction mixture was cooled to 0° C. and then TBTU (0.151 g, 0.47 mmol) was added. The resulted reaction mixture was allowed to stirred room temperature for 12 h. Then the DCM was completely removed. The crude material was subjected column chromatography on silica gel (DCM/MeOH, 90/10) to get desired amide tri-amide fractions of protected TREN-Glu-MAM, 8.

Synthesis of TREN-Glu-MAM Ligand (9):

To 8 (0.2 g, 0.144 mmol) was added 8 mL of a 1:1 solution of concentrated HCl and glacial acetic acid. The suspension was stirred under N$_2$(g) for 40 h at room temperature. The reaction was co-evaporated with methanol (3×10 mL) and dried under vacuum to yield a light brown solid.

Synthesis of Gd-TREN-Glu-MAM:

To a stirred solution TREN-Glu-MAM (9, 0.025 g, 0.26 mmol), in dry MeOH (6 mL) under Argon atmosphere was added GdCl$_3$ 6H$_2$O (0.010 g 0.29 mmol) in water (2 mL) followed by excess pyridine to maintain slightly basis pH of the reaction mixture. and the reaction turned to light orange opaque from a clear yellow solution. The reaction mixture was stirred at 60° C. for 40 h and then MeOH was completely concentrated under rotary evaporation. Complex was triturated with Et$_2$O to yield light yellow color solid.

TREN-Gly-MAM & Gd-TREN-Gly-MAM

Figure 12:
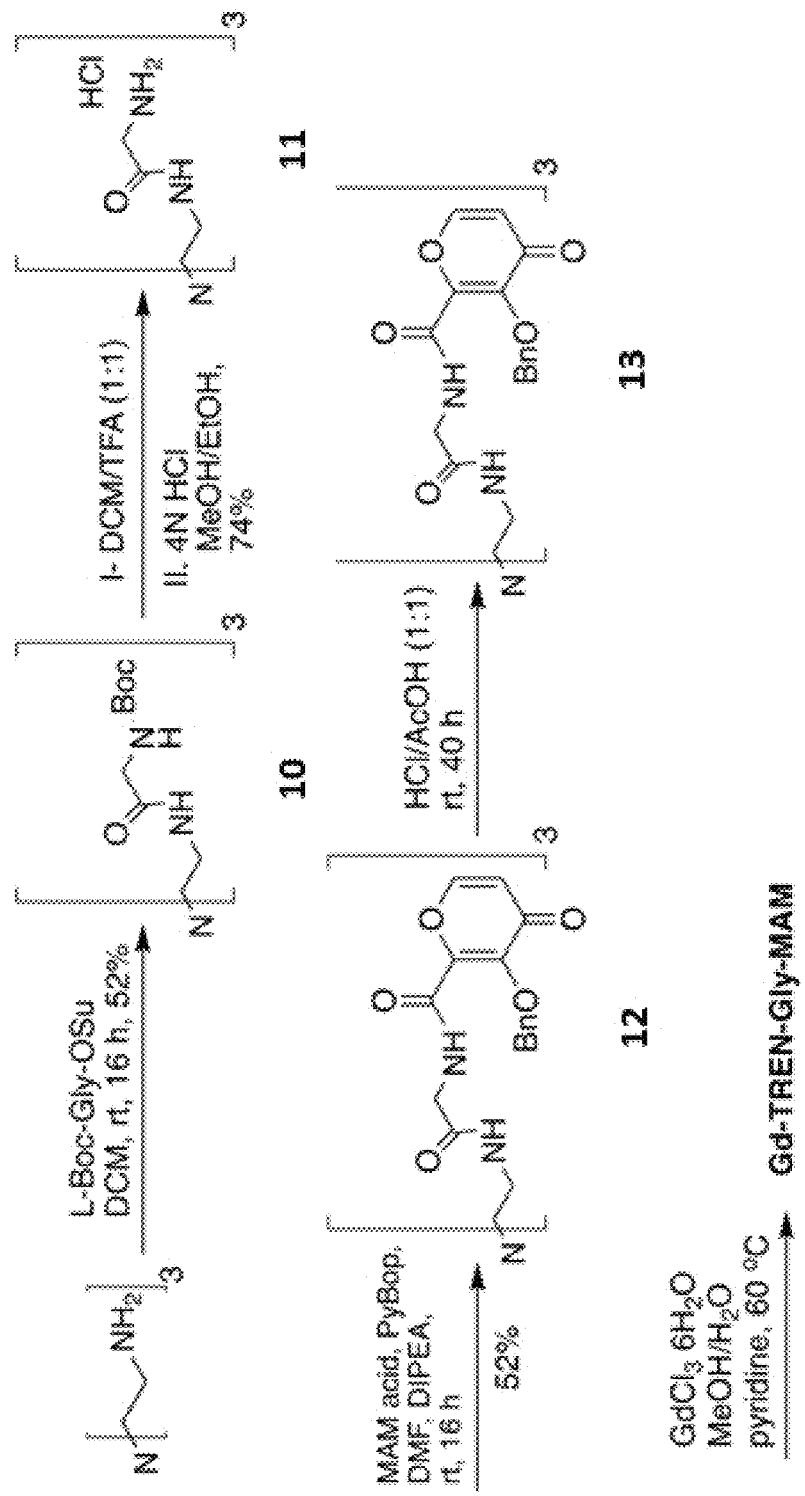
FIG. 12 shows a synthetic route for Gd-TREN-Gly-MAM.

A synthetic route for TREN-Gly-MAM & Gd-TREN-Gly-MAM is shown in FIG. 12.

Synthesis of TREN-Boc-Gly (10):

To a stirred solution of TREN (0.75 g, 5.12 mmol) in dry THF (20 mL) was added Boc-gly-OSu (4.40 g, 15.89 mmol) in dry THF (40 mL) and the resulted reaction mixture was allowed to stir at rt for 16 h. The resulted white precipitate filtered off and the filtrate concentrated to dryness. The crude mixture was dissolved in DCM (150 mL) and washed successively with Sat NaHCO$_3$ (2×75 mL) and brine (75 mL). organic layer was dried through MgSO$_4$ and then organic layer was concentrated under rotary evaporation. The crude reaction mixture was subjected flash column chromatography on silica gel using 10% MeOH/DCM to get the product 10.

$^1$H NMR (CDCl$_3$, 400 MHz): δ 7.39 (br, 3H, NH), 5.93 (br, 3H, NH), 3.79 (d, J=6.0 Hz, 6H), 3.28 (br, 6H), 2.65 (br, 6H), 1.40 (s, 9H) ppm.

Synthesis of N,N',N''-(nitrilotris(ethane-2,1-diyl))tris(2-aminoacetamide) hydrochloride salt (11):

To a stirred solution of 10 (1.0 g, 1.62 mmol) in dry DCM (20 mL) was added TFA (20 mL) and the resulted light brown reaction mixture was allowed to stir at rt for 4 h. The reaction progress was monitored by TLC. At which point DCM/TFA was completely removed under reduced pressure. The resulted thick brown sticky solution 4N HCl (20 mL) was added and stirred at rt for 30 min. The aqueous solution was completely concentrated under rotary evaporation. The resulted white sticky solid was dissolved in MeOH (10 mL) and the addition EtOH (50 mL) resulted white precipitated, then alcohol layer was decanted white solid further dried under vacuum to afforded compound as tetra HCl salt (0.55 g).

$^1$H NMR (D$_2$O, 400 MHz): δ 3.88 (s, 6H), 3.69 (t, J=6.4 Hz, 6H), 3.45 (t, J=6.4 Hz, 6H) ppm.

Synthesis of Protected Ligand (12):

MAM acid (0.16 g, 0.67 mmol), TREN-Gly-NH$_2$ HCl (0.1 g, 0.216 mmol), were dissolved in dry DMF (10 mL). To this reaction mixture was added DIPEA (0.35 mL, g, 1.95 mmol) was added. The resulted reaction mixture was cooled to 0° C. and then Pybop (0.372 g, 0.71 mmol) was added. The resulted reaction mixture was allowed to stirred room temperature for 12 h. Then the DMF was completely removed. The crude material was subjected column chromatography on silica gel (DCM/MeOH, 90/10) to get desired amide protected ligand 12.

Synthesis of TREN-Gly-MAM ligand (13):

To 12 (0.1 mg, 0.099 mmol) was added 8 mL of a 1:1 solution of concentrated HCl and glacial acetic acid. The suspension was stirred under N$_2$(g) for 24 h at room temperature. The reaction was co-evaporated with methanol (3×10 mL) and dried under vacuum to yield a light brown solid.

Synthesis of Gd-TREN-Gly-MAM:

To a stirred solution TREN-Gly-MAM (13, 0.030 g, 0.04 mmol), in dry MeOH (5 mL) under Argon atmosphere was added GdCl$_3$ 6H$_2$O (15.5 mg 0.04 mmol) followed by few drops of pyridine to maintain slightly basis pH of the reaction mixture. and the reaction turned to light orange opaque from a clear yellow solution. The reaction mixture was stirred at 60° C. for 40 h and then MeOH was completely concentrated under rotary evaporation and further triturated with Et$_2$O to afford final metal complex.

3,3-Li-HOPO-Lys-HOPO

Figure 13:
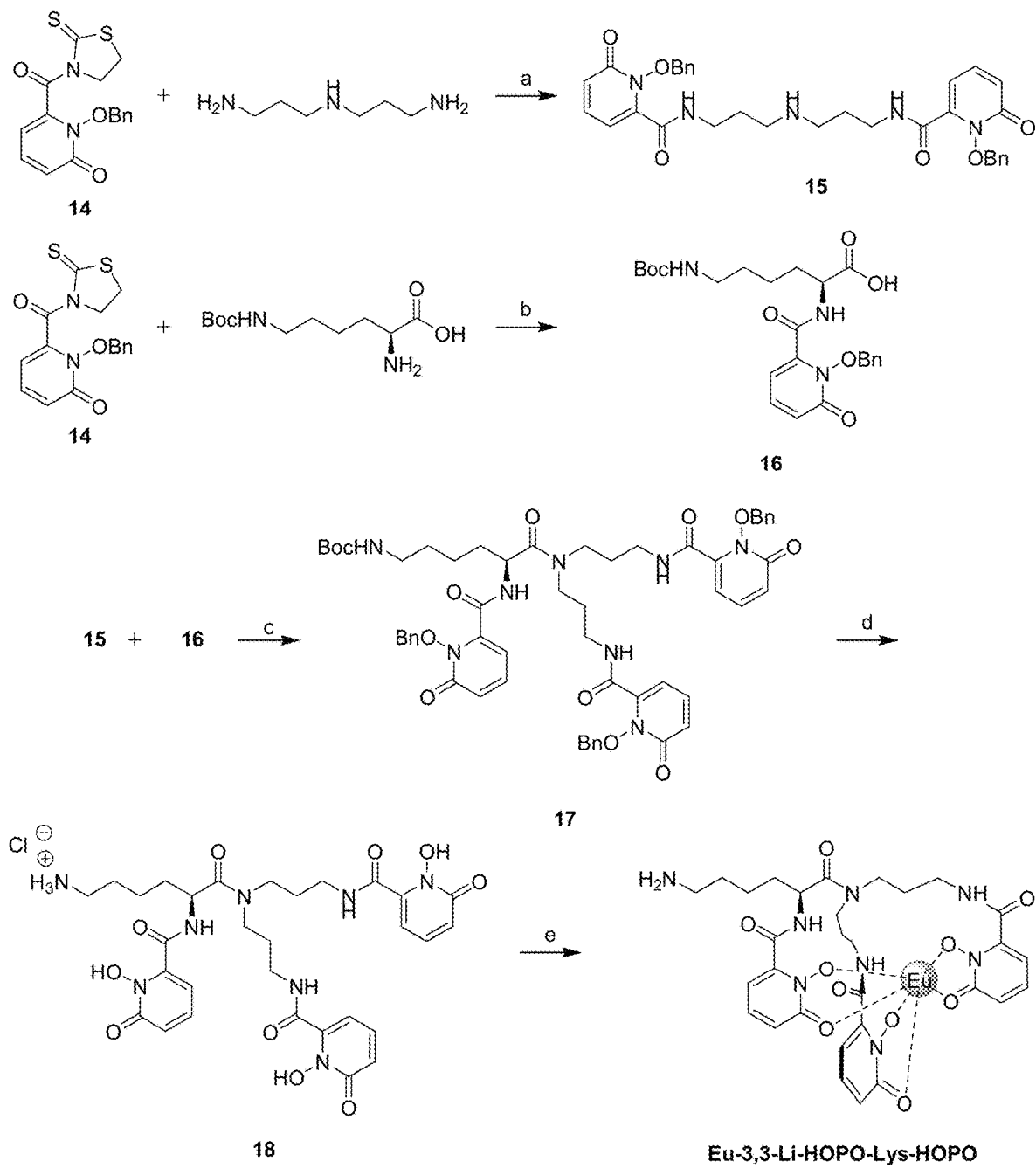
FIG. 13 shows a synthetic route for Eu-3,3-Li-HOPO-Lys-HOPO.

A synthetic route for 3,3-Li-HOPO-Lys-HOPO is shown in FIG. 13. 1-(benzyloxy)-6-(2-thioxothiazolidine-3-carbonyl)pyridin-2(1H)-one (14). Benzyl-protected 1,2-HOPO was synthesized as previously reported[76] with successful synthesis confirmed by $^1$H NMR and LR ESI-MS.

N,N'-(Azanediylbis(propane-3,1-diyl))bis(1-(benzyloxy)-6-oxo-1,6-dihydropyridine-2-carboxamide) (15).

Triethylamine (101 µL, 0.720 mmol) was added to a solution of the protected 1,2-HOPO(Bn) (14, 250 mg, 0.72 mmol) and bis(3-aminopropyl)amine) (47 mg, 0.36 mmol) in CH$_2$Cl$_2$ (5 mL). The reaction mixture was stirred at room temperature overnight. The solvents were removed under reduced pressure and the crude product was purified by flash chromatography over silica using 86.5% CH$_2$Cl$_2$/12.5% CH$_3$OH/1% NEt$_3$ as an eluent. The solvents were removed under reduced pressure to yield the amine intermediate 15 as a colorless oil (206 mg, 98%). $^1$H-NMR (400 MHz, CDCl$_3$): δ=8.08 (bs, 2H), 7.41-7.20 (m, 12H), 6.62 (dd, =7 Hz, J$_2$=2 Hz, 2H), 6.34 (dd, =7 Hz, J$_2$=2 Hz, 2H), 5.18 (s, 4H), 3.25 (m, 4H), 2.35-2.32 (m, 4H), 1.47-1.41 (m, 4H). $^{13}$C-NMR (100 MHz, CDCl$_3$): δ=160.2, 158.6, 143.0, 138.3, 133.3, 130.3, 129.4, 128.6, 123.7, 106.1, 79.3, 47.5, 39.1, 28.4. ESI-MS: m/z=586.8 ([M+H]$^+$), (Calcd. 586.3).

N$^2$-(1-(Benzyloxy)-6-oxo-1,6-dihydropyridine-2-carbonyl)-N$^6$-(tert-butoxycarbonyl)-L-lysine (16).

Triethylamine (201 µL, 1.44 mmol) was added to a solution of the benzyl protected 1,2-HOPO 14 (500 mg, 1.44 mmol) and H-Lys(Boc)-OH (355 mg, 1.44 mmol) in $CH_3CN$ (20 mL). The reaction mixture was stirred at room temperature overnight. The solvents were then removed under reduced pressure and the crude product was purified by flash chromatography over silica using 92.5% $CH_2Cl_2$/7% $CH_3OH$/0.5% $CH_3CO_2H$ as an eluent. The solvents were removed under reduced pressure to yield the intermediate 16 as a colorless oil (511 mg, 75%). $^1$H-NMR (400 MHz, $CDCl_3$): δ=7.73 (d, J=7 Hz, 1H), 7.44 (b, 2H), 7.29-7.24 (m, 3H), 6.73 (d, J=9 Hz, 1H), 6.45 (d, J=6 Hz, 1H), 5.34 (d, J=8 Hz, 1H), 5.21 (d, J=8 Hz, 1H), 4.57 (m, 1H), 2.90 (b, 2H), 1.83 (b, 1H), 1.67 (b, 1H), 1.41-1.27 (m, 13H). $^{13}$C-NMR (100 MHz, $CDCl_3$): δ=173.9, 159.9, 159.1, 158.0, 156.3, 142.1, 138.5, 133.1, 130.2, 129.4, 128.5, 124.0, 107.3, 81.0, 79.4, 79.3, 52.9, 41.0, 39.9, 31.2, 29.4, 29.0, 28.4, 22.4. ESI-MS: m/z=472.2 ($[M-H]^-$), (Calcd. 472.2).

tert-Butyl (S)-(5-(1-(benzyloxy)-6-oxo-1,6-dihydropyridine-2-carboxamido)-6-(bis(3-(1-(benzyloxy)-6-oxo-1,6-dihydropyridine-2-carboxamido)propyl)amino)-6-oxohexyl)carbamate (17).

Triethylamine (64 μL, 0.47 mmol) and O-(7-azabenzotriazol-1-yl)-N,N,N',N'-tetramethyluronium hexafluorophosphate (HATU, 178 mg, 0.469 mmol) were added to a solution of the amine intermediate 15 (275 mg, 0.469 mmol) and the acid intermediate 16 (221 mg, 0.469 mmol) in $CH_2Cl_2$ (10 mL). The reaction mixture was stirred at room temperature for 6 hours. The reaction mixture was then washed with 1 M HCl (aq) (3×10 mL) and $NaHCO_3$ (aq) (10%) (3×10 mL). The organic phase was dried with anhydrous $MgSO_4$ (s) and filtered. The solvent was removed under reduced pressure and the crude product was purified by flash chromatography over silica using 93% $CH_2Cl_2$/7% $CH_3OH$ as an eluent. The solvents were removed under reduced pressure to yield the protected ligand 17 as a colorless foam (150 mg, 30%). $^1$H-NMR (400 MHz, $CDCl_3$): δ=7.87 (s, 1H), 7.86 (s, 1H), 7.55-7.32 (m, 18H), 6.59 (t, J=8 Hz, 3H), 6.29 (t, J=8 Hz, 3H), 5.38-4.80 (m, 6H), 4.80 (b, 1H), 3.39-2.92 (m, 10H), 2.50 (s, 1H), 1.81 (b, 1H), 1.59-1.53 (m, 5H), 1.36 (b, 13H). $^{13}$C-NMR (100 MHz, $CDCl_3$): δ=171.4, 161.1, 160.6, 160.3, 158.6, 158.5, 158.3, 156.3, 143.2, 143.1, 141.6, 138.4, 138.3, 137.9, 133.4, 133.3, 130.7, 130.4, 130.1, 129.9, 129.6, 129.5, 129.3, 128.6, 128.6, 128.5, 124.5, 123.7, 123.6, 106.4, 105.3, 104.7, 79.7, 79.4, 79.0, 53.5, 50.4, 49.8, 44.0, 42.4, 39.9, 36.6, 32.2, 29.6, 28.4, 27.5, 26.7, 22.6. ESI-MS: m/z=1063.7 ($[M+Na]^+$), (Calcd. 1063.5).

(S)-6-(bis(3-(1-hydroxy-6-oxo-1,6-dihydropyridine-2-carboxamido)propyl)amino)-5-(1-hydroxy-6-oxo-1,6-dihydropyridine-2-carboxamido)-6-oxohexan-1-aminium chloride (3,3-Li-HOPO-Lys-HOPO).

The protected ligand 17 (116 mg, 0.114 mmol) was dissolved in a 1:1 mixture of HCl (aq) (1.0 M) and $CH_3CO_2H$ (6.7 mL). The reaction mixture was stirred at room temperature overnight. The volatiles were removed under reduced pressure. Addition of methanol-diethyl ether solution (1:1, 10 ml) resulted in a precipitate that was filtered and dried in a desiccator, yielding the deprotected ligand 18 as a beige solid (78 mg, 99%). $^1$H-NMR (400 MHz, $CD_3OD$): δ=7.25 (b, 3H), 6.48-6.41 (b, 6H), 4.65 (b, 1H), 3.30-2.97 (m, 8H), 2.65 (b, 2H), 1.75-1.66 (m, 2H), 1.56-1.52 (m, 4H), 1.44-1.42 (m, 2H), 1.23 (m, 2H). $^{13}$C-NMR (100 MHz, $CDCl_3$): δ=173.2, 162.6, 162.3, 161.9, 160.2, 142.6, 142.5, 142.0, 140.1, 139.7, 139.4, 129.8, 129.8, 129.4, 120.7, 120.5, 110.2, 109.6, 109.4, 51.5, 47.1, 47.0, 45.0, 40.8, 40.7, 38.5, 32.9, 29.8, 28.3, 23.9. IR (NaCl pellet, $cm^{-1}$): ν=3424, 2079, 1643. ESI-MS: m/z=671.5 ($[M+H]^+$), (Calcd. 671.3).

Eu-3,3-Li-HOPO-Lys-HOPO.

The deprotected ligand 3,3-Li-HOPO-Lys-HOPO (18, 80. mg, 0.11 mmol) and $EuCl_3.6H_2O$ (41 mg, 0.11 mmol) were dissolved in $CH_3OH$ and $H_2O$ mixture (2.5/2.5 mL), followed by addition of pyridine (80 μL). The reaction mixture was stirred at 80° C. for 8 hours. The mixture was cooled down to room temperature and centrifuged (2000 RPM, 5 minutes). The precipitate was decanted and dried in a desiccator to yield the Eu(III) complex as a beige powder (46 mg, 50%). IR (NaCl, $cm^{-1}$): ν=3571, 3500, 1647, 1610, 1365, 1289. ESI-MS: m/z=821.2 ($[M+2H]^{2+}$), (Calcd. 821.2).

Synthesis Gd-TREN-HMA

Figure 14:
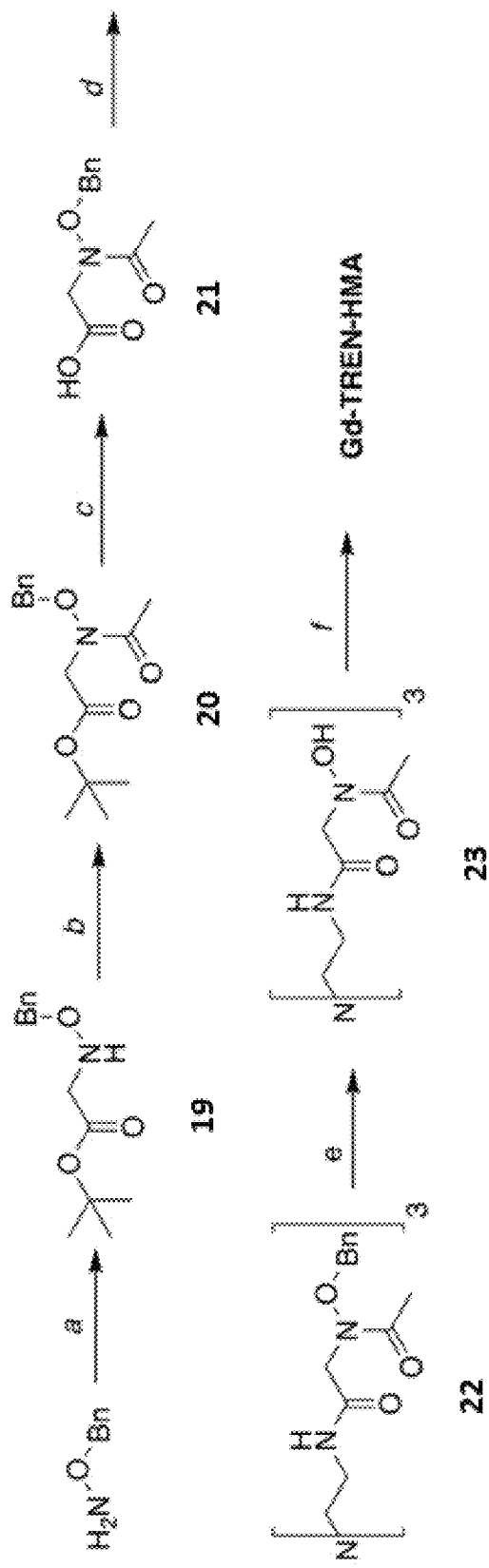
FIG. 14 shows a synthetic route for Gd-TREN-HMA.

A synthetic route for Gd-TREN-HMA is shown in FIG. 14.

Synthesis of tert-butyl (benzyloxy)glycinate (19):

To a stirred solution of $H_2N$-OBn1 (2.0 g, 16.24 mmol), in dry DMF (20 mL) wad added $K_2CO_3$. The resulted reaction mixture was stirred at rt for 20 min. Then tert-butyl 2-bromoacetate was added and resulted reaction mixture was stirred at rt for 16 h. The DMF was completely evaporated under u/Vacuum. The crude material was dissolved in EtOAc (100 mL) and washed successively with 0.1N HCl (2×50 mL), and brine (2×50 mL) then dried through $MgSO_4$ and concentrated under rotary evaporation to afford 3.7 g of 19 as light yellow liquid. Crude material was carried further without any further purification.

Synthesis of tert-butyl N-acetyl-N-(benzyloxy)glycinate (20):

To a stirred solution of 19 (2.0 g, 8.43 mmol) in dry EtOAC (30 mL) was added TEA (5.3 mL, 37.9 mmol) and the resulted reaction mixture was cooled to 0° C. Then to this AcCL (1.8 mL, 25.2 mmol) was added dropwise over a period of 10 min. the resulted reaction mixture was allowed stir at 0° C. for 5 h and then further allowed to stir at rt for an additional 7 h. Then EtOAC was completely removed and the crude material was dissolved in DCM (100 mL) and washed successively with 5% NaOH (2×50 mL), 0.1N HCl (2×50 mL), and brine (2×50 mL) then dried through $MgSO_4$ and concentrated under rotary evaporation to afford 2.05 g of 20 as light brown low melting solid.

$^1$H NMR ($D_2O$, 400 MHz): δ 3.88 (s, 6H), 3.69 (t, J=6.4 Hz, 6H), 3.45 (t, J=6.4 Hz, 6H) ppm.

Synthesis of N-acetyl-N-(benzyloxy)glycine (21):

To a stirred solution of 20 (2.1 g, 7.52 mmol) in dry DCM (210 mL) was added TFA (10 mL) and the resulted light brown reaction mixture was allowed to stir at rt for 4 h. The reaction progress was monitored by TLC. At which point DCM/TFA was completely removed under reduced pressure. The crude material carried further without any purification.

Synthesis of N,N',N"-(nitrilotris(ethane-2,1-diyl))tris(2-(N-(benzyloxy)acetamido)acetamide)(22):

Compound 21 (1.92 g, 8.61 mmol), TREN-(0.40 g, 2.73 mmol), and DMAP (0.045 g, 0.41 mmol) were dissolved in dry DCM (80 mL). To this reaction mixture was added DIPEA (2.94 mL, g, 16.4 mmol) was added. The resulted reaction mixture was cooled to 0° C. and then TBTU (2.76 g, 8.61 mmol) was added. The resulted reaction mixture was allowed to stirred room temperature for 12 h. Then organic layer was washed successively with Sat $NaHCO_3$ (2×50 mL), and brine (50 mL). Organic layer was dried through $MgSO_4$ and concentrated under rotary evaporation. The crude material was subjected column chromatography on silica gel (DCM/MeOH, 90/10) to get desired amide triamide fractions 21.

Synthesis of N,N',N"-(nitrilotris(ethane-2,1-diyl))tris(2-(N hydroxyacetamido)acetamide) TREN-HMA (23):

To a stirred solution of 22 (0.25 g, 0.32 mmol) in dry MeOH (20 mL0 was added 10 wt % Pd/C and applied to freeze-thaw-pump cycles and then H$_2$-gas at 3 atm was applied through parr hydrogenater and allowed to stir at rt for 12 h. Then the reaction was mixture was filtered through celite and then bed was celite bed was washed with MeOH (10 mL) and then MeOH was evaporated to get TREN-HMA (23).

Synthesis of Gd-TREN-HMA:

To a stirred solution TREN-HMA (23, 0.045 g, 16.24 mmol), in dry MeOH (5 mL) under Argon atmosphere was added GdCl$_3$·6H$_2$O and the reaction turned to light pink opaque from a clear yellow solution. The reaction mixture was stirred at rt for 3 h and then MeOH was completely concentrated under rotary evaporation and crude material was further triturated with Et$_2$O to afford final metal complex.

The ability of exemplified complexes to capture phosphates with high affinity and selectivity directly in water at neutral pH and release them under acidic conditions was evaluated with Gd-TREN-MAM. This model lanthanide complex has two open coordination sites that at neutral pH are filled with water molecules. In water at neutral pH, Gd-TREN-MAM binds phosphate with high affinity ($K_a=1.3\times10^4$) via the formation of a ternary complex in which one phosphate replaces both inner-sphere water molecules. The formation of this complex is highly pH dependent; the phosphate is completely released from Gd-TREN-MAM below pH 2. Since the Gd$^{III}$ ion remains complexed by its ligand even under strong acidic conditions, Gd-TREN-MAM can be used at least ten times in a pH-based recycling scheme that enables catch-and-release of one phosphate per cycle. Gd-TREN-MAM is highly selective for phosphate over other anions of environmental concerns, including HCO$_3^-$, HCO$_2^-$, CH$_3$CO$_2^-$, SO$_4^{2-}$, NO$_3^-$, NO$_2^-$, BrO$_3^-$, AsO$_4^-$, F$^-$, Cl$^-$, Br$^-$ and to a lesser extent, ClO$_3^-$. The development of such receptors that bind phosphate reversibly in a pH dependent manner opens the possibility to design catch-and-release systems for the purification of surface waters.

TABLE 1

Affinity of lanthanide complexes for H$_2$PO$_4^-$/HPO$_4^{2-}$ at neutral pH in water at 25° C.

| | $K_a$ (M$^{-1}$) |
|---|---|
| Gd-TREN-MAM | >10,000 |
| Gd-TREN-Gly-MAM | >5,000 |
| Gd-TREN-Glu-MAM | >10 |
| Gd-TREN-Lys-MAM | >20,000 |
| Gd-TREN-1,2-HOPO | >10,000 |
| Eu-3,3-Li-HOPO-Lys-HOPO | >50,000 |
| Gd-TREN-HMA | >5,000 |
| Gd-TREN-HPA | >5,000 |

Figure 15:
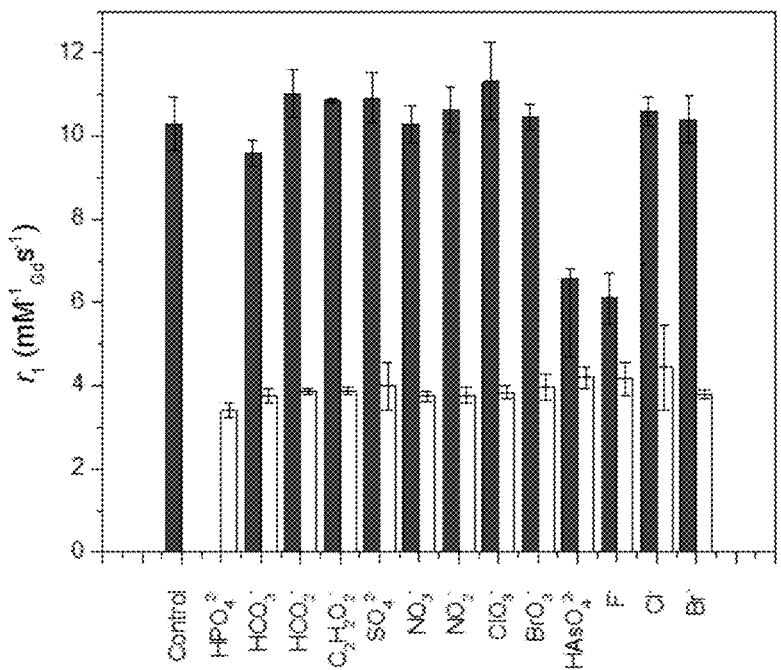
FIG. 15 shows the selectivity of Gd-TREN-1,2-HOPO (control) to anions. Black bars represent the longitudinal relaxivity after addition of an excess at 300 eq. of the appropriate anion (15 mM $NaHCO_3$, $NaHCO_2$, $K(C_2H_3O_2)$, $K_2SO_4$, $Na(NO_3)$, $Na(NO_2)$, $KClO_3$, $NaBrO_3.2H_2O$, $Na_2H(AsO_4).7H_2O$, $KF.2H_2O$, $KCl$, $NaBr.2H_2O$). White bars represent $r_1$ after subsequent addition of 15 mM $K_2H(PO_4).H_2O$. Experimental conditions: [Gd-TREN-1,2-HOPO]=50 µM in 50 mM HEPES (aq), pH 7.4, T=25° C. Anion salts: $K_2H(PO_4).H_2O$. Error bars represent standard deviations (n=3).

FIG. 15 shows the selectivity of Gd-TREN-1,2-HOPO (control) to anions. Black bars represent the longitudinal relaxivity after addition of an excess at 300 eq. of the appropriate anion (15 mM NaHCO$_3$, NaHCO$_2$, K(C$_2$H$_3$O$_2$), K$_2$SO$_4$, Na(NO$_3$), Na(NO$_2$), KClO$_3$, NaBrO$_3$·2H$_2$O, Na$_2$H(AsO$_4$)·7H$_2$O, KF·2H$_2$O, KCl, NaBr·2H$_2$O). White bars represent r$_1$ after subsequent addition of 15 mM K$_2$H(PO$_4$)·H$_2$O. Experimental conditions: [Gd-TREN-1,2-HOPO]=50 μM in 50 mM HEPES (aq), pH 7.4, T=25° C. Anion salts: K$_2$H(PO$_4$)·H$_2$O. Error bars represent standard deviations (n=3).

Figure 16:
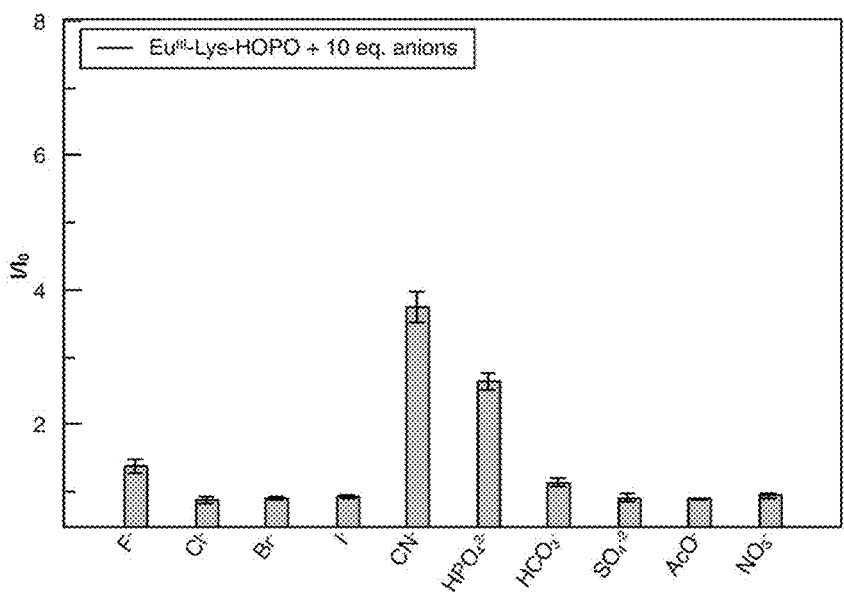
FIG. 16 shows the selectivity of Eu-3,3-Li-HOPO-Lys-HOPO to anions. Bars represent the increase in time-gated luminescence intensity at 545 nm after addition of an excess at 10 eq. of the appropriate anion ($KF.2H_2O$, $KCl$, $NaBr.2H_2O$, $KI$, $KCN$ $K_2H(PO_4).H_2O$, $NaHCO_3$, $NaHCO_2$, $K(C_2H_3O_2)$, $K_2SO_4$, $Na(NO_3)$,). Error bars represent standard deviations (n=3).

FIG. 16 shows the selectivity of Eu-3,3-Li-HOPO-Lys-HOPO to anions. Bars represent the increase in time-gated luminescence intensity at 545 nm after addition of an excess at 10 eq. of the appropriate anion (KF·2H$_2$O, KCl, NaBr·2H$_2$O, KI, KCN K$_2$H(PO$_4$)·H$_2$O, NaHCO$_3$, NaHCO$_2$, K(C$_2$H$_3$O$_2$), K$_2$SO$_4$, Na(NO$_3$),). Error bars represent standard deviations (n=3).

Abbreviations $K_a$—association constant, EPA—Environmental Protection Agency, MRI—Magnetic Resonance Imaging, DO3A—2,2',2"-(1,4,7,10-tetraazacyclododecane-1,4,7-triyl)triacetic acid, DTPA—2,2',2",2"-((((carboxymethyl)azanediyl)bis(ethane-2,1-diyl))bis(azanetriyl))tetraacetic acid, TREN-bisHOPO-TAM-dPEG4—N$_1$-(2-(bis(2-(3-hydroxy-1-methyl-2-oxo-1,2-dihydropyridine-4-carboxamido)ethyl)amino)ethyl)-2,3-dihydroxy-N4-(methoxymethyl)terephthalamide, TREN-bisHOPO-TAM—N$_3$—N$_1$-(2-(bis(2-(3-hydroxy-1-methyl-2-oxo-1,2-dihydropyridine-4-carboxamido)ethyl)amino)ethyl)-N$_4$-(2-(bis(aminomethyl)amino)ethyl)-2,3-dihydroxyterephthalamide, APCI—Atmospheric Pressure Chemical Ionization, T$_1$—longitudinal relaxation time, T$_2$—transverse relaxation time, [Gd]—concentration of gadolinium, r$_1$—longitudinal relaxivity, r$_2$—transverse relaxivity, c—molal concentration, q—hydration number, B$_0$—magnetic field strength, PRE—proton relaxation enhancement, HEPES—2-[4-(2-hydroxyethyl)piperazin-1-yl]ethanesulfonic acid, MOPSO—β-Hydroxy-4-morpholinepropanesulfonic acid, 3-Morpholino-2-hydroxypropanesulfonic acid, y—observed relaxation rates, C$_f$—paramagnetic complex concentration, x—concentration of biphosphate, R$_f$—relaxivity of the free unbound complex, R$_b$—relaxivity of the phosphate bound complex, n—number of binding sites.

REFERENCES

1. Cordell, D.; Drangert, J. O.; White, S., The story of phosphorus: Global food security and food for thought. *Global Environ. Chang.* 2009, 19, 292-305.
2. Schindler, D. W.; Carpenter, S. R.; Chapra, S. C.; Hecky, R. E.; Orihel, D. M., Reducing Phosphorus to Curb Lake Eutrophication is a Success. *Environ. Sci. Technol.* 2016, 50, 8923-8929.
3. Pelley, J., Taming Toxic Algae Blooms. *ACS Cent. Sci.* 2016, 2, 270-273.
4. Jetoo, S.; Grover, V. I.; Krantzberg, G., The Toledo Drinking Water Advisory: Suggested Application of the Water Safety Planning Approach. *Sustainability* 2015, 7, 9787-9808.
5. Mapare, S. V.; Yu, P. L.; Sarkar, A.; Mukhopadhyay, S. C., A Review of Sensor Technology for In-field Phosphate monitoring. *Int. Conf. Sens. Technol.* 2013, 411-418.
6. Le Cone, K. S.; Valsami-Jones, E.; Hobbs, P.; Parsons, S. A., Phosphorus Recovery from Wastewater by Struvite Crystallization: A Review. *Crit. Rev. Env. Sci. Technol.* 2009, 39, 433-477.
7. Ueno, Y.; Fujii, M., Three Years Experience of Operating and Selling Recovered Struvite from Full-Scale Plant. *Environ. Technol.* 2001, 22, 1373-1381.
8. Mehta, C. M.; Khunjar, W. O.; Nguyen, V.; Tait, S.; Batstone, D. J., Technologies to Recover Nutrients from Waste Streams: A Critical Review. *Crit. Rev. Environ. Sci. Technol.* 2015, 45, 385-427.

9. Donatello, S.; Cheeseman, C. R., Recycling and recovery routes for incinerated sewage sludge ash (ISSA): A review. *Waste Manage.* 2013, 33 (11), 2328-2340.
10. Kunz, W.; Henle, J.; Ninham, B. W., 'Zur Lehre von der Wirkung der Salze' (about the science of the effect of salts): Franz Hofmeister's historical papers. *Curr. Opin. Colloid Interface Sci.* 2004, 9, 19-37.
11. Zhang, Y. J.; Cremer, P. S., Interactions between macromolecules and ions: the Hofmeister series. *Curr. Opin. Chem. Biol.* 2006, 10, 658-663.
12. Bhattacharyya, D.; Hestekin, J. A.; Brushaber, P.; Cullen, L.; Bachas, L. G.; Sikdar, S. K., Novel poly-glutamic acid functionalized microfiltration membranes for sorption of heavy metals at high capacity. *J. Membr. Sci* 1998, 141, 121-135.
13. Konishi, S.; Saito, K.; Furusaki, S.; Sugo, T., Sorption Kinetics of Cobalt in Chelating Porous Membrane. *Ind. Eng. Chem. Res.* 1992, 31, 2722-2727.
14. Li, G. Q.; Konishi, S.; Saito, K.; Sugo, T., High Collection Rate of Pd in Hydrochloric-Acid Medium Using Chelating Microporous Membrane. *J. Membr. Sci.* 1994, 95, 63-69.
15. Tsuneda, S.; Saito, K.; Furusaki, S.; Sugo, T.; Okamoto, J., Metal Collection Using Chelating Hollow Fiber Membrane. *J. Membr. Sci.* 1991, 58, 221-234.
16. Chouyyok, W.; Wiacek, R. J.; Pattamakomsan, K.; Sangvanich, T.; Grudzien, R. M.; Fryxell, G. E.; Yantasee, W., Phosphate Removal by Anion Binding on Functionalized Nanoporous Sorbents. *Environ. Sci. Technol.* 2010, 44 (8), 3073-3078.
17. Choi, J. W.; Lee, S. Y.; Chung, S. G.; Hong, S. W.; Kim, D. J.; Lee, S. H., Removal of Phosphate from Aqueous Solution by Functionalized Mesoporous *Materials. Water Air Soil Pollut.* 2011, 222 (1-4), 243-254.
18. Biswas, B. K.; Inoue, K.; Ghimire, K. N.; Harada, H.; Ohto, K.; Kawakita, H., Removal and recovery of phosphorus from water by means of adsorption onto orange waste gel loaded with zirconium. *Bioresource Technol.* 2008, 99 (18), 8685-8690.
19. Yeon, K. H.; Park, H.; Lee, S. H.; Park, Y. M.; Lee, S. H.; Iwamoto, M., Zirconium mesostructures immobilized in calcium alginate for phosphate removal. *Korean J. Chem. Eng.* 2008, 25 (5), 1040-1046.
20. Ou, E.; Junjie, Z. J.; Shaochun, M. C.; Jiaqiang, W. Q.; Fei, X.; Liang, M., Highly efficient removal of phosphate by lanthanum-doped mesoporous SiO2. *Colloid Surf. A.* 2007, 308 (1-3), 47-53.
21. Wu, R. S. S.; Lam, K. H.; Lee, J. M. N.; Lau, T. C., Removal of phosphate from water by a highly selective La(III)-chelex resin. *Chemosphere* 2007, 69 (2), 289-294.
22. Ping, N.; Bart, H. J.; Bing, L.; Lu, X. W.; Zhang, Y., Phosphate removal from wastewater by model-La(III) zeolite adsorbents. *J. Environ. Sci-China* 2008, 20 (6), 670-674.
23. Fryxell, G. E.; Liu, J.; Hauser, T. A.; Nie, Z. M.; Ferris, K. F.; Mattigod, S.; Gong, M. L.; Hallen, R. T., Design and synthesis of selective mesoporous anion traps. *Chem. Mater.* 1999, 11 (8), 2148-2154.
24. Xue, Y. J.; Hou, H. B.; Zhu, S. J., Characteristics and mechanisms of phosphate adsorption onto basic oxygen furnace slag. *J. Hazard. Mat.* 2009, 162 (2-3), 973-980.
25. Zhang, G. S.; Liu, H. J.; Liu, R. P.; Qu, J. H., Removal of phosphate from water by a Fe—Mn binary oxide adsorbent. *J. Colloid Interface Sci.* 2009, 335 (2), 168-174.
26. Xiong, J. B.; He, Z. L.; Mahmood, Q.; Liu, D.; Yang, X.; Islam, E., Phosphate removal from solution using steel slag through magnetic separation. *J. Hazard. Mater.* 2008, 152 (1), 211-215.
27. Huang, W. W.; Wang, S. B.; Zhu, Z. H.; Li, L.; Yao, X. D.; Rudolph, V.; Haghseresht, F., Phosphate removal from wastewater using red mud. *J. Hazard. Mater.* 2008, 158 (1), 35-42.
28. Zeng, L.; Li, X. M.; Liu, J. D., Adsorptive removal of phosphate from aqueous solutions using iron oxide tailings. *Water Re.s* 2004, 38 (5), 1318-1326.
29. Jeon, D. J.; Yeom, S. H., Recycling wasted biomaterial, crab shells, as an adsorbent for the removal of high concentration of phosphate. *Bioresource Technol.* 2009, 100 (9), 2646-2649.
30. Hatai, J.; Pal, S.; Bandyopadhyay, S., An inorganic phosphate (P-i) sensor triggers 'turn-on' fluorescence response by removal of a $Cu^{2+}$ ion from a $Cu^{2+}$-ligand sensor: determination of P-i in biological samples. *Tetrahedron Lett.* 2012, 53, 4357-4360.
31. Suganya, S.; Velmathi, S.; Venkatesan, P.; Wu, S. P.; Boobalan, M. S., A highly fluorescent zinc complex of a dipodal N-acyl hydrazone as a selective sensor for $H_2PO_4^-$ ions and application in living cells. *Inorg. Chem. Front.* 2015, 2, 649-656.
32. Jiang, S. Q.; Zhou, Z. Y.; Zhuo, S. P.; Shan, G. G.; Xing, L. B.; Wang, H. N.; Su, Z. M., Rational design of a highly sensitive and selective "turn-on" fluorescent sensor for $PO_4^{3-}$ detection. *Dalton Trans.* 2015, 44, 20830-20833.
33. Smit, A. L. B., P. S; Schröder, J. J; Conijn, J. G.; van der Meer, H. G., Phosphorus in Agriculture: Global Resources, Trends and Developments. Steering Committee Technology Assessment of the Ministry of Agriculture, Nature, and Food Quality. Plant Research International B.V.: The Netherlands: Wagenigen University, 2009.
34. de-Bashan, L. E.; Bashan, Y., Recent advances in removing phosphorus from wastewater and its future use as fertilizer (1997-2003). *Water Res.* 2004, 38, 4222-4246.
35. Quality Criteria for Water, 1986. Agency, E. P., Ed. Office of Water Regulations and Standards: Washington, D.C., 1986.
36. Hargrove, A. E.; Nieto, S.; Zhang, T. Z.; Sessler, J. L.; Anslyn, E. V., Artificial Receptors for the Recognition of Phosphorylated Molecules. *Chem. Rev.* 2011, 111, 6603-6782.
37. Ikotun, 0. F.; Marino, N.; Kruger, P. E.; Julve, M.; Doyle, R. P., Coordination complexes incorporating pyrophosphate: Structural overview and exploration of their diverse magnetic, catalytic and biological properties. *Coord. Chem. Rev.* 2010, 254, 890-915.
38. Martinez-Peragon, A.; Miguel, D.; Orte, A.; Mota, A. J.; Ruedas-Rama, M. J.; Justicia, J.; Alvarez-Pez, J. M.; Cuerva, J. M.; Crovetto, L., Rational design of a new fluorescent 'ON/OFF' xanthene dye for phosphate detection in live cells. *Org. Biomol. Chem.* 2014, 12, 6432-6439.
39. Mummidivarapu, V. V. S.; Hinge, V. K.; Rao, C. P., Interaction of a dinuclear fluorescent Cd(II) complex of calix[4]arene conjugate with phosphates and its applicability in cell imaging. *Dalton Trans.* 2015, 44, 1130-1141.
40. Bansal, V. K., Serum Inorganic Phosphorus. In Clinical Methods: The History, Physical, and Laboratory Examinations., 3rd edition ed.; Walker, H. K.; Hall, W. D.; Hurst, J. W., Ed. Butterworths: Boston, 1990.

41. Hancock, R. D.; Martell, A. E., Ligand Design for Selective Complexation of Metal-Ions in Aqueous-Solution. *Chem. Rev.* 1989, 89, 1875-1914.
42. Han, M. S.; Kim, D. H., Naked-eye detection of phosphate ions in water at physiological pH: A remarkably selective and easy-to-assemble colorimetric phosphate-sensing probe. *Angew. Chem. Int. Ed.* 2002, 41, 3809-3811.
43. Murugavel, R.; Choudhury, A.; Walawalkar, M. G.; Pothiraja, R.; Rao, C. N. R., Metal complexes of organophosphate esters and open-framework metal phosphates: Synthesis, structure, transformations, and applications. *Chem. Rev.* 2008, 108, 3549-3655.
44. Liu, Y.; Sheng, X.; Dong, Y. H.; Ma, Y. J., Removal of high-concentration phosphate by calcite: Effect of sulfate and pH. *Desalination* 2012, 289, 66-71.
45. Bruce, J. I.; Dickins, R. S.; Govenlock, L. J.; Gunnlaugsson, T.; Lopinski, S.; Lowe, M. P.; Parker, D.; Peacock, R. D.; Perry, J. J. B.; Aime, S.; Botta, M., The selectivity of reversible oxy-anion binding in aqueous solution at a chiral europium and terbium center: Signaling of carbonate chelation by changes in the form and circular polarization of luminescence emission. *J. Am. Chem. Soc.* 2000, 122, 9674-9684.
46. Rudkevich, D. M.; Scheerder J.; Reinhoudt, D. N., Anion Recognition by Neutral Receptors In *Molecular Design and Bioorganic Catalyst*, Wilcok, C. S.; Hamilton, A. D., Ed. Kluwer Academic Publishers: Dordrecht, 1996; 137-159.
47. Weitz, E. A.; Chang, J. Y.; Rosenfield, A. H.; Pierre, V. C., A selective luminescent probe for the direct time-gated detection of adenosine triphosphate. *J. Am. Chem. Soc.* 2012, 134 (39), 16099-16102
48. Weitz, E. A.; Chang, J. Y.; Rosenfield, A. H.; Morrow, E. A.; Pierre, V. C., The basis for the molecular recognition and the selective time-gated luminescence detection of ATP and GTP by a lanthanide complex. *Chem. Sci.* 2013, 4 (10), 4052-4060
49. Andolina, C. M.; Morrow, J. R., Luminescence Resonance Energy Transfer in Heterodinuclear Ln(III) Complexes for Sensing Biologically Relevant Anions. *Eur. J. Inorg. Chem.* 2011, 1, 154-164.
50. Tobey, S. L.; Anslyn, E. V., Energetics of phosphate binding to ammonium and guanidinium containing metallo-receptors in water. *J. Am. Chem. Soc.* 2003, 125, 14807-14815.
51. Tobey, S. L.; Jones, B. D.; Anslyn, E. V., $C_{3v}$ symmetric receptors show high selectivity and high affinity for phosphate. *J. Am. Chem. Soc.* 2003, 125, 4026-4027.
52. Kubik, S., Anion recognition in water. *Chem. Soc. Rev.* 2010, 39, 3648-3663.
53. Grell, D.; Grell, E.; Bugnon, P.; Dietrich, B.; Lehn, J. M., Molecular ionics of anion receptor molecules—A microcalorimetric study. *J. Therm. Anal. calorim.* 2004, 77, 483-495.
54. Oton, F.; Tarraga, A.; Velasco, M. D.; Molina, P., A ferrocene-based heteroditopic ligand for electrochemical sensing of cations and anions. *Dalton Trans.* 2005, 7, 1159-1161.
55. Nieto, D.; Gonzalez-Vadillo, A. M.; Bruna, S.; Pastor, C. J.; Kaifer, A. E.; Cuadrado, I., Pt(II)-activated coupling of aminoethylferrocene with benzonitrile. A facile access route to a new redox-active bis(ferrocenyl-amidine) anion sensor. *Chem. Commun.* 2011, 47, 10398-10400.
56. Pramanik, A.; Das, G., An efficient phosphate sensor: tripodal quinoline excimer transduction. *Tetrahedron* 2009, 65, 2196-2200.
57. Merbach, H., Toth, The Chemistry of Contrast Agents in Medical Magnetic Resonance Imaging. Second Edition ed.; John Wiley & Sons Publication: United Kingdom, 2013.
58. Pierre, V. C.; Botta, M.; Aime, S.; Raymond, K. N., Substituent effects on Gd(III)-based MRI contrast agents: Optimizing the stability and selectivity of the complex and the number of coordinated water molecules. *Inorg. Chem.* 2006, 45, 8355-8364.
59. Burai, L.; Hietapelto, V.; Kiraly, R.; Toth, E.; Brucher, E., Stability constants and H-1 relaxation effects of ternary complexes formed between Gd-DTPA, Gd-DTPA-BMA, Gd-DOTA, and Gd-EDTA and citrate, phosphate, and carbonate ions. *Magn. Reson. Med.* 1997, 38, 146-150.
60. Caravan, P.; Ellison, J. J.; McMurry, T. J.; Lauffer, R. B., Gadolinium(III) chelates as MRI contrast agents: Structure, dynamics, and applications. *Chem. Rev.* 1999, 99, 2293-2352.
61. dos Santos, C. M.; Fernandez, P. B.; Plush, S. E.; Leonard, J. P.; Gunnlaugsson, T., Lanthanide luminescent anion sensing: evidence of multiple anion recognition through hydrogen bonding and metal ion coordination. *Chem. Commun.* 2007, 3389-3391.
62. Leonard, J. P.; dos Santos, C. M.; Plush, S. E.; McCabe, T.; Gunnlaugsson, T., pH driven self-assembly of a ternary lanthanide luminescence complex: the sensing of anions using a beta-diketonate-Eu(III) displacement assay. *Chem. Commun.* 2007, 129-131.
63. Puerta, D. T.; Botta, M.; Jocher, C. J.; Werner, E. J.; Avedano, S.; Raymond, K. N.; Cohen, S. M., Tris(pyrone) chelates of Gd(III) as high solubility MRI-CA. *J. Am. Chem. Soc.* 2006, 128, 2222-2223.
64. Xie, Y. Y.; Liu, M. S.; Hu, P. P.; Kong, X. L.; Qiu, D. H.; Xu, J. L.; Hider, R. C.; Zhou, T., Synthesis, physicochemical properties, and antimicrobial evaluation of a new series of iron(III) hexadentate chelators. *Med. Chem. Res.* 2013, 22 (5), 2351-2359.
65. Jocher, C. J.; Moore, E. G.; Pierce, J. D.; Raymond, K. N., Aqueous Ln(III) luminescence agents derived from a tasty precursor. Inorg. Chem. 2008, 47 (18), 7951-3
66. Botta, M., Second coordination sphere water molecules and relaxivity of gadolinium(III) complexes: Implications for MRI contrast agents. *Eur. J. Inorg. Chem.* 2000, 3, 399-407.
67. Swift, T. J.; Connick, R. E., NMR-Relaxation Mechanisms of O17 in Aqueous Solutions of Paramagnetic Cations and the Lifetime of Water Molecules in the First Coordination Sphere. *J. Chem. Phys.* 1962, 37, 307-320.
68. Aime, S.; Botta, M.; Fasano, M.; Crich, S. G.; Terreno, E., Gd(III) complexes as contrast agents for magnetic resonance imaging: A proton relaxation enhancement study of the interaction with human serum albumin. *J. Biol. Inorg. Chem.* 1996, 1, 312-319.
69. Svane, S.; Jorgensen, T. J. D.; McKenzie, C. J.; Kjeldsen, F., Effect of Metals in Biomimetic Dimetal Complexes on Affinity and Gas-Phase Protection of Phosphate Esters. *Anal. Chem.* 2015, 87, 7060-7068.
70. Thordarson, P., Determining association constants from titration experiments in supramolecular chemistry. *Chem. Soc. Rev.* 2011, 40 (3), 1305-1323.
71. Fernandez-Cornejo, J. N., R. ThWechsler, S.; Martin, A.; Vialou, A. *Pesticide Use in U.S. Agriculture: 21 Selected Crops,* 1960-2008 U.S. Department of Agriculture, Economic Research Service Washington, D.C., USA, May 2014.

72. Alfredo, K. S., B.; Roberson, J. A.; Eaton, A., Chlorate challenges for water systems. *J. Am. Water Works Assn.* 2015, 107, E187-E196.

73. Cohen, S. M.; Xu, J. D.; Radkov, E.; Raymond, K. N.; Botta, M.; Barge, A.; Aime, S., Syntheses and relaxation properties of mixed gadolinium hydroxypyridinonate MRI contrast agents. *Inorg. Chem.* 2000, 39, 5747-5756.

74. Jocher, C. J.; Moore, E. G.; Xu, J.; Avedano, S.; Botta, M.; Aime, S.; Raymond, K. N. 1,2-Hydroxypyridonates as Contrast Agents for Magnetic Resonance Imaging: TREN-1,2-HOPO. *Inorg. Chem.* 2007, 46, 9182-9191.

75. Cohen, S. M.; Petoud, S.; Raymond, K. N. A Novel Salicylate-Based Macrobicycle with a "Split Personality". *Inorganic Chemistry* 1999, 38, 4522-4529.

76. E. G. Moore, J. Xu, C. J. Jocher, E. J. Werner, K. N. Raymond, *J. Am. Chem. Soc.* 2006, 128, 10648-10649.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A ligand or a rare earth metal complex of the ligand selected from the group consisting of:

a) ligands of the formula:

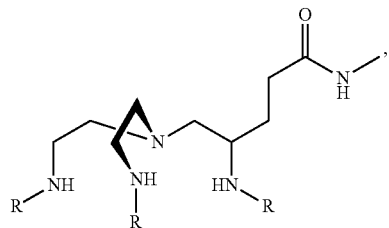

wherein R is selected from the group consisting of

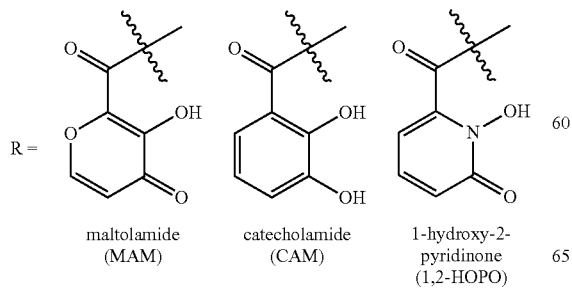

maltolamide (MAM)
catecholamide (CAM)
1-hydroxy-2-pyridinone (1,2-HOPO)

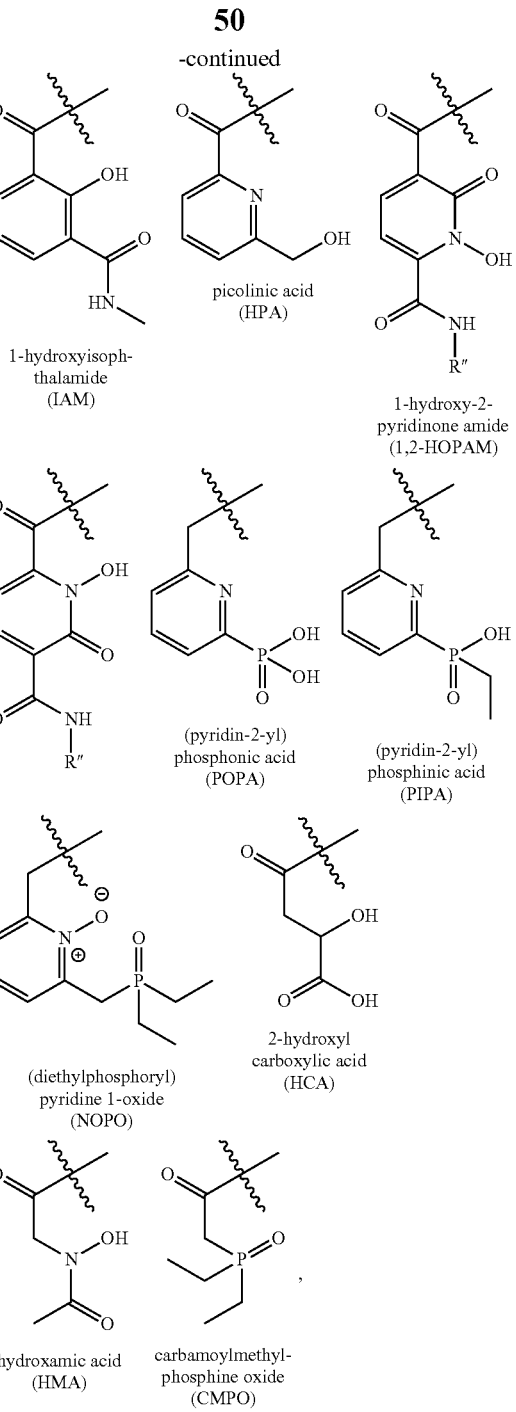

1-hydroxyisoph-thalamide (IAM)
picolinic acid (HPA)
1-hydroxy-2-pyridinone amide (1,2-HOPAM)

(pyridin-2-yl) phosphonic acid (POPA)
(pyridin-2-yl) phosphinic acid (PIPA)

(diethylphosphoryl) pyridine 1-oxide (NOPO)
2-hydroxyl carboxylic acid (HCA)

hydroxamic acid (HMA)
carbamoylmethyl-phosphine oxide (CMPO)

and combinations thereof;

wherein R″ is selected from the group consisting of

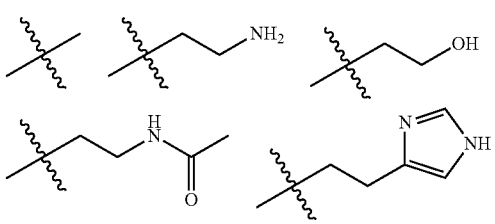

-continued

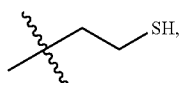

and combinations thereof; and
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof,
or a rare earth metal complex of the ligand;
b) ligands of the formula

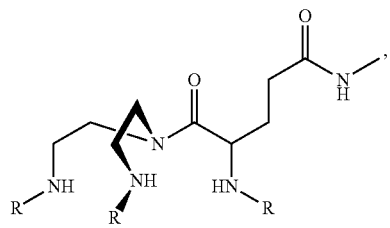

wherein R is selected from the group consisting of

R = 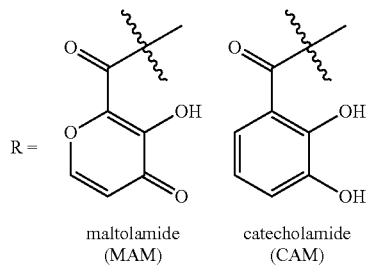

maltolamide (MAM)   catecholamide (CAM)   1-hydroxy-2-pyridinone (1,2-HOPO)

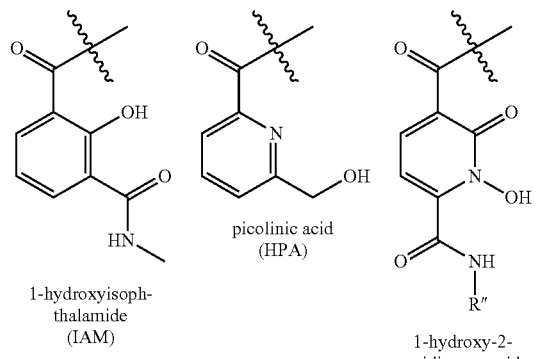

1-hydroxyisoph-thalamide (IAM)   picolinic acid (HPA)   1-hydroxy-2-pyridinone amide (1,2-HOPAM)

-continued

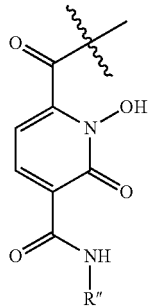 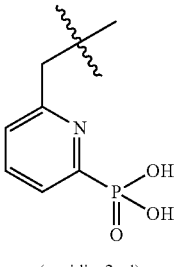 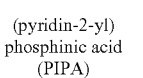

(pyridin-2-yl) phosphonic acid (POPA)   (pyridin-2-yl) phosphinic acid (PIPA)

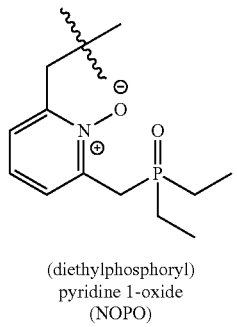 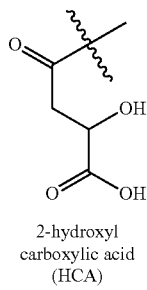

(diethylphosphoryl) pyridine 1-oxide (NOPO)   2-hydroxyl carboxylic acid (HCA)

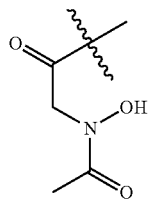 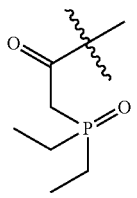

hydroxamic acid (HMA)   carbamoylmethyl-phosphine oxide (CMPO)

and combinations thereof;
wherein R" is selected from the group consisting of

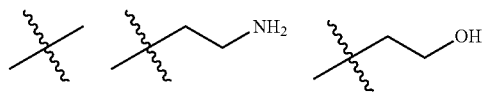

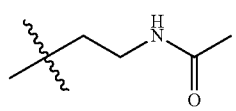 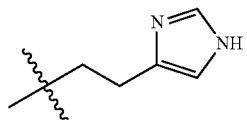

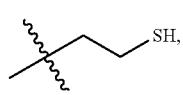

and combinations thereof; and
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand;
c) ligands of the formula

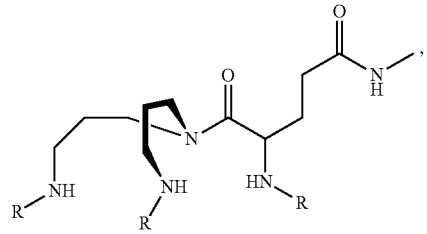

wherein R is selected from the group consisting of

R =

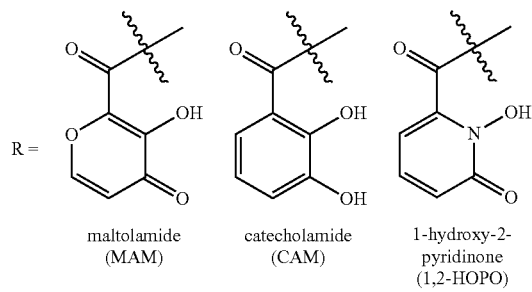

maltolamide (MAM)  catecholamide (CAM)  1-hydroxy-2-pyridinone (1,2-HOPO)

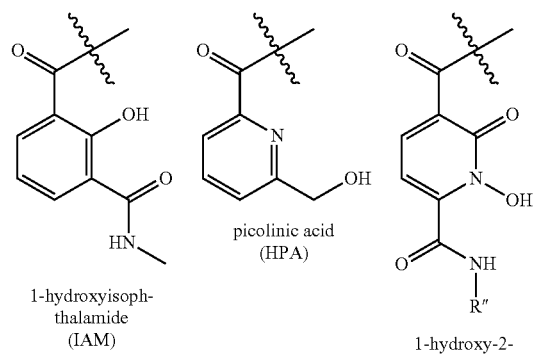

1-hydroxyisoph-thalamide (IAM)  picolinic acid (HPA)  1-hydroxy-2-pyridinone amide (1,2-HOPAM)

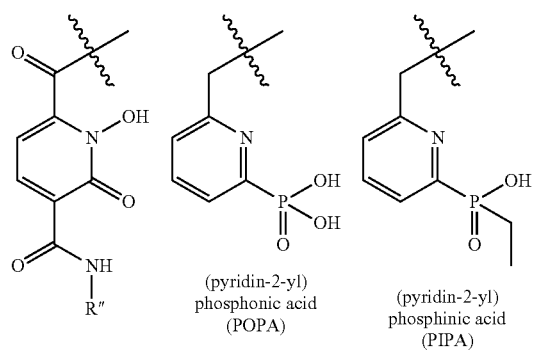

(pyridin-2-yl) phosphonic acid (POPA)  (pyridin-2-yl) phosphinic acid (PIPA)

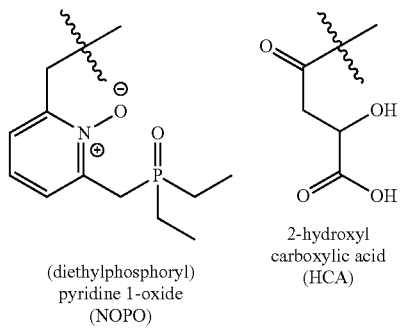

(diethylphosphoryl) pyridine 1-oxide (NOPO)  2-hydroxyl carboxylic acid (HCA)

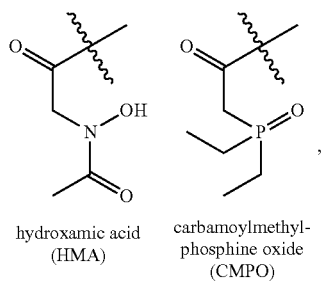

hydroxamic acid (HMA)  carbamoylmethyl-phosphine oxide (CMPO)

and combinations thereof;

wherein R″ is selected from the group consisting of

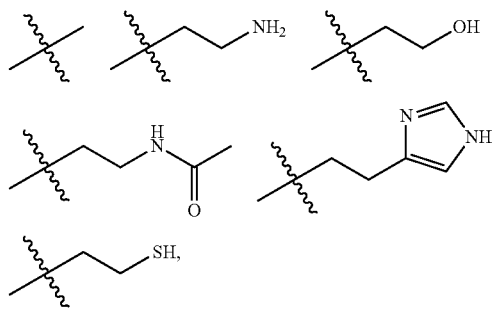

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand;

d) ligands of the formula

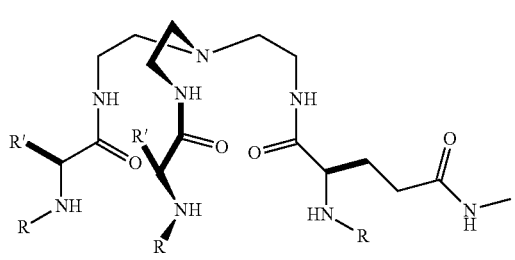

wherein R is selected from the group consisting of

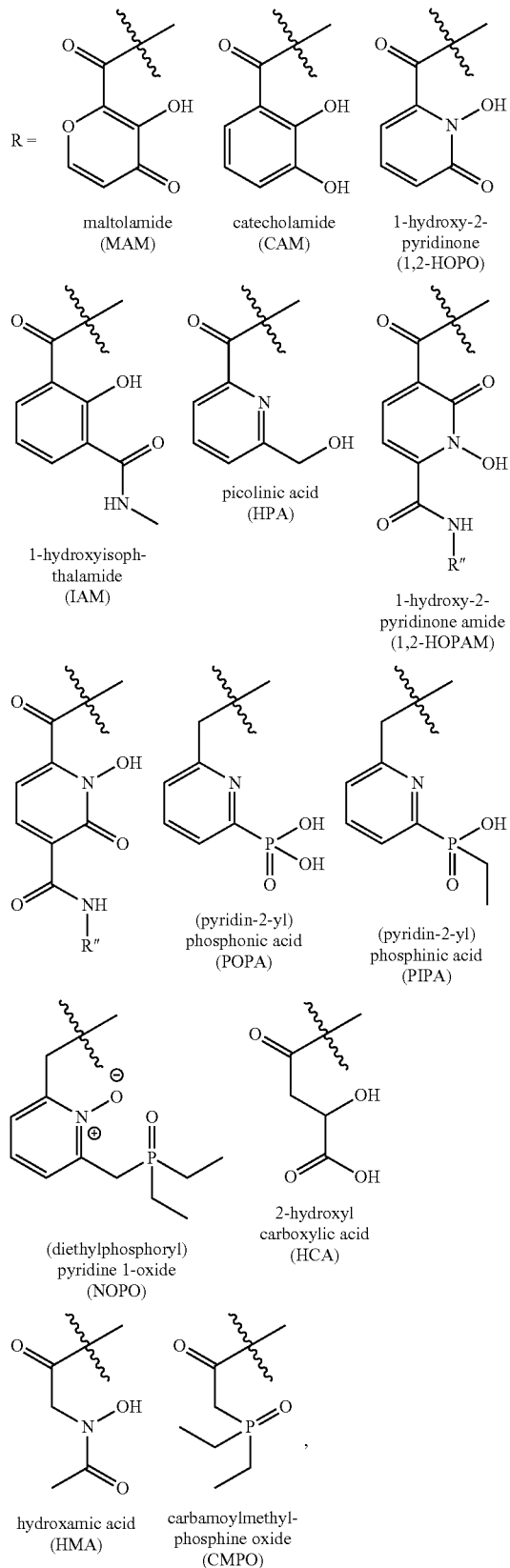

and combinations thereof;

wherein R' is selected from the group consisting of

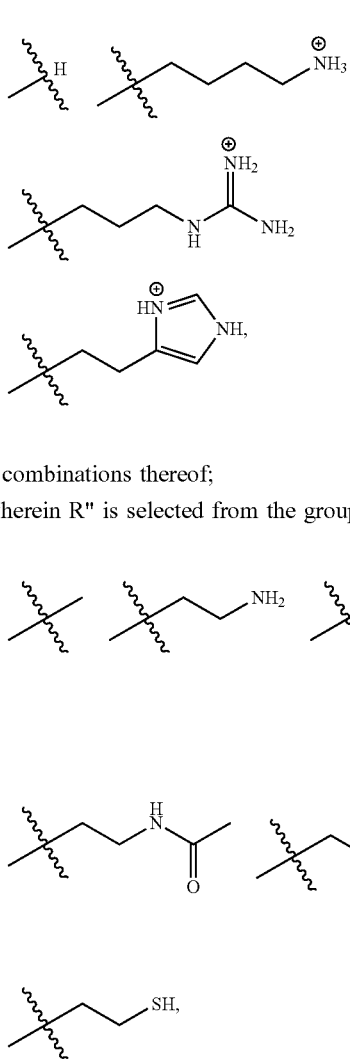

and combinations thereof;

wherein R" is selected from the group consisting of

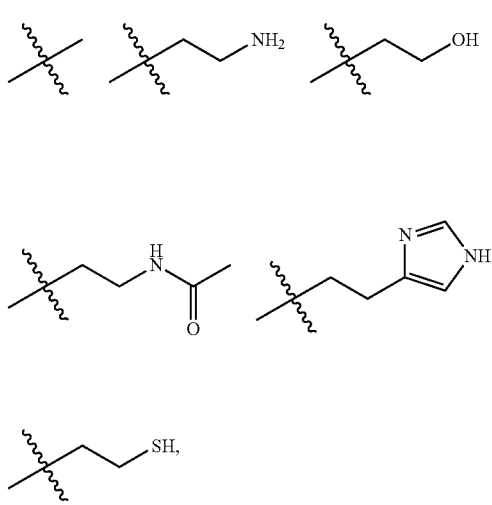

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand;

e) ligands of the formula

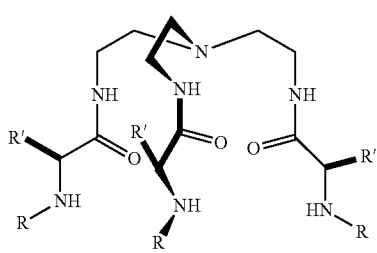

wherein R is selected from the group consisting of

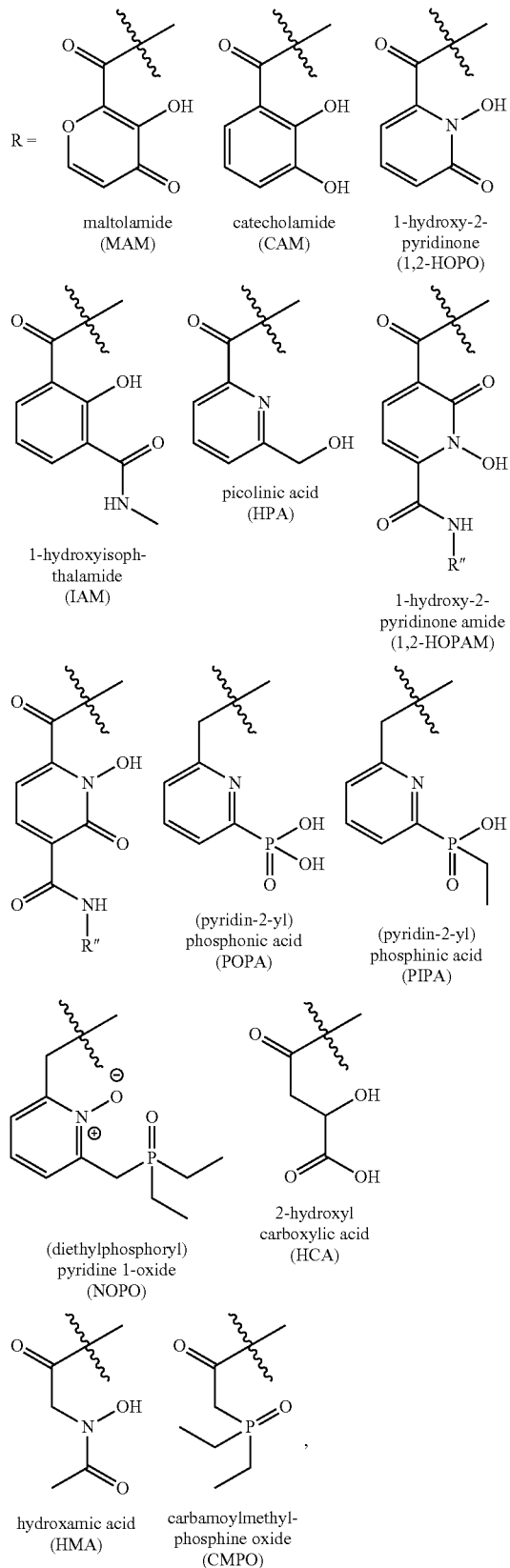

maltolamide (MAM)
catecholamide (CAM)
1-hydroxy-2-pyridinone (1,2-HOPO)
1-hydroxyisoph-thalamide (IAM)
picolinic acid (HPA)
1-hydroxy-2-pyridinone amide (1,2-HOPAM)
(pyridin-2-yl) phosphonic acid (POPA)
(pyridin-2-yl) phosphinic acid (PIPA)
(diethylphosphoryl) pyridine 1-oxide (NOPO)
2-hydroxyl carboxylic acid (HCA)
hydroxamic acid (HMA)
carbamoylmethyl-phosphine oxide (CMPO)

and combinations thereof;

wherein R' is selected from the group consisting of

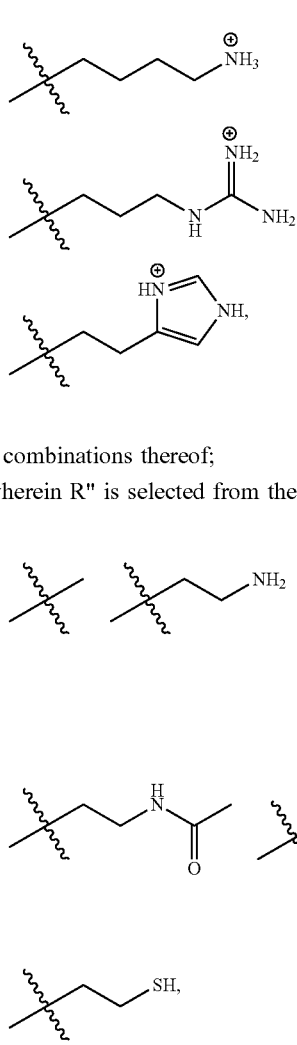

and combinations thereof;

wherein R" is selected from the group consisting of

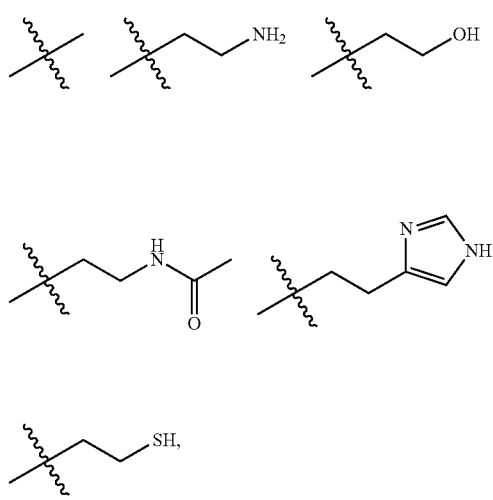

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand;

f) ligands of the formula

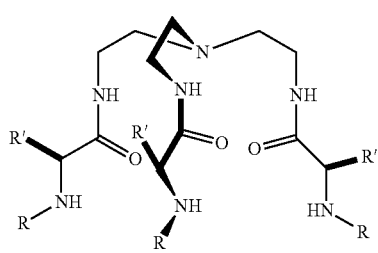

wherein R is selected from the group consisting of

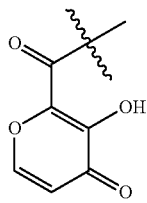 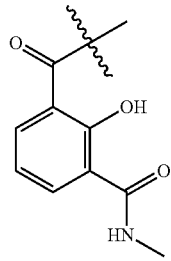

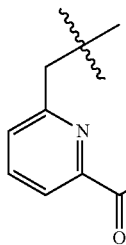 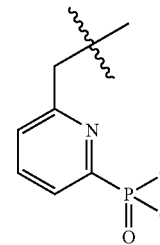

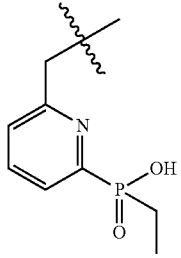 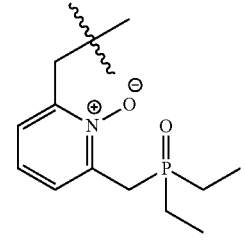

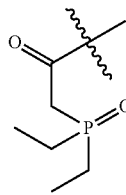 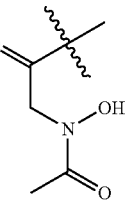 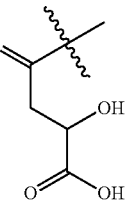

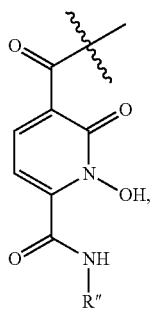

and combinations thereof;
wherein R' is selected from the group consisting of

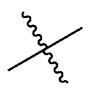 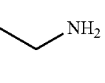 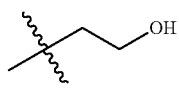

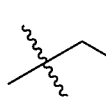 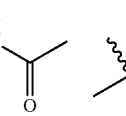 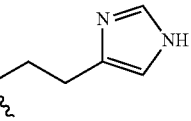

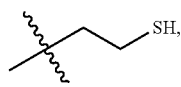

and combinations thereof;
wherein R" is selected from the group consisting of

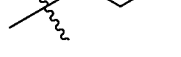

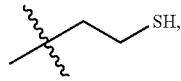

and combinations thereof; and
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand; and g) ligands of the formula

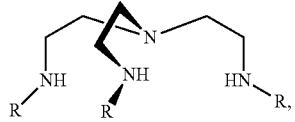

wherein R is selected from the group consisting of

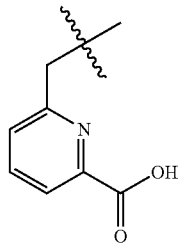 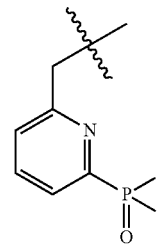

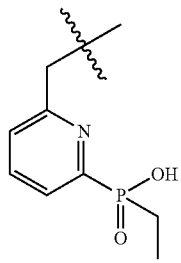 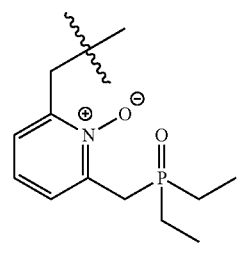

-continued

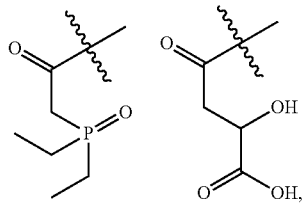

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

2. The ligands or rare earth metal complexes of the ligand according to claim 1, selected from ligands of the formula:

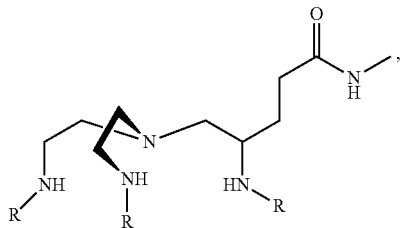

wherein R is selected from the group consisting of

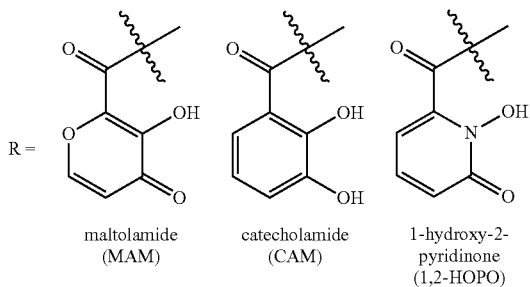

maltolamide (MAM)  catecholamide (CAM)  1-hydroxy-2-pyridinone (1,2-HOPO)

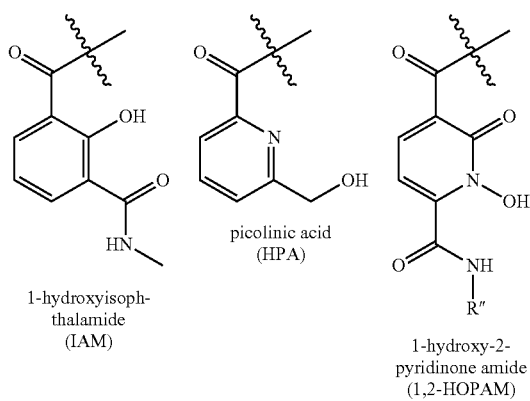

1-hydroxyisoph-thalamide (IAM)   picolinic acid (HPA)   1-hydroxy-2-pyridinone amide (1,2-HOPAM)

-continued

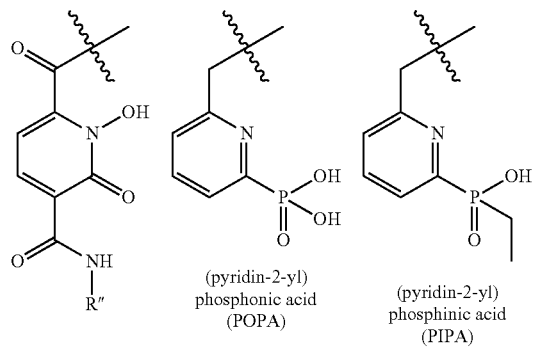

(pyridin-2-yl) phosphonic acid (POPA)   (pyridin-2-yl) phosphinic acid (PIPA)

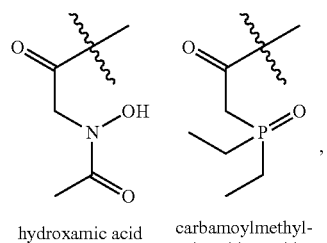

(diethylphosphoryl) pyridine 1-oxide (NOPO)   2-hydroxyl carboxylic acid (HCA)

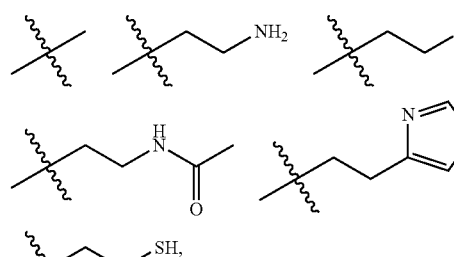

hydroxamic acid (HMA)   carbamoylmethyl-phosphine oxide (CMPO)

and combinations thereof;

wherein R″ is selected from the group consisting of and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

3. The ligands or rare earth metal complexes of the ligand according to claim 1, selected from ligands of the formula:

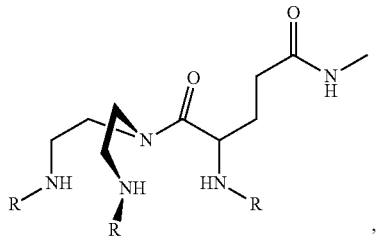

wherein R is selected from the group consisting of

R =

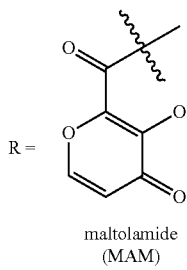
maltolamide (MAM)

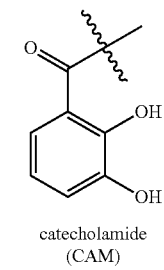
catecholamide (CAM)

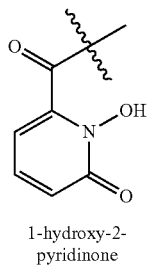
1-hydroxy-2-pyridinone (1,2-HOPO)

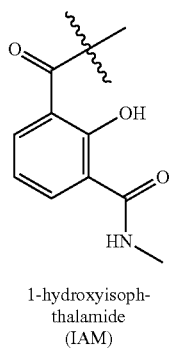
1-hydroxyisoph-thalamide (IAM)

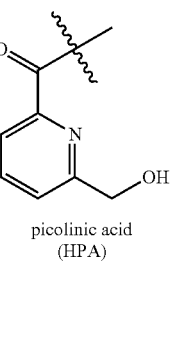
picolinic acid (HPA)

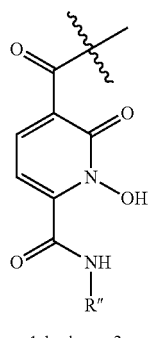
1-hydroxy-2-pyridinone amide (1,2-HOPAM)

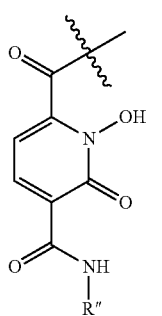
(pyridin-2-yl) phosphonic acid (POPA)

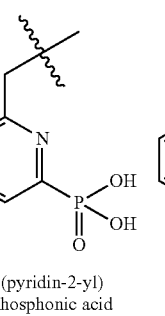
(pyridin-2-yl) phosphinic acid (PIPA)

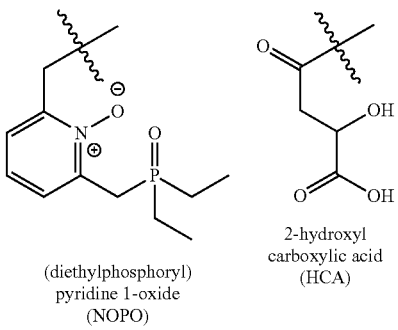

(diethylphosphoryl) pyridine 1-oxide (NOPO)

2-hydroxyl carboxylic acid (HCA)

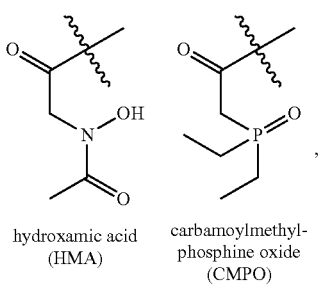

hydroxamic acid (HMA)

carbamoylmethyl-phosphine oxide (CMPO)

and combinations thereof;

wherein R" is selected from the group consisting of

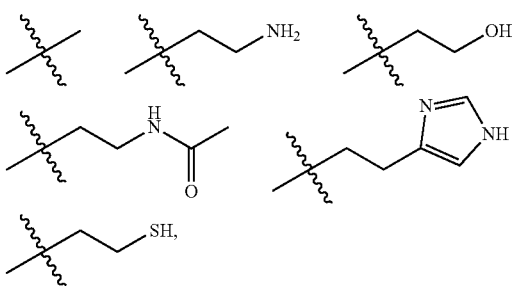

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

4. The ligands or rare earth metal complexes of the ligand according to claim 1, selected from ligands of the formula:

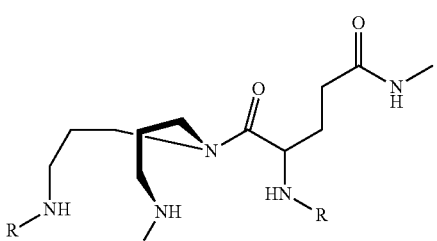

wherein R is selected from the group consisting of

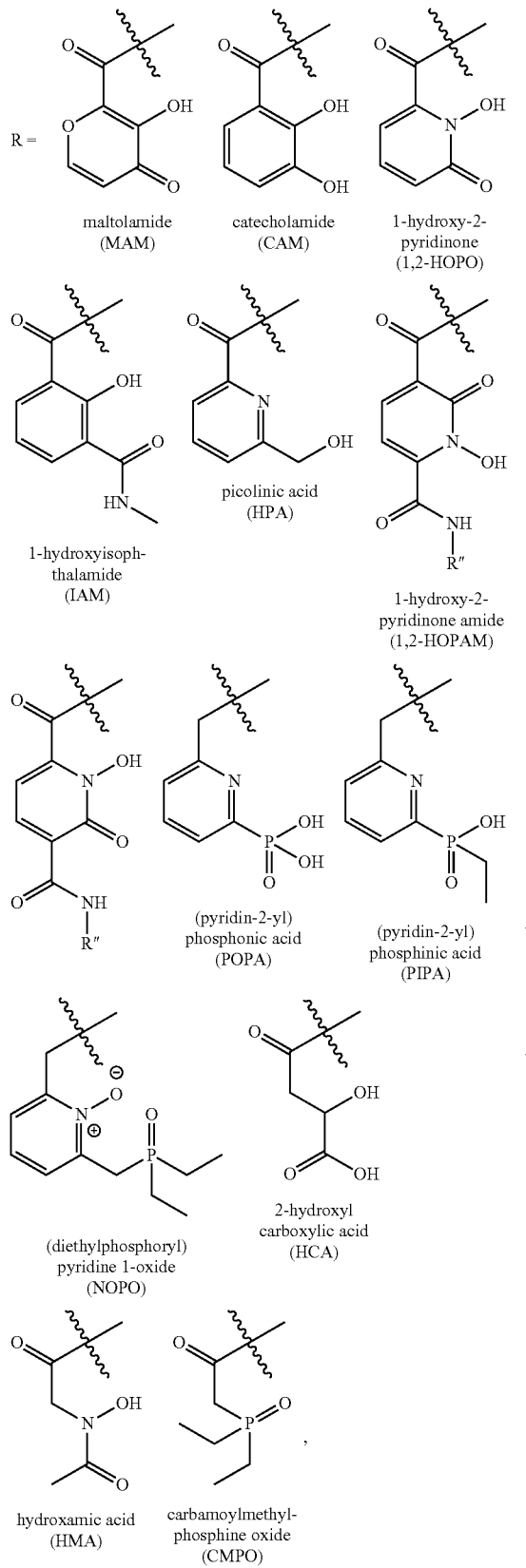

and combinations thereof;

wherein R″ is selected from the group consisting of

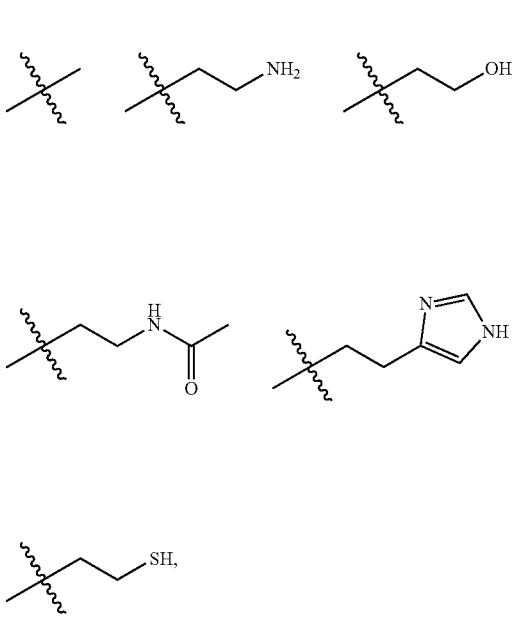

and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

5. The ligands or rare earth metal complexes of the ligand according to claim 1, selected from ligands of the formula:

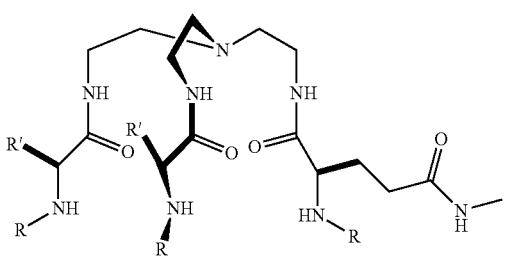

wherein R is selected from the group consisting of

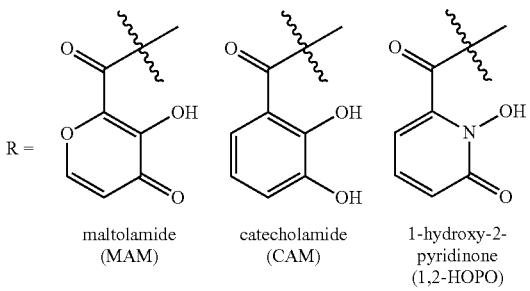

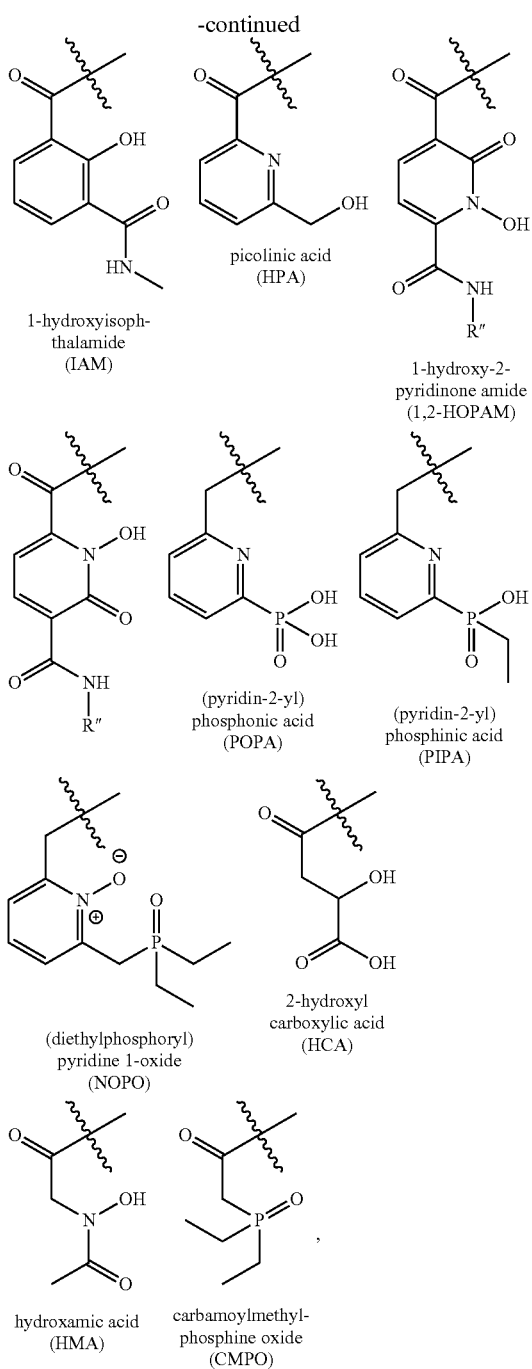

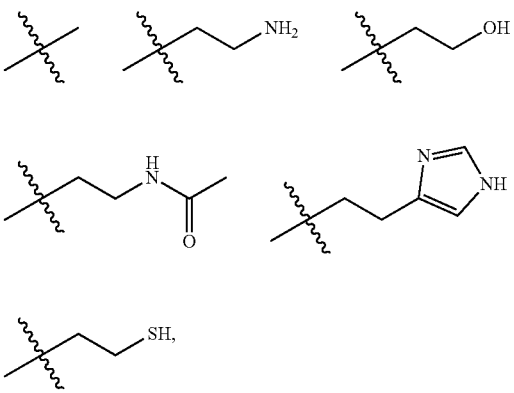

and combinations thereof;

wherein R" is selected from the group consisting of and combinations thereof; and wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

6. The ligands or rare earth metal complexes of the ligand according to claim 1, selected from ligands of the formula:

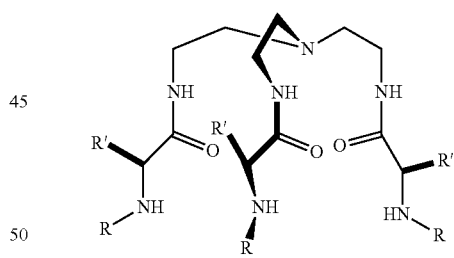

wherein R is selected from the group consisting of and combinations thereof;

wherein R' is selected from the group consisting of

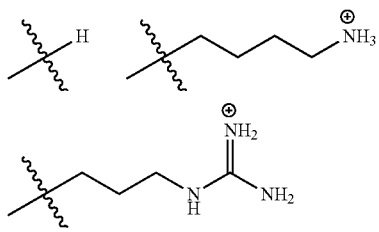

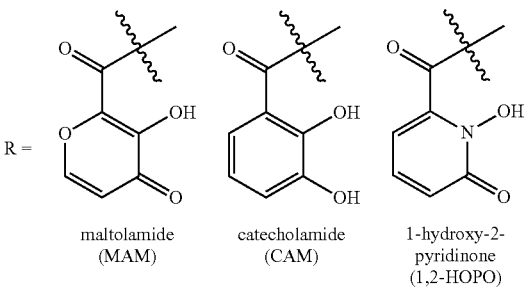

-continued

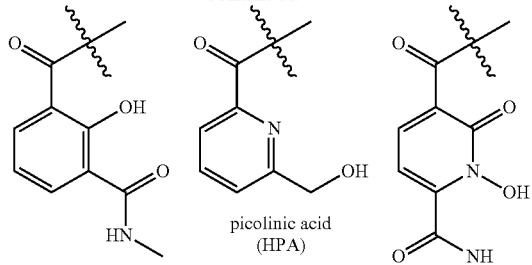

1-hydroxyisoph-
thalamide
(IAM)

picolinic acid
(HPA)

1-hydroxy-2-
pyridinone amide
(1,2-HOPAM)

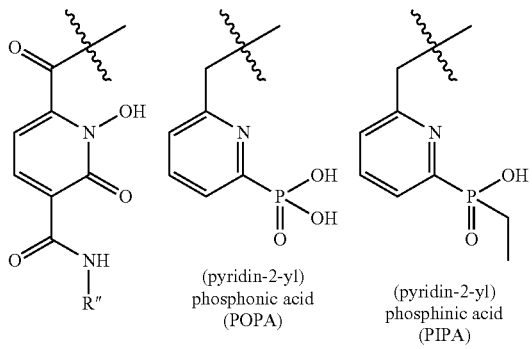

(pyridin-2-yl)
phosphonic acid
(POPA)

(pyridin-2-yl)
phosphinic acid
(PIPA)

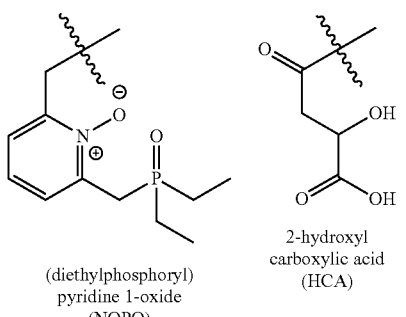

(diethylphosphoryl)
pyridine 1-oxide
(NOPO)

2-hydroxyl
carboxylic acid
(HCA)

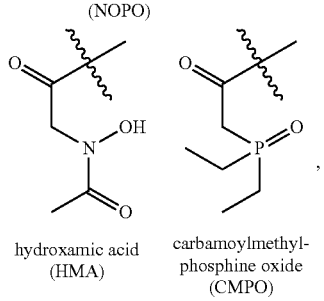

hydroxamic acid
(HMA)

carbamoylmethyl-
phosphine oxide
(CMPO)

and combinations thereof;
wherein R' is selected from the group consisting of

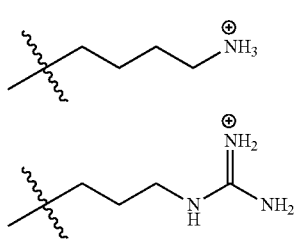

-continued

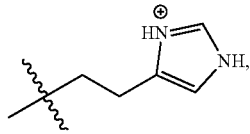

and combinations thereof;
wherein R" is selected from the group consisting of

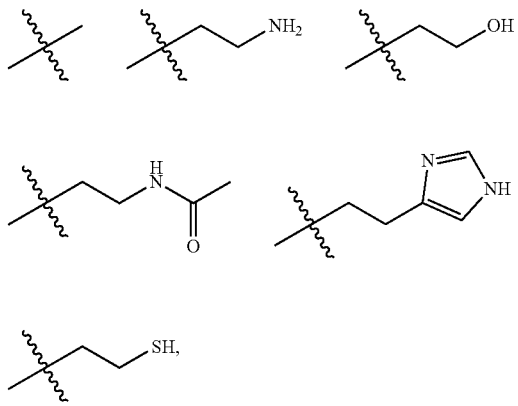

and combinations thereof; and
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof,
or a rare earth metal complex of the ligand.

7. The ligands or rare earth metal complexes of the ligand according to claim 1, selected from ligands of the formula:

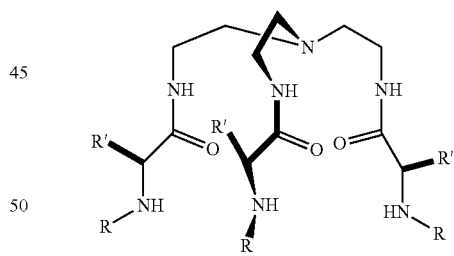

wherein R is selected from the group consisting of

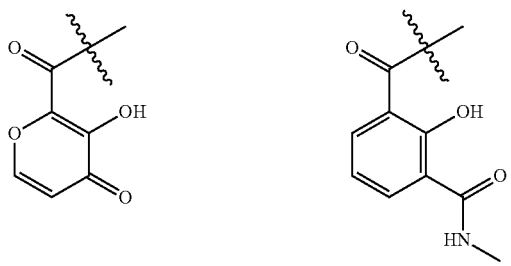

-continued

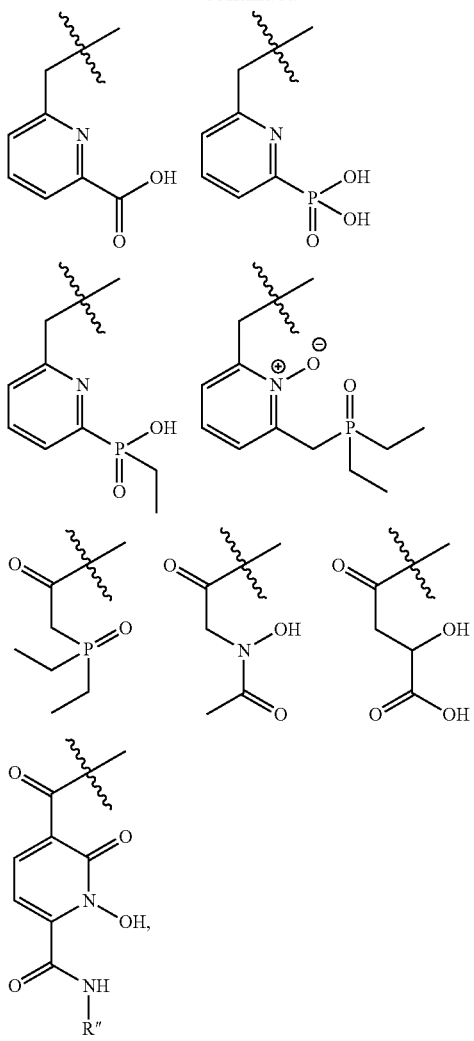

and combinations thereof;
wherein R' is selected from the group consisting of

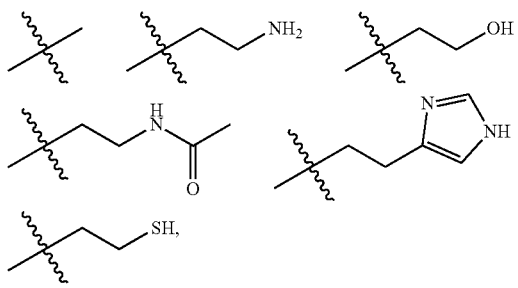

and combinations thereof;
wherein R" is selected from the group consisting of

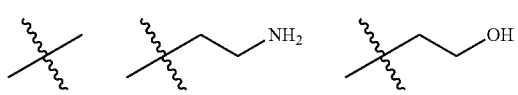

-continued

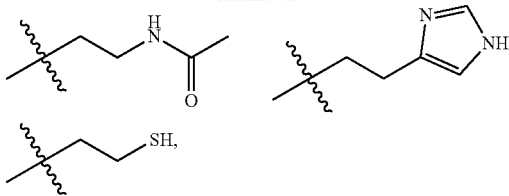

and combinations thereof; and
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

8. A ligand or a rare earth metal complex of the ligand, wherein the ligand is of the formula:

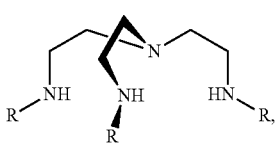

wherein R is selected from the group consisting of

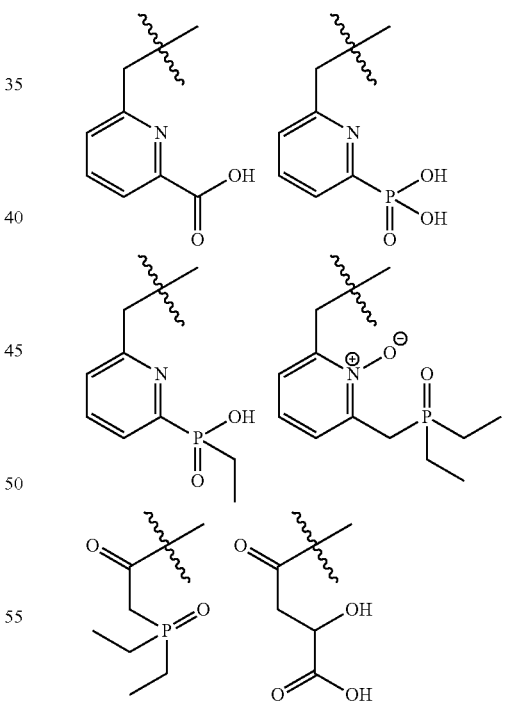

and combinations thereof;
wherein optionally the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, or a rare earth metal complex of the ligand.

9. A rare earth metal complex of a ligand selected from the group consisting of:
a) rare earth metal complexes of a ligand having the formula

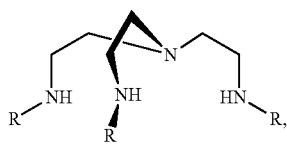

wherein R is

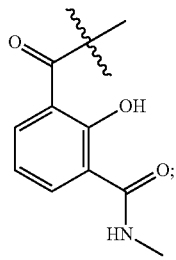 [SMILES: *C(=O)c1cccc(C(=O)NC)c1O]

and
wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof; and
b) rare earth metal complexes of a ligand having the formula

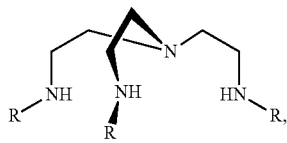

wherein R is selected from the group consisting of

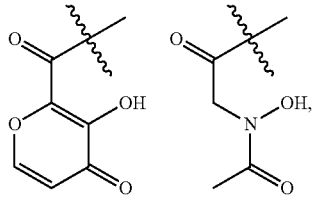

and combinations thereof; and
wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

10. A method for sensing, detecting, and/or selectively capturing phosphate from water comprising:
contacting a ligand or a rare earth metal complex of the ligand according to claim 1 with an aqueous phosphate-containing medium at a pH of 5 to 12 under conditions sufficient to bind phosphate.

11. The method of claim 10 wherein the ligand or the rare earth metal complex of the ligand reversibly binds the phosphate.

12. The method of claim 11, further comprising releasing the bound phosphate by contacting the bound phosphate complex with an aqueous medium at a pH of 0 to 4 under conditions sufficient to release the bound phosphate.

13. A device for sensing, detecting, and/or selectively capturing phosphate from water having a ligand or a rare earth metal complex of the ligand attached thereto,
wherein the ligand is selected from the group consisting of

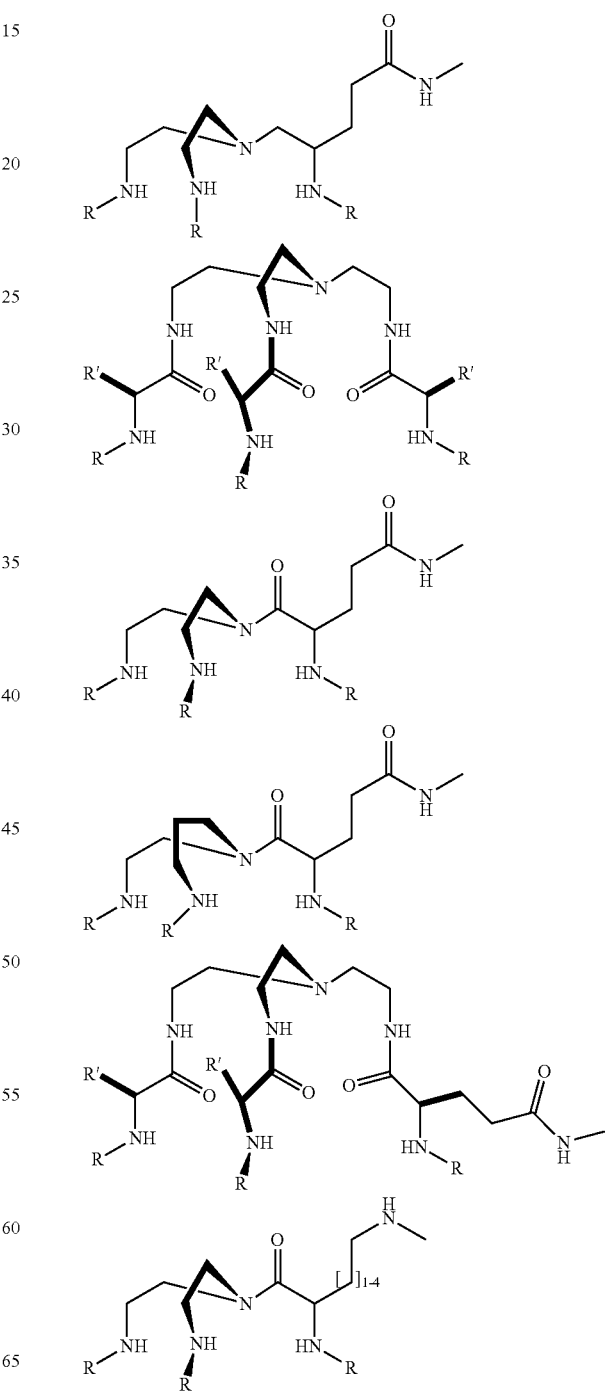

-continued

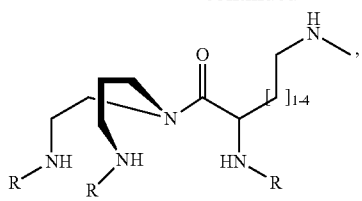

and combinations thereof;
wherein R is selected from the group consisting of

R =

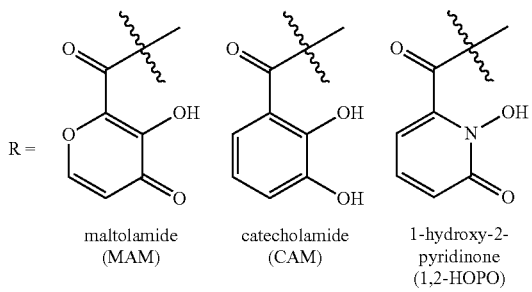

maltolamide (MAM)    catecholamide (CAM)    1-hydroxy-2-pyridinone (1,2-HOPO)

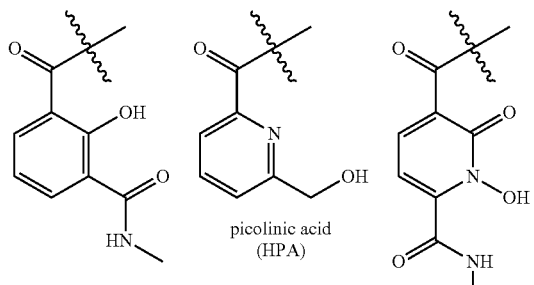

1-hydroxyisoph-thalamide (IAM)    picolinic acid (HPA)    1-hydroxy-2-pyridinone amide (1,2-HOPAM)

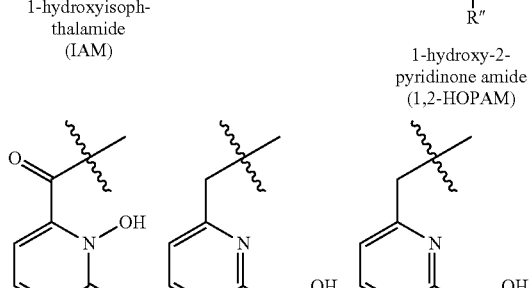

(pyridin-2-yl) phosphonic acid (POPA)    (pyridin-2-yl) phosphinic acid (PIPA)

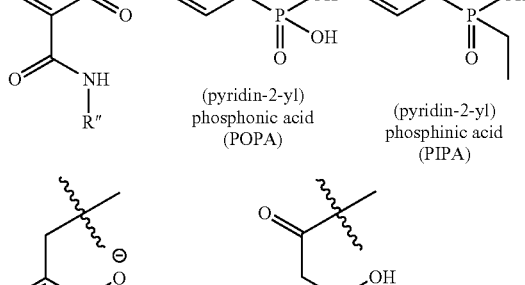

(diethylphosphoryl) pyridine 1-oxide (NOPO)    2-hydroxyl carboxylic acid (HCA)

-continued

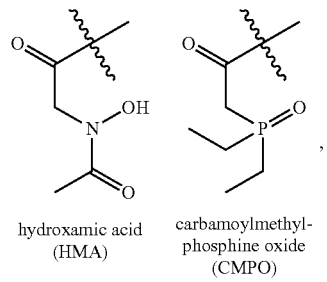

hydroxamic acid (HMA)    carbamoylmethyl-phosphine oxide (CMPO)

and combinations thereof;
wherein $R^a$ is selected from the group consisting of

R =

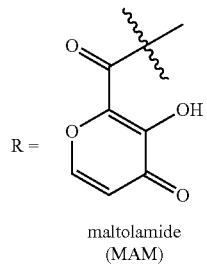

maltolamide (MAM)

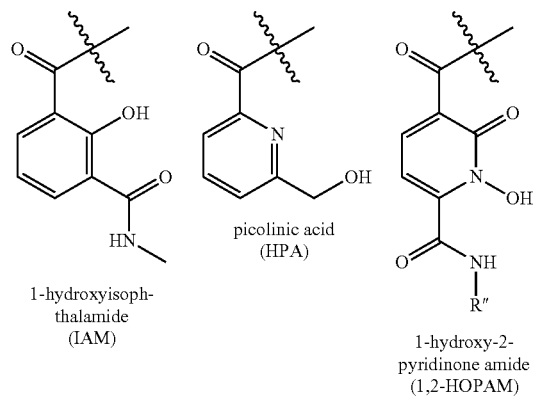

1-hydroxyisoph-thalamide (IAM)    picolinic acid (HPA)    1-hydroxy-2-pyridinone amide (1,2-HOPAM)

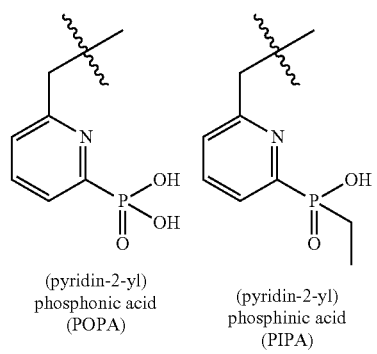

(pyridin-2-yl) phosphonic acid (POPA)    (pyridin-2-yl) phosphinic acid (PIPA)

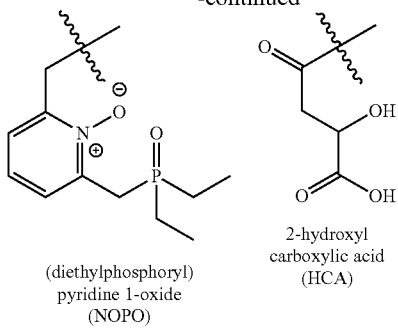

(diethylphosphoryl) pyridine 1-oxide (NOPO)

2-hydroxyl carboxylic acid (HCA)

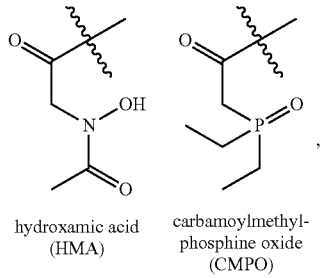

hydroxamic acid (HMA)

carbamoylmethyl-phosphine oxide (CMPO)

and combinations thereof;
wherein R' is selected from the group consisting of

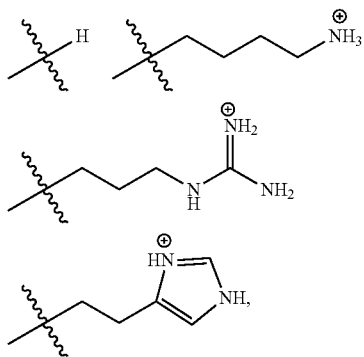

and combinations thereof;
wherein R" is selected from the group consisting of

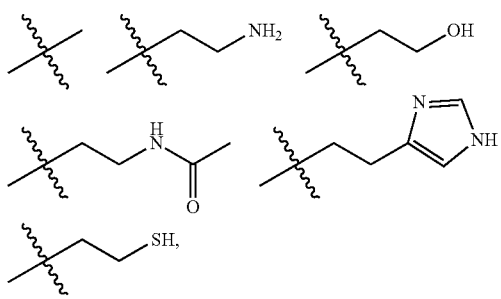

and combinations thereof; and
wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof.

14. A device for sensing, detecting, and/or selectively capturing phosphate from water having a ligand or a rare earth metal complex of the ligand attached thereto, wherein the ligand is selected from the group consisting of

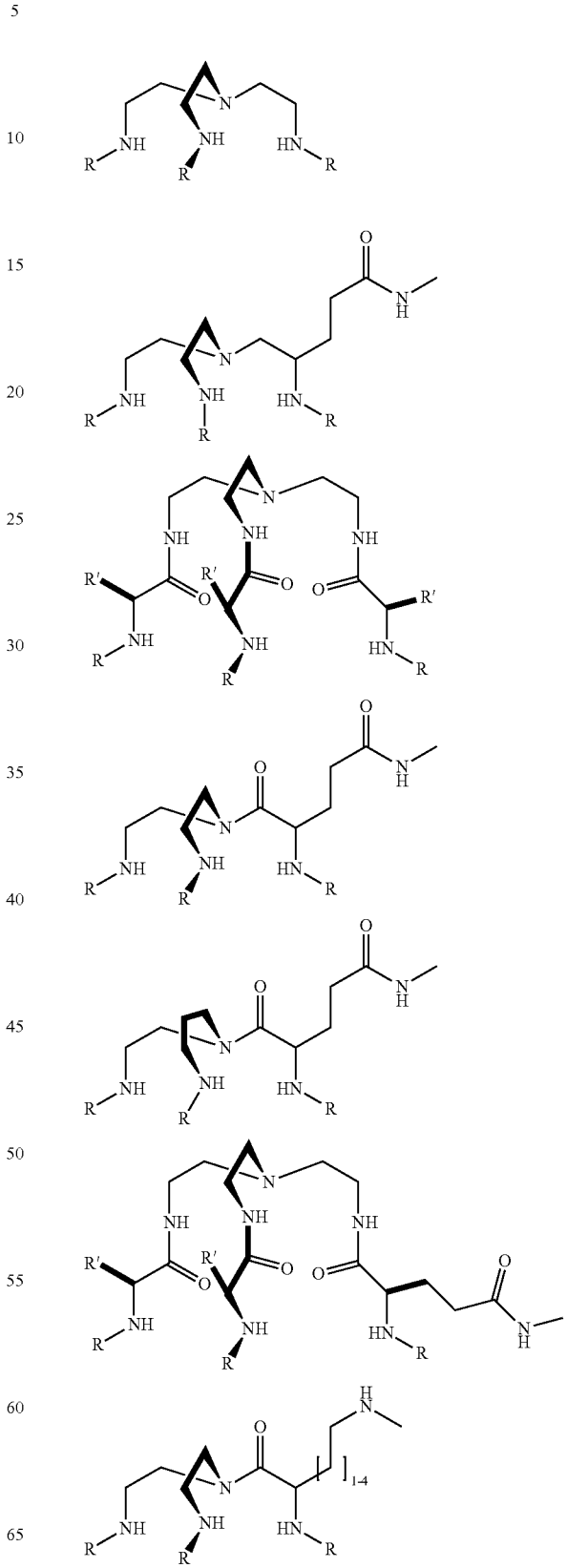

and combinations thereof;
wherein R is selected from the group consisting of

R = maltolamide (MAM), catecholamide (CAM), 1-hydroxy-2-pyridinone (1,2-HOPO), 1-hydroxyisophthalamide (IAM), picolinic acid (HPA), 1-hydroxy-2-pyridinone amide (1,2-HOPAM), (pyridin-2-yl) phosphonic acid (POPA), (pyridin-2-yl) phosphinic acid (PIPA), (diethylphosphoryl) pyridine 1-oxide (NOPO), 2-hydroxyl carboxylic acid (HCA), hydroxamic acid (HMA), carbamoylmethyl-phosphine oxide (CMPO)

and combinations thereof;
wherein R' is selected from the group consisting of and combinations thereof;
wherein R″ is selected from the group consisting of and combinations thereof; and
wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, and wherein the device comprises a membrane having the ligand or the rare earth metal complex of the ligand attached thereto.

15. The device of claim 13, wherein the device comprises a sensor or detector having the ligand or the rare earth metal complex of the ligand attached thereto.

16. A device for sensing, detecting, and/or selectively capturing phosphate from water having a ligand or a rare earth metal complex of the ligand attached thereto, wherein the ligand is selected from the ligand or combinations thereof according to claim 1, and
wherein the rare earth metal of the rare earth metal complex of one or more of the ligands is selected from the group consisting of $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and combinations thereof, and wherein the device comprises a membrane having the ligand or the rare earth metal complex of the ligand attached thereto.

17. The device of claim 16, wherein the device comprises a sensor or detector having the ligand or the rare earth metal complex of the ligand attached thereto.

\* \* \* \* \*

UNITED STATES PATENT AND TRADEMARK OFFICE
CERTIFICATE OF CORRECTION

PATENT NO. : 11,136,251 B2  
APPLICATION NO. : 15/934530  
DATED : October 5, 2021  
INVENTOR(S) : Valerie Christine Pierre et al.

It is certified that error appears in the above-identified patent and that said Letters Patent is hereby corrected as shown below:

In the Claims

Column 77, Line 66, Claim 13, please delete "$Sm^{3+}$, $Eu^{3+}$, $Tb^{3+}$," and insert -- $Sm^{3+}$, $Eu^{3+}$, $Gd^{3+}$, $Tb^{3+}$, -- therefor.

Signed and Sealed this  
First Day of February, 2022

Drew Hirshfeld  
*Performing the Functions and Duties of the*  
*Under Secretary of Commerce for Intellectual Property and*  
*Director of the United States Patent and Trademark Office*

UNITED STATES PATENT AND TRADEMARK OFFICE
CERTIFICATE OF CORRECTION

PATENT NO. : 11,136,251 B2  
APPLICATION NO. : 15/934530  
DATED : October 5, 2021  
INVENTOR(S) : Valerie Christine Pierre et al.

Page 1 of 4

It is certified that error appears in the above-identified patent and that said Letters Patent is hereby corrected as shown below:

In the Claims

Column 74, Claim 13, structure 4, Lines 42-49, please delete:

"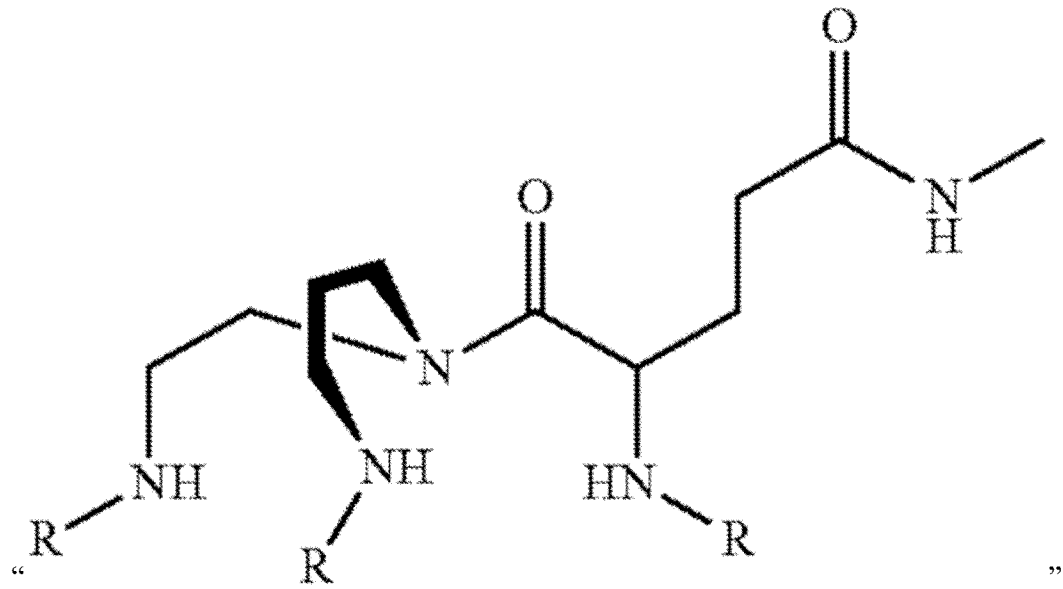"

Signed and Sealed this  
Ninth Day of January, 2024

Katherine Kelly Vidal  
*Director of the United States Patent and Trademark Office*

CERTIFICATE OF CORRECTION (continued)
U.S. Pat. No. 11,136,251 B2

Page 2 of 4

And insert:

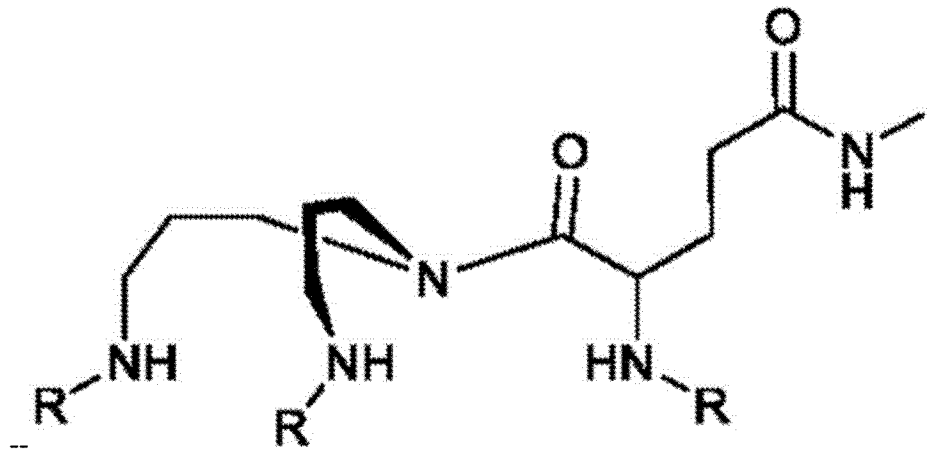

-- therefore.

Column 75, Claim 13, structure 7, Lines 1-10, please delete:

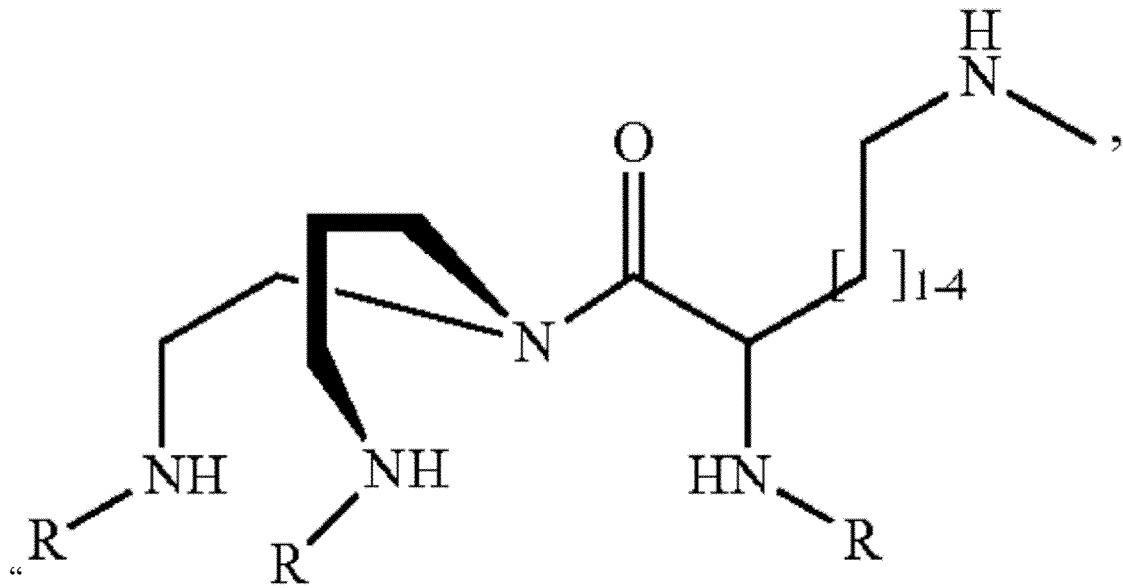

And insert:

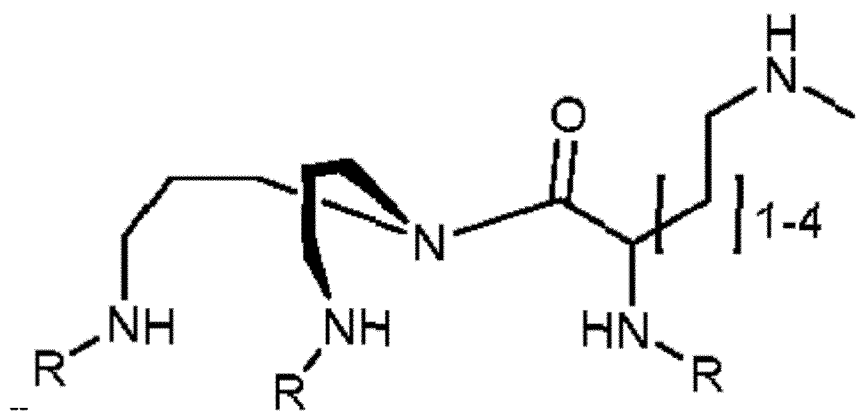

-- therefore.

Column 78, Claim 14, structure 5, Lines 42-49, please delete:
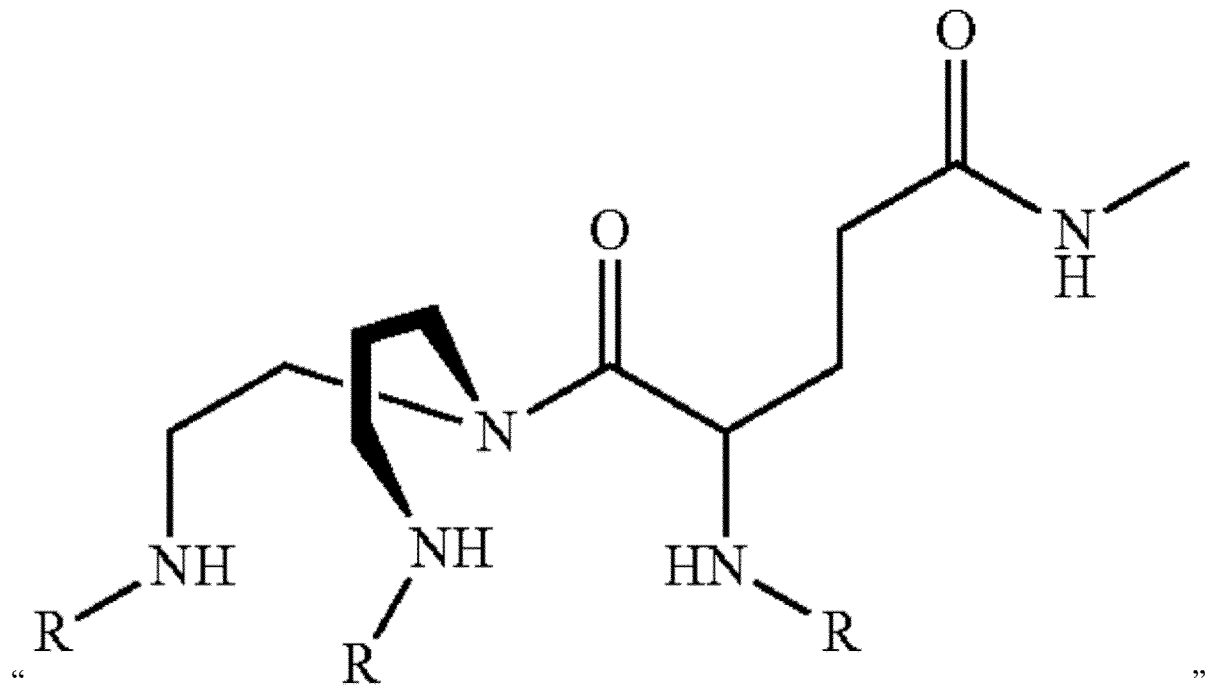
"                                                                                                "
And insert:
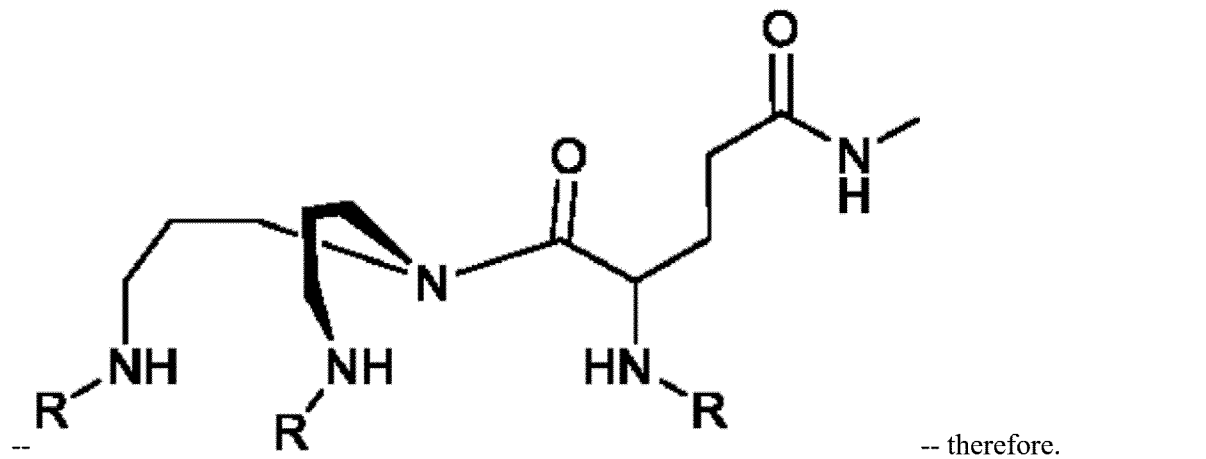
--                                                                                  -- therefore.
Column 79, Claim 14, structure 8, Lines 1-10, please delete:

CERTIFICATE OF CORRECTION (continued)
U.S. Pat. No. 11,136,251 B2

"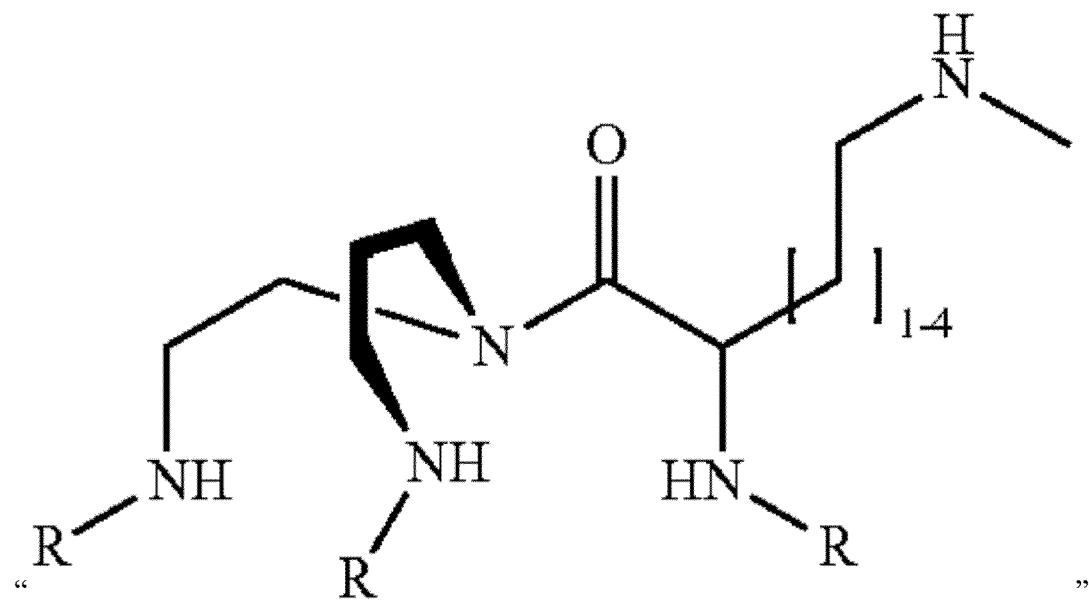"

And insert:

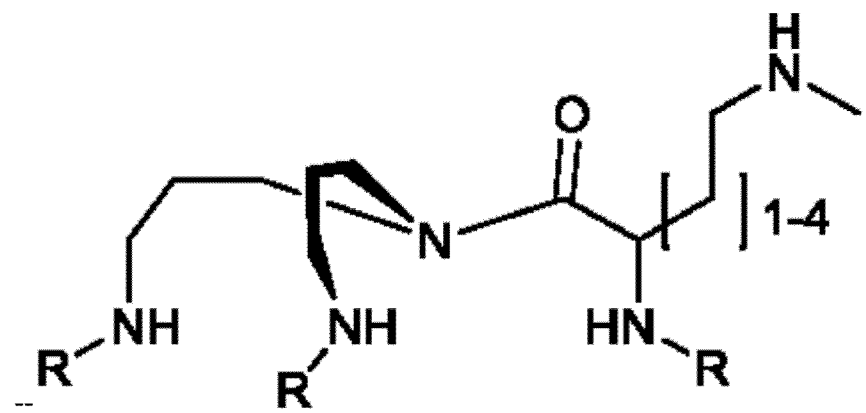

-- therefore.